United States Patent
Chow et al.

(10) Patent No.: US 9,540,669 B2
(45) Date of Patent: Jan. 10, 2017

(54) TRICHODERMA REESEI GLUCOAMYLASE VARIANTS RESISTANT TO OXIDATION-RELATED ACTIVITY LOSS AND THE USE THEREOF

(71) Applicant: DANISCO US INC., Palo Alto, CA (US)

(72) Inventors: Su Yin Marina Chow, Mountain View, CA (US); Thomas P. Graycar, Pacifica, CA (US); Jacquelyn A. Huitink, Burlingame, CA (US); Casper Vroemen, Oegstgeest (NL); David L. Wong, San Jose, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 14/419,906

(22) PCT Filed: Aug. 12, 2013

(86) PCT No.: PCT/US2013/054462
§ 371 (c)(1),
(2) Date: Feb. 5, 2015

(87) PCT Pub. No.: WO2014/028358
PCT Pub. Date: Feb. 20, 2014

(65) Prior Publication Data
US 2016/0068879 A1    Mar. 10, 2016

Related U.S. Application Data

(60) Provisional application No. 61/683,007, filed on Aug. 14, 2012.

(51) Int. Cl.
*C12N 9/34*      (2006.01)
*C12P 19/20*      (2006.01)
(Continued)

(52) U.S. Cl.
CPC ............ *C12P 19/20* (2013.01); *C12N 9/2428* (2013.01); *C12P 7/10* (2013.01); *C12P 19/02* (2013.01);
(Continued)

(58) Field of Classification Search
None
See application file for complete search history.

(56) References Cited

U.S. PATENT DOCUMENTS 4,794,175 A    12/1988   Nunberg et al.
4,863,864 A    9/1989   Ashikari et al.
(Continued)

FOREIGN PATENT DOCUMENTS

DE   WO 2011020852 A1 *   2/2011   ............. A23L 1/095
DK   WO 2012001139 A1 *   1/2012   ............. A23L 1/095
(Continued)

OTHER PUBLICATIONS

GenBank Accession No. EHK25059.1, published Nov. 29, 2011.*
(Continued)

*Primary Examiner* — Robert Mondesi
*Assistant Examiner* — Richard Ekstrom
(74) *Attorney, Agent, or Firm* — Danisco US Inc.

(57) ABSTRACT

Embodiments of the present disclosure relate to *Trichoderma reesei* glucoamylase (TrGA) variants having improved properties (e.g., improved thermostability, improved specific activity, and/or resistant to oxidation-related activity loss). Also provided are compositions comprising variant glucoamylases. These compositions are useful in various starch process applications.

24 Claims, 13 Drawing Sheets

(51) Int. Cl.
*C12P 19/14* (2006.01)
*C12P 19/02* (2006.01)
*C12P 7/10* (2006.01)

(52) U.S. Cl.
CPC ........ *C12P 19/14* (2013.01); *C12Y 302/01003* (2013.01); *C12P 2203/00* (2013.01); *Y02P 20/52* (2015.11)

(56) References Cited

U.S. PATENT DOCUMENTS

| | | | |
|---|---|---|---|
| 6,255,084 B1 | 7/2001 | Nielsen et al. | |
| 6,620,924 B2 | 9/2003 | Nielsen et al. | |
| 7,413,879 B2 * | 8/2008 | Dunn-Coleman | C12N 9/242 435/161 |
| 8,058,033 B2 * | 11/2011 | Aehle | C12N 9/2428 435/205 |
| 8,592,194 B2 * | 11/2013 | Aehle | C07H 21/04 435/183 |

FOREIGN PATENT DOCUMENTS

| | | | | |
|---|---|---|---|---|
| WO | WO95/26397 | 10/1995 | | |
| WO | WO2005/001036 | 1/2005 | | |
| WO | WO 2008045489 A2 * | 4/2008 | ........... | C12N 9/2428 |
| WO | WO 2009048487 A1 * | 4/2009 | ........... | C12N 9/2428 |
| WO | WO 2009048488 A1 * | 4/2009 | ........... | C12N 9/2428 |
| WO | WO 2011022465 A1 * | 2/2011 | ............. | A23L 1/095 |

OTHER PUBLICATIONS

International Preliminary Report on Patentability in PCT/US2013/054462, mailed Feb. 17, 2015.*

Aleshin, A.E., et al., "Refined crystal structures of glucoamylase from *Aspergillus awamori* var. X100." *J. Mol. Biol.* 238: 575-591, 1994.

Boel, E., et al., "Two different types of intervening sequences in the glucoamylase gene from *Aspergillus niger*." *EMBO J.* 3(7):1581-1585, 1984.

Boel, E., et al., "Glucoamylases G1 and G2 from *Aspergillus niger* are synthesized from two different but closely related mRNAs." *EMBO J.* 3(5): 1097-1102, 1984.

Chi, M-C., et al., "Engineering of a truncated alpha-amylase of *Bacillus* sp. Strain TS-23 for the simultaneous improvement of thermal and oxidative stabilities." *J. Bioscience and Bioeng.* 109(6): 531-538, 2010.

Estell, D.A., et al., "Engineering an Enzyme by Site-directed Mutagenesis to be Resistant to Chemical Oxidation." *J. Biol. Chem.* 260(11): 6518-6521, 1985.

GenBank Accession No. EHK49034.1; Definition: Glycoside hydrolase family 15 protein [*Trichoderma atroviride* IMI 206040]; Kubicek, C.P., et al., Nov. 29, 2011.

GenBank Accession No. D86235; Definition: Trichoderma reesei chb1 gene for cellobiohydrolase I, upstream region; Trichoderma reesei; Takashima, S., et al., Oct. 29, 1997.

International Search Report and the Written Opinion of the International Searching Authority for International Application No. PCT/US2013/054462 dated Oct. 29, 2013.

* cited by examiner

FIG. 1A

```
SEQ ID NO  2  ------------------------  ------------------SVDDFIS  TETPIALNNLLCNVGPDGCR   27
SEQ ID NO  7  MHVLSTAVLLGLVAVQKVLG      RPGLNGVPDVTKRSVDDFIS      NESPIALNNLLCNVGPDGCR   60
SEQ ID NO  8  MHVLSTAVLLGSVAVQKVLG      RPGSNGLSGVTKRSVDDFIN      TQTPIALNNLLCNVGPDGCR   60
SEQ ID NO  9  MHVLSTAVLLGSVAVQKVLG      RPGSSGLYDVTKRSVDDFIS      TETPIALNNLLCNVGPDGCR   60
SEQ ID NO 10  MHVLSTAVLLGSVAVQKVLG      RPGSSNGLSGVTKRSVDDFIN      TQTPIALNNLLCNVGPDGCR   60
SEQ ID NO 11  MHVLSTAVLLGSVAVQKVLG      RPGSSGLSGVTKRSVDDFIS      TETPIALNNLLCNVGPDGCR   60
SEQ ID NO 12  MHVLSTAVLLGSVAVQKVLG      RPGSSGLSDVTKRSVDDFIS      TQTPIALNNLLCNVGPDGCR   60
SEQ ID NO 13  MHVLSTAVLLGSVAVQKVLG      RPGAS---DITKRAVTDFIN      SETPIALNNLICNVGPDGCR   57
SEQ ID NO 14  MHVLSTAVLLGSVAVQKVLG      RPGSNGLSGVTKRSVDDSIN      TQTPIALNNLLCNVGPDGCR   60
SEQ ID NO 15  MHVLSTAVLLGSVAVQKVLG      RPGSSGLSDVTKRSVDDFIS      TETPIALNNLLCNVGPDGCR   60
SEQ ID NO 16  MHVLSTAVLLGSVAVQKVLG      RPGSNGLSGVTKRSVDDFIN      TQTPIALNNLLCNVGPDGCR   60
SEQ ID NO 17  MHVLSTAVLLGSVAVQKVLG      RPGSSGLSDITKRSVDDFIS      TQTPIALNNLLCNVGPDGCR   60
SEQ ID NO 18  MHVLSTAVLLGSVAVQKVLG      RPGSNGLSDITKRSVDSFIS      AETPIALNNLLCNVGPDGCR   60
SEQ ID NO 19  MHVLSTAVLLGSVAVQKVLG      RPGAS---DITKRAVTDFIN      SETPIALNNLICNVGPDGCR   57
                       *                         *                *   ************

SEQ ID NO  2  AFGTSAGAVIASPSTIDPDY      YYMWTRDSALVFKNLIDRFT      ETYDAGLQRRIEQYITAQVT   87
SEQ ID NO  7  AFGASAGTVAASPSTTDPDY      YYMWTRDSALIFKTVVDRFT      QNYDASLQKRIEQYIAAQAT  120
SEQ ID NO  8  AFGTSAGAVIASPSTTDPDY      YYMWTRDSALVFKNLVDRFT      QQYDAGLQRRIEQYISAQVT  120
SEQ ID NO  9  AFGTSAGAVIASPSTTDPDY      YYMWTRDSALVFKNLVDRFT      EEYDAGLQRRIEQYITAQVT  120
SEQ ID NO 10  AFGTSAGAVIASPSTTDPDY      YYMWTRDSALVFKNIVDRFT      QQYDAGLQRRIEQYISAQVT  120
SEQ ID NO 11  AFGTSAGAVIASPSTTDPDY      YYMWTRDSALVFKNIVDRFT      ETYDAGLQRRIEQYITAQVT  120
SEQ ID NO 12  AFGTSAGAVIASPSTTDPDY      YYMWTRDSALVFKNIVDRFT      ETYDAGLQRRIEQYIAAQVT  120
SEQ ID NO 13  AFGTSIGAVVASPSTTDPDY      FYMWTRDSALVFKTLVDRFT      QKYDAGLQRRIEQYIAAQVT  117
SEQ ID NO 14  AFGTSAGAVIASPSTTDPDY      YYMWTRDSALVFKNIVDRFT      EQYDAGLQRRIEQYITAQVT  120
SEQ ID NO 15  AFGTSAGAVIASPSTTDPDY      YYMWTRDSALVFKNLVDRFT      ETYDAGLQRRIEQYISAQVT  120
SEQ ID NO 16  AFGTSAGAVIASPSTTDPDY      YYMWTRDSALVFKNIVDRFT      QQYDAGLQRRIEQYISAQVT  120
SEQ ID NO 17  AFGTSAGAVIASPSTVDPDY      YYMWTRDSALVFKNIVDRFT      ETYDAGLQRRIEQYITAQVT  120
SEQ ID NO 18  AFGTSAGAVIASPSTTDPDY      YYMWTRDSALVFKNLVDRFT      QKYDAGLQRRIEQYIAAQVT  120
SEQ ID NO 19  AFGTSIGAVVASPSTTDPDY      FYMWTRDSALVFKTLVDRFT      QNYDAGLQRRIEQYIAAQVT  117
              ****  *  ********* ***   * ***************** *      *    ********** ****
```

FIG. 1B

| | | | | |
|---|---|---|---|---|
| SEQ ID NO 2 | LQGLSNPSGSLADGSGLGEP | KFELTLKPFTGNWGRPQRDG | PALRAIALIGYSKWLINNNY | 147 |
| SEQ ID NO 7 | LQGISNPSGSLADGSGLGEP | KFELTLNQFTGHWGRPQRDG | PALRAIALIGYSKWLIDNNY | 180 |
| SEQ ID NO 8 | LQGISNPSGSLSDGSGLGEP | KFELTLSQFTGNWGRPQRDG | PALRAIALIGYSKWLINNNY | 180 |
| SEQ ID NO 9 | LQGLTNPSGSLSDGSGLGEP | KFELTLQPFTGNWGRPQRDG | PALRAIALIGYAKWLINNNY | 180 |
| SEQ ID NO 10 | LQGPSNPSGSLSDGSGLGEP | KFELTLSQFTGNWGRPQRDG | PALRAIALIGYSKWLINNNY | 180 |
| SEQ ID NO 11 | LQGLSNPSGSLTDGSGLGEP | KFELTLQPFTGNWGRPQRDG | PALRAIALIGYSKWLINNNY | 180 |
| SEQ ID NO 12 | LQGLTNPSGSLSDGSGLGEP | KFELTLKPFTGNWGRPQRDG | PALRAIALIGYSKWLINNNY | 180 |
| SEQ ID NO 13 | LQGISNPSGSLSDGSGLGEP | KFELTLSQFTGNWGRPQRDG | PALRAIALIGYSKWLISNNY | 177 |
| SEQ ID NO 14 | LQGLSNPSGSLSDGSGLGEP | KFELTLSQFTGNWGRPQRDG | PALRAIALIGYSKWLINNNY | 180 |
| SEQ ID NO 15 | LQGLSNPSGSLTDGSGLGEP | KFELTLSQFTGNWGRPQRDG | PALRAVALIGYSKWLINNNY | 180 |
| SEQ ID NO 16 | LQGISNPSGSLADGSGLGEP | KFELTLKPFTGNWGRPQRDG | PALRAIALIGYSKWLINNNY | 180 |
| SEQ ID NO 17 | LQGLTNPSGSLSDGSGLGEP | KFELTLSPFTGNWGRPQRDG | PALRAIALIGYSKWLINNNY | 180 |
| SEQ ID NO 18 | LQGISNPSGSLSDGSGLGEP | KFELTLNQFTGNWGRPQRDG | PALRAIALIGYSKWLINNNY | 180 |
| SEQ ID NO 19 | LQGISNPSGSLSDGSGLGEP | KFELTLSQFTGNWGRPQRDG | PALRAIALIGYSKWLISNNY | 177 |
| | :*** ***** ******** | ***** ***** ******* | ****** ******* :*** | |
| | | | | |
| SEQ ID NO 2 | QSTVSNVIWPIVRNDLNYVA | QYWNQTGFDLWEEVNGSSFF | TVANQHRALVEGATLAATLG | 207 |
| SEQ ID NO 7 | QSTVSDIIWPILRNDLNYVA | QYWNQTGFDLWEEVEGSSFF | TVANQHRALVEGATLAAILG | 240 |
| SEQ ID NO 8 | QSTVSNIIWPIVRNDLNYVA | QYWNQTGFDLWEEVNGSSFF | TVANQHRALVEGATLAATLG | 240 |
| SEQ ID NO 9 | QSTVSSVIWPIVRNDLNYVA | QYWNQTGFDLWEEVDGSSFF | TVANQHRALVEGATLVATLG | 240 |
| SEQ ID NO 10 | QSTVSSIIWPIVRNDLNYVA | QYWNQTGFDLWEEVKGSSFF | TIANQHRALVEGATLAATLG | 240 |
| SEQ ID NO 11 | QSTVSSLIWPIVRNDLNYVA | QYWNQTGFDLWEEVNGSSFF | TTANQHRALVEGATLAATLS | 240 |
| SEQ ID NO 12 | QSTVSNIIWPIVRNDLNYVA | QYWNQTGFDLWEEVNGSSFF | AVANQHRALVEGATLATTLG | 237 |
| SEQ ID NO 13 | QSTVSNIIWPIVRNDLNYVA | QYWNQTGFDLWEEVNGSSFF | TVANQHRALVEGATLAATLG | 240 |
| SEQ ID NO 14 | QSTVSNVIWPIVRNDLNYVA | QYWNQTGFDLWEEVNGSSFF | TMANQHRALVEGATLAATLG | 240 |
| SEQ ID NO 15 | QSTVSNIIWPIVRNDLNYVA | QYWNQTGFDLWEEVNGSSFF | TVANQHRALVEGATLAATLG | 240 |
| SEQ ID NO 16 | QSTVSNVIWPIVRNDLSYAA | QYWNQTGFDLWEEVSGSSFF | TVANQHRALVEGATLAATLG | 240 |
| SEQ ID NO 17 | QSTVSSVIWPIVRNDLNYVA | QYWNQTGFDLWEEVNGSSFF | TVANQHRALVEGATLATTLG | 240 |
| SEQ ID NO 18 | QSTVSNIIWPIVKNDLNYVA | QYWNQTGFDLWEEVNGSSFF | TVANQHRALVEGATLATTLG | 240 |
| SEQ ID NO 19 | QSTVSNIIWPIVRNDLNYVA | QYWNQTGFDLWEEVNGSSFF | TVANQHRALVEGATLATTLG | 237 |
| | :* *:* *:*: | **************** | **************:* | |

FIG. 1C

| | | | | | |
|---|---|---|---|---|---|
| SEQ ID NO 2 | QSGSAYSSVAPQVLCFLQRF | WVSSGGYVDSNINTNEGRTG | KDVNSVLTSIHTFDPNLGCD | | 267 |
| SEQ ID NO 7 | QSGSSYSAVAPQILCFLQKF | WVSSGGYVNSNINSDINRTG | KDANSLLASIHTFDPSIGCD | | 300 |
| SEQ ID NO 8 | QSGSTYSSVAPQILCFLQRF | WVS-GGYIDSNINTNEGRTG | KDANSILTSIHTFDPSLGCD | | 299 |
| SEQ ID NO 9 | QSGDTYSSVAPQVLCFLQRF | WVSSGGYIDSNINTNEGRTG | KDANSILTSIHTFDPSLGCD | | 300 |
| SEQ ID NO 10 | QSGSTYSSVAPQILCFLQRF | WVS-GGYIDSNINTNSNDGRTG | KDANSLLASIHTFDPSLGCD | | 299 |
| SEQ ID NO 11 | QSGSTYSSVAPQILCFLQRF | WVSSGGYVDSNINTNEGRTG | KDVNSILTSIHTLDPNLGCD | | 300 |
| SEQ ID NO 12 | QPASTYSSVAPQILCFLQRY | WVSSGGYVDSNINTNEGRTG | KDANSILAAIHTFDPNLGRD | | 300 |
| SEQ ID NO 13 | QSGSSYSSVAPQILCFLQKF | WSP-SGYVISNINSNDGRTG | KDSNSILTSIHTFDPSIGCD | | 296 |
| SEQ ID NO 14 | QSGSTYSSVAPQILCFLQRF | WVS-GGYIDSNINTNEGRTG | KDANSLLASIHTFDPSLGCD | | 299 |
| SEQ ID NO 15 | QSGSTYSSVAPQILCFLQRF | WVSSGGYVDSNINTNEGRTG | KDVNSVLTSIHTFDPNLGCD | | 300 |
| SEQ ID NO 16 | QSGSTYSSVAPQILCFLQRF | WVS-GGYIDSNINTNEGRTG | KDANSLLASIHTFDPSLGCD | | 299 |
| SEQ ID NO 17 | QSGSTYSSVAPQILCFLQRF | WVSSGGYVDSNINTNEGRTG | KDVNSILTSIHTFDPNLGCD | | 300 |
| SEQ ID NO 18 | QSGSTYSSVAPQILCFLQRF | WVS-GSYIDSNINVNEGRTG | KDANSLLASIHTFDPSLGCD | | 299 |
| SEQ ID NO 19 | QSGSSYSTVAPQILCFLQKF | WSP-SGYVISNINSNDGRTG | KDSNSILTSIHTFDPSIGCD | | 296 |
| | * ***** ****** | * * * **** | ** ** *** * | | |

| | | | | | |
|---|---|---|---|---|---|
| SEQ ID NO 2 | AGTFQPCSDKALSNLKVVVD | SFRSIYGVNKGIPAGAAVAI | GRYAEDVYYNGNPWYLATFA | | 327 |
| SEQ ID NO 7 | PATFQPCSDKALSNLKSVVD | SFRSIYGVNQGISAGSAVAI | GRYSEDVYFNGNPWYLATFA | | 360 |
| SEQ ID NO 8 | ASTFQPCSDKALSNLKVVVD | SFRSIYGVNKGIPAGSAVAI | GRYPEDVYFNGNPWYLATFA | | 359 |
| SEQ ID NO 9 | AGTFQPCSDKALSNLKVVVD | SFRSIYSLNKGIPAGAAVAI | GRYPEDVYFNGNPWYLATFA | | 360 |
| SEQ ID NO 10 | ASTFQPCSDKALSNLKVVVD | SFRSIYGVNKGISAGSAVAI | GRYPEDVYFNGNPWYLATFA | | 359 |
| SEQ ID NO 11 | AGTFQPCSDKALSNLKVVVD | SFRSIYGVNKGIPAGAAVAI | GRYAEDVYFNGNPWYLATFA | | 360 |
| SEQ ID NO 12 | AGTFQPCSDKALSNLKVVVD | SFRSIYGVNKGIPAGAAVAV | GRYPEDVYFNGNPWYLATFA | | 360 |
| SEQ ID NO 13 | AATFQPCSDKALSNLKVYVD | SFRSIYSVNKGIPAGAAVAV | GRYPEDVYFNGNPWYLSTFA | | 356 |
| SEQ ID NO 14 | ASTFQPCSDKALSNLKVVVD | SFRSIYGVNKGIPAGAAVAI | GRYPEDVYFNGNPWYLATFA | | 359 |
| SEQ ID NO 15 | AATFQPCSDKALSNFKVVVD | SFRSIYGVNKGIPAGSAVAI | GRYAEDVYFNGNPWYLATFA | | 360 |
| SEQ ID NO 16 | ASTFQPCSDKALSNLKVVVD | SFRSIYGVNNGIPAGAAVAI | GRYPEDVYFNGNPWYLATFA | | 359 |
| SEQ ID NO 17 | AGTFQPCSDKALSNLKVVVD | SFRSIYGVNKGIPAGAAVAI | GRYPEDVYFNGNPWYLATFA | | 360 |
| SEQ ID NO 18 | ASTFQPCSDKALSNLKVVVD | SFRSIYGVNSGISASSAVAI | GRYPEDVYFNGNPWYLATFA | | 359 |
| SEQ ID NO 19 | AATFQPCSDKALSNLKVYVD | SFRSIYGVNSGIPAGTAVAV | GRYPEDVYFNGNPWYLSTFA | | 356 |
| | * ************ * | ****** * * * * | *** *** ****** ** | | |

FIG. 1D

| | | | | | |
|---|---|---|---|---|---|
| SEQ ID NO 2 | AAEQLYDAIYVWKKTGSITV | TATSLAFFQELVPGVTAGTY | SSSSS-TFTNIINAVSTYAD | 386 |
| SEQ ID NO 7 | AAEQLYDSLYVWKQTGSITV | TAIPLAFFQELVPGVAAGTY | LSSQS-TFTSIVNAVSAYAD | 419 |
| SEQ ID NO 8 | AAEQLYDSVYVWKKTGSITV | TSTSSAFFQELVPGVAAGTY | SSSQS-TFTSIINAISTYAD | 418 |
| SEQ ID NO 9 | AAEQLYDAVYVWKETGSITV | TATSLAFFQELVPGVTAGTY | SSSSSTFTTIINAVSTYAD | 420 |
| SEQ ID NO 10 | AAEQLYDSVYVWKKTGSITV | TSTSLAFFQELVPGVAAGTY | SSSQS-TFTSIVNAVSTYAD | 418 |
| SEQ ID NO 11 | AAEQLYDAVYVWKKTGSITV | TATSLAFFQELVPGVAAGTY | ASSSS-TFTNIINAVSTYAD | 419 |
| SEQ ID NO 12 | AAEQLYDAIYVWKKTGSITV | TAISLAFFQELVPGVAAGTY | SSSQS-TFTNIINAVSTYAD | 419 |
| SEQ ID NO 13 | VAEQLYDAIYVWKKTGSITV | TSTSLAFFQELVPSVTAGTY | ASSSS-TFTSIVNAVSTYAD | 415 |
| SEQ ID NO 14 | AAEQLYDSVYVWKKTGSITV | TSTSLAFFQELVPGVAAGTY | SSSQS-TFTSIINAVSTYAD | 418 |
| SEQ ID NO 15 | AAEQLYDAIYVWKKTGSITV | TATSLAFFQELVPGVAAGTY | ASSSS-TFTSIINAVSTYAD | 419 |
| SEQ ID NO 16 | AAEQLYDSVYVWKKTGSITV | TSTSLAFFQELVPGVAAGTY | SSSQS-TFTSIINAVSTYAD | 418 |
| SEQ ID NO 17 | AAEQLYDAIYVWKKTGSITV | TAISLAFFQELVPGVTAGTY | SSSQS-TFTNIINAASTYAD | 419 |
| SEQ ID NO 18 | AAEQLYDALYVWKQAGSITV | TSTSLAFFQQLVPGVAAGTY | SSSQS-TYTSIINAVSAYAD | 418 |
| SEQ ID NO 19 | VAEQLYDALYVWKKTGSITV | TSTSLAFFQELVPSVTAGTY | ASSSS-TFTSIVNAVSTYAD | 415 |
| | ****** ** ** ****** | * *** *** * ***** | * * ** ** *** |

| | | | | | |
|---|---|---|---|---|---|
| SEQ ID NO 2 | GFLSEAAKYVPADGSLAEQF | DRNSGTPLSALHLTWSYASF | LTATARRAGIVPPSWANSSA | 446 |
| SEQ ID NO 7 | GFLNEAAKYVPSDGSLAEQF | DKNNGTPLSAVHLTWSYASF | LTATARRAGSVPPSWANSNA | 479 |
| SEQ ID NO 8 | GFLSEAAKYVPADGSLAEQF | DRNTGTPLSAVHLTWSYASF | LTAAARRAGVVPPSWASSGA | 478 |
| SEQ ID NO 9 | GFLSEAAKYVPADGSLAEQF | DRNNGTALSARHLTWSYASF | LTATARRAGVVPPSWASSGA | 480 |
| SEQ ID NO 10 | GFLSEAAKYVPADGSLAEQF | DRNTGTPLSAVHLTWSYASF | LTATARRAGIVPPSWANSSA | 478 |
| SEQ ID NO 11 | GFLSEAAKYVPADGSLAEQF | DRNSGTPLSALHLTWSYASF | FTAAARRSGVVPPSWANSSA | 479 |
| SEQ ID NO 12 | GFISEAAKYVPADGSLAEQF | DRNNGTPLSALHLTWSYASF | LTATARRAGIVPPSWANSSA | 479 |
| SEQ ID NO 13 | GFVSEAAKYVPSDGSLAEQF | DKNTGTPLSAVHLTWSYASF | LTATRRAGIVPPSWISSGA | 475 |
| SEQ ID NO 14 | GFLSEAAKYVPADGSLAEQF | DRNTGTPLSAVHLTWSYASF | LTATTRRAGIVPPSWASSGA | 478 |
| SEQ ID NO 15 | GFLSEAAKYVPADGSLAEQF | DRNSGTPLSALHLTWSYASF | LTAAARRAGVVPPSWANSSA | 479 |
| SEQ ID NO 16 | GFLSEAAKYVPADGSLAEQF | DRNTGTPLSAVHLTWSYASF | LTAAARRAGVVPPSWASSGA | 478 |
| SEQ ID NO 17 | GFVTEAAKYVPTDGSLAEQF | DRNNGTPLSAVHLTWSYASF | LTASARRAGVVPPSWANSSA | 479 |
| SEQ ID NO 18 | GFMNEAAKYVPADGSLAEQF | DKNSGTPLSAVHLTWSYASF | LTAADRRAGIVPSSWASSGA | 478 |
| SEQ ID NO 19 | GFVSEAAKYVPSDGSLSEQF | DKNTGTPLSAVHLTWSYASF | LTATARRAGIVPPSWISSGA | 475 |
| | ** ****** * ** *** | * * ** ** ******** | * ** ** * * |

FIG. 1E

```
SEQ ID NO 2    STIPSTCSGASVVGSYSRPT ATSFPPSQTPKPGVPSGTPY TPLPCATPTSVAVTFHELVS  506
SEQ ID NO 7    TSIPTACSGTSVVGSYSSPT ATSFPPSQTPKVGKPTGTPF TPIPCATPTSVAVTFHELPT  539
SEQ ID NO 8    NTVPSSCSGASVVGSYSRPT ATSFPPSQTPKPGVPSGTPF TPIPCATPTSVAVTFHELAT  538
SEQ ID NO 9    STIPSTCSGASVVGSYSRPT ATSFPPSQTPKPGVPSGTPY TPLPCATPTSVAVTFHELVS  540
SEQ ID NO 10   NSIPATCSGASVVGSYSSPT ATSFPPSQTPKPGVPSGTPF TPLPCATPTSVAVTFHELAT  538
SEQ ID NO 11   STIPSTCSGASVVGSYSRPT ATSFPPSQTPKPGVPSGTPY TPLPCATPTSVAVTFHELVS  539
SEQ ID NO 12   SSIPSTCSGASVVGSYSRPT ATSFPPSQTPKPGVPSGTPY TPLPCATPTSVAVTFHELVS  539
SEQ ID NO 13   NTVPSSCSGTTVAGSYSSPT ATSFPPSQTPKT-AATGTSF TPIACATPTSVAVTFHELAT  534
SEQ ID NO 14   NSVPSSCSGASVVGSYSRPT ATSFPPSQTPKPGAPSGAPF TPIPCATPASVAVTFHELAT  538
SEQ ID NO 15   STIPSTCSGASVVGSYSRPT ATSFPPSQTPKPGVPSGTPY TPLPCATPTSVAVTFHELVS  539
SEQ ID NO 16   NSVPSSCSGASVVGSYSRPT ATSFPPSQTPKPGVPSGTPF TPIPCATPTSVAVTFHELAT  538
SEQ ID NO 17   SSISSTCSGASVVGSYSSPT ATSFPPSQTPKPGVPSGTPY TPLPCATPTSVAVTFHELVS  539
SEQ ID NO 18   NTVPSSCSGASVVGSYSRPT ATSFPPSQTPKPGVPSGTPF TPIPCATPTSVAVTFHELAT  538
SEQ ID NO 19   NTVPSSCSGTTVAGSYSSPT ATSFPPSQTPKT-AATGTSF TPIACATPTSVAVTFHELAT  534
               ***  *  *  ***** **  ***************  *     ** ****** **********

SEQ ID NO 2    TQFGQTVKVAGNAAALGNWS TSAAVALDAVNYADNHPLWI GTVNLEAGDVVEYKYINVGQ  566
SEQ ID NO 7    TQFGQTIKLAGSAEEALGNWS TGAAVGLDAANYASNHPLWF GTLNLQAGDVIEYKYINVGK  599
SEQ ID NO 8    TQFGQTIKVAGSAPELGNWS TSAAIALDAVNYATNHPLWI GSVNLEAGDVIEYKYINVGQ  598
SEQ ID NO 9    TQFGQTVKVAGSAQALGNWS TSAAVALDAVNYADNHPLWI GTVNLEAGDVVEYKYINVGQ  600
SEQ ID NO 10   TQFGQNIKVAGSAPELGNWS TSAAVALDAVNYATNHPLWI GSVNLEAGDVIEYKYINVGQ  598
SEQ ID NO 11   TQLGQTVKVAGNAPALGNWS TSAAVALDAVNYADNHPLWI GTVDLEAGDVVEYKYINVGQ  599
SEQ ID NO 12   TQLGQTVKVAGSAPALGNWS TSAAVALDAVNYADNHPLWI GSVELEAGDVVEYKYINVGQ  599
SEQ ID NO 13   TVPGQTIKVVGNAQALGNWS TSAGVALNAVNCASNHPLWI GPVNLKAGDVVEYKYINVGS  594
SEQ ID NO 14   TQFGQTVKVAGSAPELGNWS TSAAIALDAVNYATNHPLWI GSVNLEAGDVIEYKYINVGQ  598
SEQ ID NO 15   TQFGQTVKVAGNAPALGNWS ASAAVALDAINYADNHPLWI GTVDLEAGDVIEYKYISVGQ  599
SEQ ID NO 16   TQFGQTIKVAGSAPELGNWS TSAAIALDAVNYATNHPLWI GSVSLEAGDVIEYKYINVGQ  598
SEQ ID NO 17   TQFGQTVKAAGSAPALGNWS TNAAVALNAVNYASNHPLWL GTVELEAGDVVEYVQYKYINVGS  599
SEQ ID NO 18   TQFGQTIKVVGSVPELGNWS TSAGVALNAVNYASNHPLWI GSINLAAGEVVQYKYINVGS  598
SEQ ID NO 19   TVPGQTIKVVGNAQALGNWS TSAGVALNAVNYASNHPLWI GPVNLKAGDVVEYKYINVGS  594
               * ** *  * *     **** *    **  **  ****  *  *  *** ***  **
```

FIG. 1F

```
SEQ ID NO 2   DGSVTWESDPNHTYTVPAVA CVTQVVKEDTWQS 599
SEQ ID NO 7   DGSVTWESDPNHTYTVPAVA CVTEVVKEDTWQS 632
SEQ ID NO 8   DGSVTWESDPNHTYTVPAVA CVTEVVKEDTWQS 631
SEQ ID NO 9   DGSVTWESDPNHTYTVPAVA CVTQVVKEDTWQS 633
SEQ ID NO 10  DGSVTWESDPNHTYTVPAVA CVTEVVKEDTWQS 631
SEQ ID NO 11  DGSVTWESDPNHTYTVPAVA CVTQVVKEDTWQS 632
SEQ ID NO 12  DGSVTWESDPNHTYTVPAVA CVTQVVKEDTWQS 632
SEQ ID NO 13  DGSVTWEADPNHTYTVPAVA CVTAVVKEDTWQS 627
SEQ ID NO 14  DGSVTWESDPNHTYTVPAVA CVTEVVKEDTWQS 631
SEQ ID NO 15  DGSVTWESDPNHTYTVPAVA CVTQVVKEDTWQS 632
SEQ ID NO 16  DGSVTWESDPNHTYTVPAVA CVTEVVKEDTWQS 631
SEQ ID NO 17  DGSVTWESDPNHTYTVPAVA CVTEVVKEDTWQS 632
SEQ ID NO 18  DGSVTWESDPNHTYTVPAVA CVTQVVKEDTWQS 631
SEQ ID NO 19  DGSVTWEADPNHTYTVPAVA CVTAVVKEDTWQS 627
              ******* ************ *** *********
```

TrGA's catalytic domain: ▢ residues 1-453 of SEQ ID NO: 2
TrGA's linker: ▨ residues 454-490 of SEQ ID NO: 2
TrGA's starch binding domain: ▦ residues 491-599 of SEQ ID NO: 2

TRICHODERMA REESEI GLUCOAMYLASE VARIANTS RESISTANT TO OXIDATION-RELATED ACTIVITY LOSS AND THE USE THEREOF

CROSS-REFERENCE TO RELATED APPLICATIONS

This application is a U.S. National Phase Application of International Application No. PCT/US2013/054462, filed Aug. 12, 2013, which claims benefit to U.S. Provisional patent application 61/683,007, filed on Aug. 14, 2012, the contents of which are hereby incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "40045-US-PCT_ST25.txt" created on Sep. 8, 2015, which is 98,304 bytes in size.

FIELD

*Trichoderma reesei* glucoamylase (TrGA) variants are useful in starch processing, for example, producing alcohol as an end product through a simultaneous saccharification and fermentation (SSF) process. Compositions comprising the TrGA variants and methods of using the TrGA variants in starch processing are provided.

BACKGROUND

Industrial fermentations predominately use glucose as a feedstock for the production of a multitude of proteins, enzymes, alcohols, and other chemical end products. Typically, glucose is the product of starch processing, which is conventionally a two-step, enzymatic process that catalyzes the breakdown of starch, involving liquefaction and saccharification. During liquefaction, insoluble granular starch is slurried in water, gelatinized with heat, and hydrolyzed by a thermostable alpha-amylase. During saccharification, the soluble dextrins produced in liquefaction are further hydrolyzed by glucoamylases.

Glucoamylase enzymes (glucan 1,4-α-glucohydrolases, EC 3.2.1.3) are starch hydrolyzing exo-acting carbohydrases, which catalyze the removal of successive glucose units from the non-reducing ends of starch or related oligo- and polysaccharide molecules. Glucoamylases can hydrolyze both the linear and branched glucosidic linkages of starch (e.g., amylose and amylopectin). Glucoamylases are commercially important enzymes and have been used in a wide variety of applications that require the hydrolysis of starch. For example, glucoamylases are typically used to produce fermentable sugars from the enzyme liquefied starch substrate. The fermentable sugars, e.g., low-molecular-weight sugars, such as glucose, may then be 1) converted to fructose by other enzymes (e.g., glucose isomerases); 2) crystallized; or 3) used in fermentations to produce numerous end products (e.g., alcohols, monosodium glutamate, succinic acid, vitamins, amino acids, 1,3-propanediol, and lactic acid). Fermentation and saccharification can be conducted simultaneously (i.e., an SSF process) to achieve greater economy and efficiency.

Glucoamylases have been used successfully in commercial applications for many years. Additionally, various mutations have been introduced in fungal glucoamylases, for example, *Trichoderma reesei* glucoamylase (TrGA), to enhance thermal stability and specific activity. See, e.g., WO 2008/045489; WO 2009/048487; WO 2009/048488; and U.S. Pat. No. 8,058,033. The need still exists for providing new glucoamylase variants with more desirable properties.

SUMMARY

CS4, a *Trichoderma reesei* glucoamylase (TrGA) variant having the amino acid sequence of SEQ ID NO: 5, has been previously disclosed in U.S. Pat. No. 8,058,033. CS4 was obtained by introducing the five substitutions (L417V, T430A, Q511H, A539R, and N563I) into TrGA having the amino acid sequence of SEQ ID NO: 2. Compared with the parent TrGA, CS4 exhibits improved properties, e.g., both increased thermostability and increased specific activity. Nevertheless, both TrGA and CS4 were found to have a reduced activity after longer term storage. In some instances, this loss of activity has been attributed amongst others to the oxidization of the M50 residue of the enzymes. Substitution of the methionine residue at position 50 (M50) of CS4 by glycine (G), phenylalanine (F), lysine (K), or tyrosine (Y) results in variants resistant to oxidation-related activity loss. Among these variants, the one carrying the M50Y substitution exhibits equivalent performance to CS4 in both SSF end product yield and DP4+ hydrolysis efficiency. Accordingly, this TrGA variant, encompassing the substitutions of M50Y, L417V, T430A, Q511H, A539R, and N563I of SEQ ID NO: 2, would be advantageously useful in various starch processing applications.

The present disclosure relates to a glucoamylase variant (1) having at least 90%, 95%, 97%, or 99% sequence identity with SEQ ID NO: 2, and (2) comprising amino acid substitutions corresponding to positions: 50, 417, 430, 511, 539, and 563 of SEQ ID NO: 2, or corresponding positions in a parent glucoamylase. In one aspect, the glucoamylase variant has the amino acid substitution of M50Y, G, F, or K at position 50 of SEQ ID NO: 2, or the corresponding position in a parent glucoamylase. In another aspect, the glucoamylase variant has the amino acid substitution of M50Y at position 50 of SEQ ID NO: 2, or the corresponding position in a parent glucoamylase. In yet another aspect, the amino acid substitutions at positions 417, 430, 511, 539, and 563 of the glucoamylase variant are: L417V, T430A, Q511H, A539R, and N563I, respectively.

In one embodiment, the glucoamylase variant comprises the amino acid sequence of SEQ ID NO: 6. In another embodiment, the glucoamylase variant consists of the amino acid sequence of SEQ ID NO: 6.

In one embodiment, the glucoamylase variant may further comprise one or more additional amino acid substitutions corresponding to positions: 43, 44, 61, 73, 294, 431, 503, or 535 of SEQ ID NO: 2, or a corresponding position in the parent glucoamylase. In another embodiment, the glucoamylase variant may comprise one or more of the following amino acid substitutions: I43Q/R, D44C/R, N61I, G73F, G294C, A431L/Q, E503A/V, and/or A535R of SEQ ID NO: 2, or an equivalent position in the parent glucoamylase.

In one aspect, the glucoamylase variant may exhibit increased thermostability or increased specific activity as compared to the parent glucoamylase. In another aspect, the glucoamylase, loses less activity upon oxidation, when compared to a second glucoamylase variant comprising the amino acid sequence of SEQ ID NO: 5 under the same conditions.

An enzyme composition comprising the glucoamylase variant is provided. The enzyme composition may further comprise a hexokinase, a xylanase, a glucose isomerase, a xylose isomerase, a phosphatase, a phytase, a pullulanase, a β-amylase, an α-amylase, a protease, a cellulase, a hemicellulase, a lipase, a cutinase, a trehalase, an isoamylase, a redox enzyme, an esterase, a transferase, a pectinase, a lyase, an α-glucosidase, a β-glucosidase, other hydrolases, or a combination thereof.

Also provided is a method of processing starch comprising contacting a starch substrate with the glucoamylase variant to produce a composition comprising glucose. The method may further comprise adding a hexokinase, a xylanase, a glucose isomerase, a xylose isomerase, a phosphatase, a phytase, a pullulanase, a β-amylase, an α-amylase, a protease, a cellulase, a hemicellulase, a lipase, a cutinase, a trehalase, an isoamylase, a redox enzyme, an esterase, a transferase, a pectinase, an alpha-glucosidase, an beta-glucosidase, other hydrolases, or a combination thereof to the starch substrate.

In one aspect, the starch substrate is from wheat, barley, corn, rye, rice, sorghum, bran, cassava, milo, millet, potato, sweet potato, tapioca, and any combination thereof. In another aspect, the starch substrate is liquefied starch, gelatinized starch, or granular starch. In a further aspect, the starch substrate is about 15% to 50%, about 15% to 30%, or about 15% to 25%.

In one embodiment, saccharifying the starch substrate results in a high glucose syrup. In another embodiment, the method further comprises fermenting the fermentable sugars to an end product. The end product can be alcohol, or optionally ethanol. The end product also can be organic acids, amino acids, biofuels, and other biochemicals, including, but not limited to, ethanol, citric acid, lactic acid, succinic acid, monosodium glutamate, gluconic acid, sodium gluconate, calcium gluconate, potassium gluconate, itaconic acid and other carboxylic acids, glucono deltalactone, sodium erythorbate, lysine, omega 3 fatty acid, butanol, isoprene, 1,3-propanediol, and biodiesel). In another embodiment, saccharifying and fermenting are carried out as a simultaneous saccharification and fermentation (SSF) process.

In one embodiment, the contemplated glucoamylase variant is dosed at a range of about 0.1 to about 2.0, about 0.2 to about 1.0, or about 0.2 to about 0.5, or about 0.325 GAU per gram of dry solids. In another embodiment, saccharifying further comprises adding a hexokinase, a xylanase, a glucose isomerase, a xylose isomerase, a phosphatase, a phytase, a pullulanase, a β-amylase, an α-amylase, a protease, a cellulase, a hemicellulase, a lipase, a cutinase, a trehalase, an isoamylase, a redox enzyme, an esterase, a transferase, a pectinase, an alpha-glucosidase, an beta-glucosidase, or a combination thereof.

BRIEF DESCRIPTION OF THE DRAWINGS

The accompanying drawings are incorporated into the specification and provide non-limiting illustrations of various embodiments. In the drawings:

FIGS. 1A-1F depict a ClustalW alignment of the mature TrGA (SEQ ID NO: 2) with the full-length glucoamylases from several members of the *Trichoderma/Hypocrea* family cluster. The full-length glucoamylases are from *Hypocrea citrine* var. *americana* (SEQ ID NO: 7; see also SEQ ID NO: 6 of U.S. Pat. No. 7,413,879); *Hypocrea vinosa* (SEQ ID NO: 8; see also SEQ ID NO: 8 of U.S. Pat. No. 7,413,879); *Trichoderma* sp. (SEQ ID NO: 9; see also SEQ ID NO: 10 of U.S. Pat. No. 7,413,879); *Hypocrea gelatinosa* (SEQ ID NO: 10; see also SEQ ID NO: 12 of U.S. Pat. No. 7,413, 879); *Hypocrea orientalis* (SEQ ID NO: 11; see also SEQ ID NO: 14 of U.S. Pat. No. 7,413,879); *Trichoderma konilangbra* (SEQ ID NO: 12; see also SEQ ID NO: 16 of U.S. Pat. No. 7,413,879); *Trichoderma* sp. (SEQ ID NO: 13; see also SEQ ID NO: 29 of U.S. Pat. No. 7,413,879); *Trichoderma harzianum* (SEQ ID NO: 14; see also SEQ ID NO: 31 of U.S. Pat. No. 7,413,879); *Trichoderma longibrachiatum* (SEQ ID NO: 15; SEQ ID NO: 33 of U.S. Pat. No. 7,413,879); *Trichoderma asperellum* (SEQ ID NO: 16; see also SEQ ID NO: 35 of U.S. Pat. No. 7,413,879); *Trichoderma strictipilis* (SEQ ID NO: 17; see also SEQ ID NO: 37 of U.S. Pat. No. 7,413,879); *Trichoderma virens* Gv29-8 (SEQ ID NO: 18; see also GenBank Accession No. EHK25059.1); and *Trichoderma atroviride* IMI 206040 (SEQ ID NO: 19; see also GenBank Accession No. EHK49034.1). Residues designated by an asterisk in FIG. 1 are TrGA residues corresponding to conserved residues in SEQ ID NOs: 7-19. The contemplated amino acid residues for substitutions are in bold. TrGA's catalytic domain, linker region, and starch binding domain are indicated with various bars.

DETAILED DESCRIPTION

Figure 2:
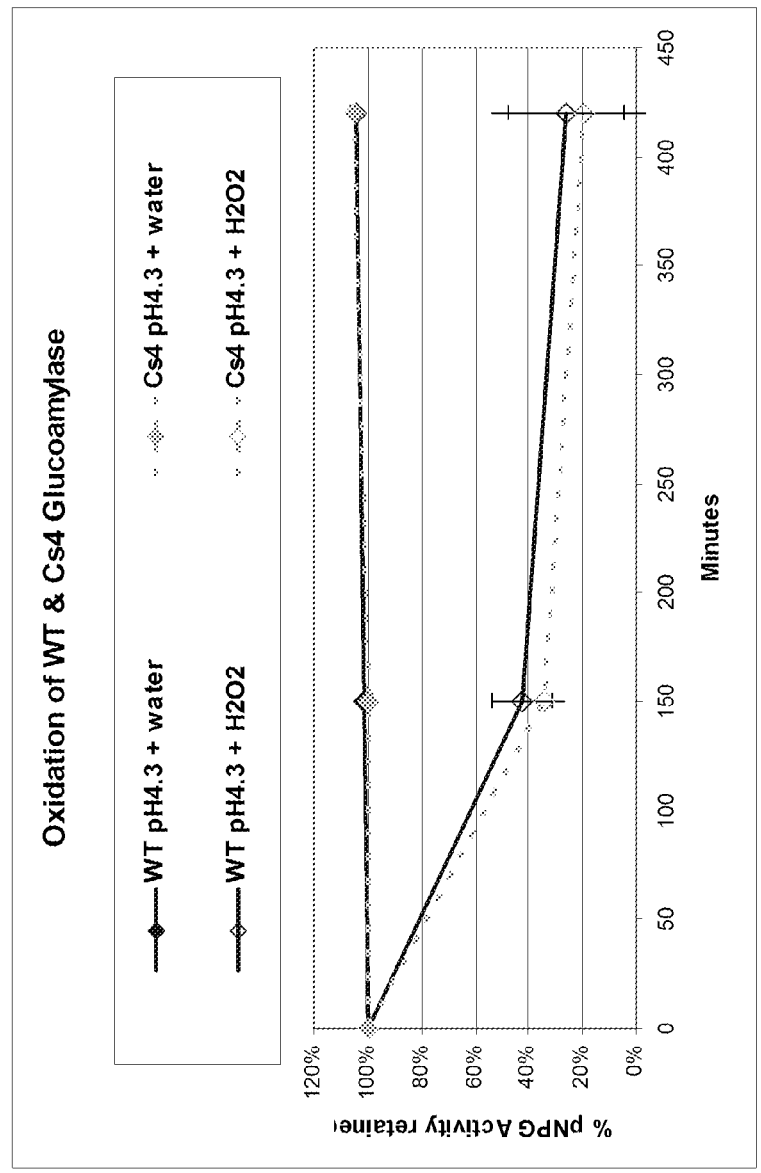
FIG. 2 depicts the retained pNPG activity for TrGA (WT) and the CS4 variant at various time points upon hydrogen peroxide treatment. The experiments were performed as described in Example 1, at pH 4.3.

The present disclosure relates to a glucoamylase variant having an amino acid sequence identity of at least 90%, 91%, 92%, 93%, 94%, 95%, 96%, 97%, 98%, or 99% to TrGA (SEQ ID NO: 2). The glucoamylase variant comprises amino acid substitutions corresponding to positions: 50, 417, 430, 511, 539, and 563 of SEQ ID NO: 2, or corresponding positions in a parent glucoamylase. The amino acid substitution at position 50 is M50Y, G, F, or K, while the amino acid substitutions at positions 417, 430, 511, 539, and 563 are L417V, T430A, Q511H, A539R, and N563I. The glucoamylase variant may display increased thermostability and/or increased specific activity as compared to the parent glucoamylase. The glucoamylase variant, when compared with a second glucoamylase variant comprising the amino acid sequence of SEQ ID NO: 5, may lose less activity upon oxidation. The glucoamylase variant can be included in an enzyme mix for various starch processing applications. Exemplary applications for the glucoamylase variant are in a process of starch saccharification, e.g., the production of a high glucose syrup, and the production of an end product through fermentation or SSF.

In some aspects, the embodiments of the present disclosure rely on routine techniques and methods used in the field of genetic engineering and molecular biology. The following resources include descriptions of general methodology useful in accordance with the embodiments: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994). Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the representative methods and materials are described. Numeric ranges are inclusive of the numbers defining the range. The headings provided herein are not limitations of the various aspects or embodiments, which can be had by reference to the specification as a whole.

1. DEFINITIONS AND ABBREVIATIONS

In accordance with this detailed description, the following abbreviations and definitions apply. It should be noted that as used herein, the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

Unless defined otherwise, all technical and scientific terms used herein have the same meaning as commonly understood by one of ordinary skill in the art. The following terms are provided below.

1.1. DEFINITIONS

As used herein, "amino acid sequence" is synonymous with the term "polypeptide" and/or the term "protein." In some instances, the term "amino acid sequence" is synonymous with the term "peptide"; in some instances, the term "amino acid sequence" is synonymous with the term "enzyme."

As used herein, "nucleotide sequence" or "nucleic acid sequence" refers to a sequence of genomic, synthetic, or recombinant origin and may be double-stranded or single-stranded, whether representing the sense or anti-sense strand. As used herein, the term "nucleic acid" may refer to genomic DNA, cDNA, synthetic DNA, or RNA. The residues of a nucleic acid may contain any of the chemical modifications commonly known and used in the art.

"Isolated" means that the material is at least substantially free from at least one other component that the material is naturally associated with.

"Purified" means that the material is in a relatively pure state, e.g., at least about 80% pure, at least about 90% pure, at least about 95% pure, at least about 98% pure, or even at least about 99% pure.

"Oligosaccharide" means a carbohydrate molecule composed of 3-20 monosaccharides.

As used herein, "transformed cell" includes cells that have been transformed by use of recombinant DNA techniques. Transformation typically occurs by insertion of one or more nucleotide sequences into a cell. The inserted nucleotide sequence may be a heterologous nucleotide sequence, i.e., is a sequence that may not be natural to the cell that is to be transformed, such as a nucleotide sequence encoding a fusion protein.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide. Generally, "operably linked" means that the DNA sequences being linked are contiguous, and, in the case of a secretory leader, contiguous and in reading phase.

As used herein, "starch" refers to any material comprised of the complex polysaccharide carbohydrates of plants, comprised of amylose and amylopectin with the formula $(C_6H_{10}O_5)_x$, wherein "X" can be any number. The term includes plant-based materials such as grains, grasses, tubers and roots, and more specifically materials obtained from wheat, barley, corn, rye, rice, sorghum, bran, cassava, milo, millet, potato, sweet potato, and tapioca. The term "starch" includes granular starch. The term "granular starch" refers to raw, i.e., uncooked starch, e.g., starch that has not been subject to gelatinization.

As used herein, "starch gelatinization" means solubilization of a starch molecule to form a viscous suspension.

As used herein, "gelatinization temperature" refers to the lowest temperature at which gelatinization of a starch substrate occurs. The exact temperature depends upon the specific starch substrate and further may depend on the particular variety and the growth conditions of plant species from which the starch is obtained.

"DE" or "dextrose equivalent" is an industry standard for measuring the concentration of total reducing sugars, calculated as the percentage of the total solids that have been converted to reducing sugars. The granular starch that has not been hydrolyzed has a DE that is about zero (0), and D-glucose has a DE of about 100.

As used herein, "starch substrate" refers to granular starch or liquefied starch obtained using refined starch, whole ground grains, or fractionated grains.

As used herein, "liquefied starch" refers to starch that has gone through solubilization process, for example, the conventional starch liquefaction process.

As used herein, "glucose syrup" refers to an aqueous composition containing glucose solids. Glucose syrup will have a DE of at least about 20. In some embodiments, glucose syrup may contain no more than about 21% water while at least about 25% reducing sugar calculated as dextrose. In one embodiment, glucose syrup may include at least about 90% D-glucose, and in another embodiment, glucose syrup may include at least about 95% D-glucose. In some embodiments, the terms "glucose" and "glucose syrup" are used interchangeably.

"Degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose.

As used herein, "fermentable sugars" refer to saccharides that can be metabolized under fermentation conditions.

These sugars typically refer to glucose, maltose, and maltotriose (DP1, DP2 and DP3).

As used herein, "total sugar content" refers to the total sugar content present in a starch composition.

As used herein, "dry solids" (DS or ds) refers to the total solids of a slurry in a dry weight percent basis. The term "slurry" refers to an aqueous mixture containing insoluble solids.

As used herein, "starch-liquefying enzyme" refers to an enzyme that catalyzes the hydrolysis or breakdown of a starch polymer. Exemplary starch liquefying enzymes include alpha-amylases (EC 3.2.1.1).

"Amylase" means an enzyme that is, among other things, capable of catalyzing the degradation of starch.

"Alpha-amylases (EC 3.2.1.1)" refer to endo-acting enzymes that cleave α-D-(1→4) O-glycosidic linkages within the starch molecule in a random fashion. In contrast, the exo-acting amylolytic enzymes, such as beta-amylases (EC 3.2.1.2; α-D-(1→4)-glucan maltohydrolase) and some product-specific amylases like maltogenic alpha-amylase (EC 3.2.1.133) cleave the starch molecule from the non-reducing end of the substrate. These enzymes have also been described as those effecting the exo- or endohydrolysis of 1,4-α-D-glucosidic linkages in polysaccharides containing 1,4-α-linked D-glucose units. Another term used to describe these enzymes is glycogenase. Exemplary enzymes include alpha-1,4-glucan 4-glucanohydrolase.

As used herein, "glucoamylases" refer to the amyloglucosidase class of enzymes (EC 3.2.1.3, glucoamylase, α-1,4-D-glucan glucohydrolase). These are exo-acting enzymes that release glucosyl residues from the non-reducing ends of amylose and/or amylopectin molecules. The enzymes are also capable of hydrolyzing α-1,6 and α-1,3 linkages, however, at much slower rates than the hydrolysis of α-1,4 linkages.

As used herein, "maximum activity" refers to the enzyme activity measured under the most favorable conditions, for example, at an optimum pH. As used herein, "optimum pH" refers to a pH value, under which the enzyme displays the highest activity with other conditions being equal.

As used herein, "prosequence" refers to the amino acid sequence between the signal sequence and mature protein that is necessary for the secretion of the protein. Cleavage of the prosequence will result in a mature active protein.

The phrase "mature form" of a protein or polypeptide refers to the final functional form of the protein or polypeptide derived from its precursor. For example, a mature form of a glucoamylase has its signal peptide cleaved. A mature form of a glucoamylase may be produced from its native host, for example, by endogenous expression. Alternatively, a mature form of a glucoamylase may be produced from a non-native host, for example, by exogenous expression. An exogenously expressed glucoamylase, while maintaining the glucoamylase activity, may have a varied glycosylation pattern compared to the endogenous expressed counterpart.

The term "parent" or "parent sequence" refers to a sequence that is native or naturally occurring in a host cell.

The term "Trichoderma/Hypocrea family cluster" refers to a member of the Family Hypocreaceae including several anamorphs as Trichoderma and Gliocladium of the Order Hypocreales, Phylum Ascomycota. See Chapter 12, Alexopoulos, C. J., et al., in INTRODUCTION MYCOLOGY 4th Edition, John Wiley & Sons, NY 1996.

As used herein, the terms "variant" is used in reference to glucoamylases that have some degree of amino acid sequence identity to a parent glucoamylase sequence. A variant is similar to a parent sequence, but has at least one substitution, deletion, or insertion in their amino acid sequence that makes them different in sequence from a parent glucoamylase. In some cases, variants have been manipulated and/or engineered to include at least one substitution, deletion, or insertion in their amino acid sequence that makes them different in sequence from a parent. Additionally, a glucoamylase variant may retain the functional characteristics of the parent glucoamylase, e.g., maintaining a glucoamylase activity that is at least about 50%, about 60%, about 70%, about 80%, or about 90% of that of the parent glucoamylase.

The terms "thermostable" and "thermostability," with reference to an enzyme, refer to the ability of the enzyme to retain activity after exposure to an elevated temperature. The thermostability of an enzyme, such as an amylase enzyme, can be measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

As used herein, "hydrolysis of starch" refers to the cleavage of glucosidic bonds with the addition of water molecules.

As used herein, "no-cook" refers to a process of converting a granular starch substrate, for example, raw starch, to fermentable sugars without the conventional high-temperature starch liquefaction process.

As used herein, "end product" or "desired end product" refers to a molecule or compound that a starch substrate is converted into, by an enzyme and/or a microorganism.

As used herein, "contacting" or "admixing" refers to the placing of the respective enzyme(s) in sufficiently close proximity to the respective substrate to enable the enzyme(s) to convert the substrate to the end product. Those skilled in the art will recognize that mixing solutions of the enzyme with the respective substrates can affect contacting or admixing.

"Percent sequence identity" means that a variant has at least a certain percentage of amino acid residues identical to a reference sequence, when aligned using the CLUSTAL W algorithm with default parameters. See Thompson et al. (1994) *Nucleic Acids Res.* 22:4673-4680. Default parameters for the CLUSTAL W algorithm are:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty | OFF. |

Deletions are counted as non-identical residues, compared to a reference sequence. Deletions occurring at either termini are included. For example, a variant with five amino acid deletions of the C-terminus of the mature TrGA polypeptide of SEQ ID NO: 2 would have a percent sequence identity of 99% (594/599 identical residues×100, rounded to the nearest whole number) relative to the mature polypeptide. Such a variant would be encompassed by a variant having "at least 99% sequence identity" to a mature TrGA polypeptide.

The phrase "simultaneous saccharification and fermentation (SSF)" refers to a process in the production of biochemicals in which a microbial organism, such as an ethanologenic microorganism, and at least one enzyme, such as the presently contemplated glucoamylase variant, are present during the same process step. SSF includes the contemporaneous hydrolysis of starch substrates (granular, treated at a temperature below gelatinization, liquefied, or solubilized) to saccharides, including glucose, and the fermentation of the saccharides into alcohol or other biochemical or biomaterial in the same reactor vessel.

The term "fermented beverage" refers to any beverage produced by a method comprising a fermentation process, such as a microbial fermentation, e.g., a bacterial and/or yeast fermentation.

"Beer" is an example of such a fermented beverage, and the term "beer" is meant to comprise any fermented wort produced by fermentation/brewing of a starch-containing plant material. Often, beer is produced exclusively from malt or adjunct, or any combination of malt and adjunct. Examples of beers include: full malted beer, beer brewed under the "Reinheitsgebot," ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

The term "malt" refers to any malted cereal grain, such as malted barley or wheat.

The term "adjunct" refers to any starch and/or sugar containing plant material that is not malt, such as barley or wheat malt. Examples of adjuncts include common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like.

The term "mash" refers to an aqueous slurry of any starch and/or sugar containing plant material, such as grist, e.g., comprising crushed barley malt, crushed barley, and/or other adjunct or a combination thereof, mixed with water later to be separated into wort and spent grains.

The term "wort" refers to the unfermented liquor run-off following extracting the grist during mashing.

1.2. ABBREVIATIONS

The following abbreviations apply unless indicated otherwise:

ABTS 2,2'-Azino-bis(3-ethylbenzothiazoline-6-sulfonic acid) diammonium salt
AkAA *Aspergillus kawachii* alpha-amylase
AmyE *Bacillus subtilis* alpha-amylase
AmyL *Bacillus licheniformis* alpha-amylase
AmyR SPEZYME® XTRA amylase
AmyS *Geobacillus stearothermophilus* alpha-amylase
AnGA *Aspergillus niger* glucoamylase
BAA bacterial alpha-amylase
cDNA complementary DNA
CHCA α-cyano-4-hydroxycinnamic acid
DE Dextrose Equivalent
DI distilled, deionized
DNA deoxyribonucleic acid
DPn degree of polymerization with n subunits
DS or ds dry solids
DTT dithiothreitol
EC enzyme commission for enzyme classification
ESI/MS Electrospray Ionization/Mass Spectrometry
FA formic acid
g gram
GAU glucoamylase units
HPLC high pressure liquid chromatography
IAA iodoacetamide
kg kilogram
LC/MS Liquid Chromatography/Mass Spectrometry
MALDI-TOF Matrix-assisted Laser Desorption Ionization-Time-of-Flight
MOPS 3-(N-morpholino)propanesulfonic acid
MRM Multiple Reaction Monitoring
MT metric ton
MtP microtiter plate
MW molecular weight
NCBI National Center for Biotechnology Information
nm nanometer
OD optical density
PCR polymerase chain reaction
PEG polyethylene glycol
PI performance index
ppm parts per million
RNA ribonucleic acid
RO reverse osmosis
RP reversed-phase
rpm revolutions per minute
SSF simultaneous saccharification and fermentation
TCA trichloroacetic acid
TrGA *Trichoderma reesei* glucoamylase
w/v weight/volume
w/w weight/weight
wt wild-type
μL or μl microliter

2. ENZYMES IN STARCH PROCESSING

2.1. *Trichoderma reesei* Glucoamylase (TrGA) and Variants Thereof

Commercially, glucoamylases are very important enzymes and have been used in a wide variety of applications that require the hydrolysis of starch (e.g., for producing glucose and other monosaccharides from starch). Glucoamylases are used to produce high fructose corn sweeteners, which comprise over 50% of the sweetener market in the United States. In general, glucoamylases may be, and commonly are, used with alpha-amylases in starch hydrolyzing processes to hydrolyze starch to dextrins and then glucose. The glucose may then be converted to fructose by other enzymes (e.g., glucose isomerases); crystallized; or used in fermentations to produce numerous end products (e.g., organic acids, amino acids, biofuels, and other biochemicals, including, but not limited to, ethanol, citric acid, lactic acid, succinic acid, monosodium glutamate, gluconic acid, sodium gluconate, calcium gluconate, potassium gluconate, itaconic acid and other carboxylic acids, glucono delta-lactone, sodium erythorbate, lysine, omega 3 fatty acid, butanol, isoprene, 1,3-propanediol, and biodiesel).

Glucoamylases are produced by numerous strains of bacteria, fungi, yeast, and plants. Many fungal glucoamylases are extracellularly produced by the hosts, for example from strains of *Aspergillus* (Svensson et al., *Carlsberg Res. Commun.* 48: 529-544 (1983); Boel et al., *EMBO J.* 3: 1097-1102 (1984); Hayashida et al., *Agric. Biol. Chem.* 53:

923-929 (1989); U.S. Pat. No. 5,024,941; U.S. Pat. No. 4,794,175 and WO 1988/09795); *Talaromyces* (U.S. Pat. No. 4,247,637; U.S. Pat. No. 6,255,084; and U.S. Pat. No. 6,620,924); *Rhizopus* (Ashikari et al., *Agric. Biol. Chem.* 50: 957-964 (1986); Ashikari et al., *App. Microbio. Biotech.* 32: 129-133 (1989) and U.S. Pat. No. 4,863,864); *Humicola* (WO 2005/052148 and U.S. Pat. No. 4,618,579); and *Mucor* (Houghton-Larsen et al., *Appl. Microbiol. Biotechnol.* 62: 210-217 (2003)). Many of the genes that code for these enzymes have been cloned and expressed in yeast, fungal, and/or bacterial cells.

Fungal glucoamylases consist of as many as three distinct structural domains: a catalytic domain that is structurally conserved in all glucoamylases, generally followed by a linker region that is connected to a starch binding domain. The glucoamylase from *Trichoderma reesei* QM6a (ATCC, Accession No. 13631) (TrGA) has been known and characterized. TrGA comprises the amino acid sequence of SEQ ID NO: 2, which is described in U.S. Pat. No. 7,413,879, for example. The cDNA sequence encoding the TrGA from *Trichoderma reesei* QM6a is presented as SEQ ID NO: 4. The native TrGA has the amino acid sequence of SEQ ID NO: 1, which includes (1) a signal peptide containing 20 amino acid residues (SEQ ID NO: 3, positions 1 to 20 of SEQ ID NO: 1), and (2) a prosequence containing 13 amino acid residues (positions 21-33 of SEQ ID NO: 1). Cleavage of the signal peptide and the prosequence results in the mature TrGA having the amino acid sequence of SEQ ID NO: 2. As shown in FIG. 1, the catalytic domain of TrGA includes residues 1-453 of SEQ ID NO: 2, the linker domain of TrGA spans residues 454-490 of SEQ ID NO: 2, and the starch binding domain of TrGA encompasses residues 491-599 of SEQ ID NO: 2.

The structure of TrGA was determined to 1.8 Angstrom resolution. See WO 2009/048488 and WO 2009/048487. Using the determined coordinates, the structure was aligned with the coordinates of the catalytic domain of the glucoamylase from *Aspergillus awamori* strain×100 that was determined previously (Aleshin, A. E., Hoffman, C., Firsov, L. M., and Honzatko, R. B. Refined crystal structures of glucoamylase from *Aspergillus awamori* var.×100. *J. Mol. Biol.* 238: 575-591 (1994)). See id. The structures of the catalytic domains of these two glucoamylases overlap very closely, and it is possible to identify equivalent residues based on this structural superposition. See id. It is further believed that all glucoamylases share the basic structure. See id.

As disclosed in U.S. Pat. No. 8,058,033, one or more amino acid substitutions at the following positions of TrGA (SEQ ID NO: 2) may result in variants having improved thermostability and/or improved specific activity: 4, 5, 12, 24, 29, 43, 44, 45, 46, 47, 49, 51, 61, 70, 73, 75, 76, 94, 100, 108, 114, 116, 119, 122, 124, 125, 137, 143, 146, 148, 169, 171, 172, 175, 178, 180, 181, 208, 211, 228, 242, 243, 245, 292, 294, 297, 309, 310, 313, 314, 315, 316, 317, 321, 340, 341, 350, 353, 356, 363, 368, 369, 375, 376, 395, 398, 401,408, 409, 412, 415, 417, 418, 421,430, 431,433, 436, 451, 503, 511, 535, 539, and/or 563. The substitutions can be, for example, D4L/E/R/S/C/A/Q/W, F5C/M/N/R/S/T/V/W, I12L/R, D24E/L/Y/T, F29L/I/D/C/S/V/W, I43F/R/D/Y/S/Q, D44E/H/K/S/N/Y/F/R/C, Y47W, Y49N, N61D/I/L/Q/V/W, Q70R/K/M/P/G/L/F, G73F/C/L/W, Q75R/K/A, R76L/M/K/T/P, P94L, D100W/I/Q/M/P/A/N, N119P/T/Y/D/E, N146S/G/C/H/E/D/T/W/L/F/M, Q148V/Y/H/A/C/D/G/M/R/S/T, Y169D/F, Q172C/A/D/R/E/F/HN/L/M/N/S/T/V, F175H/A/G/R/S/T/C/W/Y, W178A/C/D/E/F/G/H/K/N/R/S/T/V/Y, E180A/C/G/H/I/L/N/P/Q/R/S/T/V/Y/, V181E/C/D/ G/H/I/P/T/Y/S/L/K/F/A, Q208L/A/C/E/N/F/H/T, S211C/R/E/A/Y/W/M/H/L/I/R/Q/T, E243S/R/N/M/Y/A/L, R245A/E/M/I/P/V, I292D/H/P/R/T/N/V/F/L, G294C/D/E/T/Q/I/A, K297F/L/P/T/M/D/N/Q/A/Y/H/S/R/W, R309A/C/G/H/I/N/P/Q/S/T/W/Y/L, Y310E/G/L/P/S/W/R/Q, D313Q, V314A/R/N/D/C/E/Q/G/H/I/L/K/M/F/P/S/T/W/Y, Y315F, Y316Q/R, N317T/H, K340D/T, K341F/D/P/V/G/S, T350S/E/A/N, Q356H/D/E, T363L/R/C/H/W, S368W/D/F/L, S369F, N376Q/T/H/S/V, Y395Q/R/S, A398S/I/T, S401C/V, R408S, N409W/T/K, T412A/H/K/G, L417A/D/E/F/G/I/K/Q/R/S/T/V/W/Y, T430A/E/F/G/H/I/K/M/N/Q/R/V, A431C/E/H/I/L/M/Q/R/S/W/Y, R433H/Q, I436A/T, S451M/T/H, E503A/C/D/H/S/V/W, Q511C/G/H/I/K/T/V, A535E/F/G/K/L/N/P/R/S/T/V/W/Y, A539E/H/M/R/S/W, and/or N563/A/C/E/I/K/L/Q/T/V. Among the above positions, positions 43, 44, 61, 73, 294, 417, 430, 431, 503, 511, 535, 539, and 563, appear more attractive, because most of them were identified by screening in a *Trichoderma reesei* host. One of the TrGA variants disclosed in U.S. Pat. No. 8,058,033 is CS4 (L417V+T430A+Q511H+A539R+N563I). CS4 displays both improved thermostability (having a PI of 1.95 over TrGA) and improved specific activity (having a PI of at least 1.21 over TrGA).

The presently contemplated glucoamylase variants may have an amino acid sequence identity of at least 90%, 91%, 92%, 93%, 94%, 95%, 96%, 97%, 98%, or 99% to TrGA (SEQ ID NO: 2). The contemplated glucoamylase variant comprises amino acid substitutions corresponding to positions: 50, 417, 430, 511, 539, and 563 of SEQ ID NO: 2, or corresponding positions in a parent glucoamylase. The amino acid substitution at position 50 is M50Y, G, F, or K, while the amino acid substitutions at positions 417, 430, 511, 539, and 563 are L417V, T430A, Q511H, A539R, and N563I. The glucoamylase variant may display increased thermostability and/improved specific activity as compared to the parent glucoamylase. The glucoamylase variant may lose less activity upon oxidation, when compared with a second glucoamylase variant comprising the amino acid sequence of SEQ ID NO: 5 under the same conditions.

FIG. 1 shows a ClustalW alignment of the mature TrGA (SEQ ID NO: 2) with the full-length glucoamylases from several members of the *Trichoderma/Hypocrea* family cluster. These full-length glucoamylases include those from

*Hypocrea citrine* var. *americana* (SEQ ID NO: 7);
*Hypocrea vinosa* (SEQ ID NO: 8);
*Trichoderma* sp. (SEQ ID NO: 9);
*Hypocrea gelatinosa* (SEQ ID NO: 10);
*Hypocrea orientalis* (SEQ ID NO: 11);
*Trichoderma konilangbra* (SEQ ID NO: 12);
*Trichoderma* sp. (SEQ ID NO: 13);
*Trichoderma harzianum* (SEQ ID NO: 14);
*Trichoderma longibrachiatum* (SEQ ID NO: 15);
*Trichoderma asperellum* (SEQ ID NO: 16);
*Trichoderma strictipilis* (SEQ ID NO: 17);
*Trichoderma virens* Gv29-8 (SEQ ID NO: 18); and
*Trichoderma atroviride* IMI 206040 (SEQ ID NO: 19);

each of which has at least 90% sequence identity to SEQ ID NO: 2. The alignments shown in FIG. 1 and the structural relationships ascertained from the crystal structures of TrGA and *A. awamori* glucoamylase, for example, can guide the construction of the presently contemplated glucoamylase variants. Variant glucoamylases include, but are not limited to, those with an amino acid modification selected from a substitution, insertion, or deletion of a corresponding amino acid in SEQ ID NO: 7, 8, 9, 10, 11, 12, 13, 14, 15, 16, 17, 18, and/or 19, in addition to the contemplated substitutions at positions 50, 417, 430, 511, 539, and 563 of SEQ ID NO:

2, or corresponding positions in a parent glucoamylase. Correspondence between positions in TrGA and glucoamylases of SEQ ID NO: 7-19 is determined with reference to the alignment shown in FIG. 1. The contemplated glucoamylase variants may also include, but are not limited to, those with 1, 2, 3, 4, 5, or 6 randomly selected amino acid modifications. Amino acid modifications can be made using well-known methodologies, such as oligo-directed mutagenesis.

2.2. Production of Glucoamylase

The contemplated glucoamylase variants may be produced using recombinant DNA technology in various host cells. In some embodiments, the host cells are selected from bacterial, fungal, plant and yeast cells. The term "host cell" includes both the cells, progeny of the cells and protoplasts created from the cells that are used to produce a variant glucoamylase according to the disclosure. In some embodiments, the host cells are fungal cells and typically filamentous fungal host cells. The term "filamentous fungi" refers to all filamentous forms of the subdivision Eumycotina (See Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi of the present disclosure are morphologically, physiologically, and genetically distinct from yeasts. Vegetative growth by filamentous fungi is by hyphal elongation and carbon catabolism is obligatory aerobic. In the embodiments of the present disclosure, the filamentous fungal parent cell may be a cell of a species of, but not limited to, *Trichoderma*, (e.g., *Trichoderma reesei*, the asexual morph of *Hypocrea jecorina*, previously classified as *T. longibrachiatum*, *Trichoderma viride*, *Trichoderma koningii*, *Trichoderma harzianum*) (Sheir-Neirs et al., (1984) Appl. Microbiol. Biotechnol 20:46-53; ATCC No. 56765 and ATCC No. 26921); *Penicillium* sp., *Humicola* sp. (e.g., *H. insolens*, *H. lanuginosa* and *H. grisea*); *Chrysosporium* sp. (e.g., *C. lucknowense*), *Gliocladium* sp., *Aspergillus* sp. (e.g., *A. oryzae*, *A. niger*, *A sojae*, *A. japonicus*, *A. nidulans*, and *A. awamori*) (Ward et al., (1993) Appl. Microbiol. Biotechnol. 39:738-743 and Goedegebuur et al., (2002) Genet 41:89-98), *Fusarium* sp. (e.g., *F. roseum*, *F. graminum*, *F. cerealis*, *F. oxysporuim*, and *F. venenatum*), *Neurospora* sp. (*N. crassa*), *Hypocrea* sp., *Mucor* sp. (*M. miehei*), *Rhizopus* sp. and *Emericella* sp. (see also Innis et al., (1985) Sci. 228: 21-26). The term "*Trichoderma*" or "*Trichoderma* sp." or "*Trichoderma* spp." refers to any fungal genus previously or currently classified as *Trichoderma*. In other embodiments, the host cell will be a genetically engineered host cell wherein native genes have been inactivated, for example by deletion in fungal cells. Where it is desired to obtain a fungal host cell having one or more inactivated genes, known methods may be used (e.g. methods disclosed in U.S. Pat. Nos. 5,246,853 and 5,475,101, and WO 1992/06209). Gene inactivation may be accomplished by complete or partial deletion, by insertional inactivation or by any other means that renders a gene nonfunctional for its intended purpose (such that the gene is prevented from expression of a functional protein). In some embodiments, when the host cell is a *Trichoderma* cell and particularly a *T. reesei* host cell, the cbh1, cbh2, egl1 and egl2 genes may be inactivated and/or typically deleted. Typically, *Trichoderma reesei* host cells having quad-deleted proteins are set forth and described in U.S. Pat. No. 5,847,276 and WO 2005/001036. In other embodiments, the host cell is a protease deficient or protease minus strain.

To produce the contemplated glucoamylase variants using the recombinant DNA technology, a DNA construct comprising nucleic acid encoding the amino acid sequence of the designated glucoamylase can be constructed and transferred into, for example, a *Trichoderma reesei* host cell. The vector may be any vector which when introduced into a *Trichoderma reesei* host cell can be integrated into the host cell genome and can be replicated. Reference is made to the Fungal Genetics Stock Center Catalogue of Strains (FGSC, <www.fgsc.net>) for a list of vectors. Additional examples of suitable expression and/or integration vectors are provided in Sambrook et al., (1989) supra, and Ausubel (1987) supra, and van den Hondel et al. (1991) in Bennett and Lasure (Eds.) MORE GENE MANIPULATIONS IN FUNGI, Academic Press pp. 396 428 and U.S. Pat. No. 5,874,276. The nucleic acid encoding the glucoamylase can be operably linked to a suitable promoter, which shows transcriptional activity in *Trichoderma reesei* host cell. The promoter may be derived from genes encoding proteins either homologous or heterologous to the host cell. Suitable non-limiting examples of promoters include cbh1, cbh2, egl1, egl2. In one embodiment, the promoter may be a native *T. reesei* promoter. Typically, the promoter can be *T. reesei* cbh1, which is an inducible promoter and has been deposited in GenBank under Accession No. D86235. An "inducible promoter" may refer to a promoter that is active under environmental or developmental regulation. In another embodiment, the promoter can be one that is heterologous to *T. reesei* host cell. Other examples of useful promoters include promoters from *A. awamori* and *A. niger* glucoamylase genes (see, e.g., Nunberg et al., (1984) Mol. Cell Biol. 4:2306-2315 and Boel et al., (1984) *EMBO J*. 3:1581-1585). Also, the promoters of the *T. reesei* xln1 gene and the cellobiohydrolase 1 gene (cbh1) can be used (EP 137280).

In some embodiments, the glucoamylase coding sequence can be operably linked to a signal sequence. The signal sequence may be the native signal peptide of the glucoamylase (SEQ ID NO: 3, which represents residues 1-20 of SEQ ID NO: 1, the full-length native TrGA, for example). Alternatively, the signal sequence may have at least 90% or at least 95% sequence identity to the native signal sequence. In additional embodiments, a signal sequence and a promoter sequence comprising a DNA construct or vector to be introduced into the *T. reesei* host cell are derived from the same source. For example, in some embodiments, the signal sequence can be the cbh1 signal sequence that is operably linked to a cbh1 promoter.

In some embodiments, the expression vector may also include a termination sequence. In one embodiment, the termination sequence and the promoter sequence can be derived from the same source. In another embodiment, the termination sequence can be homologous to the host cell. A particularly suitable terminator sequence can be cbh1 derived from *T. reesei*. Other exemplary fungal terminators include the terminator from *A. niger* or *A. awamori* glucoamylase gene.

In some embodiments, an expression vector may include a selectable marker. Examples of representative selectable markers include ones that confer antimicrobial resistance (e.g., hygromycin and phleomycin). Nutritional selective markers also find use in the present invention including those markers known in the art as amdS, argB, and pyr4. Markers useful in vector systems for transformation of *Trichoderma* are known in the art (see, e.g., Finkelstein, chapter 6 in BIOTECHNOLOGY OF FILAMENTOUS FUNGI, Finkelstein et al. Eds. Butterworth-Heinemann, Boston, Mass. (1992), Chap. 6; and Kinghorn et al. (1992) APPLIED MOLECULAR GENETICS OF FILAMENTOUS FUNGI, Blackie Academic and Professional, Chapman and Hall, London). In a representative embodiment, the selective marker may be the amdS gene, which encodes the enzyme acetamidase, allowing transformed cells to grow on acetamide as a nitrogen source. The use of *A. nidulans* amdS gene as a selective marker is described for example in Kelley et al., (1985) *EMBO J.* 4:475-479 and Penttila et al., (1987) *Gene* 61:155-164.

An expression vector comprising a DNA construct with a polynucleotide encoding the glucoamylase may be any vector which is capable of replicating autonomously in a given fungal host organism or of integrating into the DNA of the host. In some embodiments, the expression vector can be a plasmid. In typical embodiments, two types of expression vectors for obtaining expression of genes also are contemplated.

The first expression vector may comprise DNA sequences in which the promoter, glucoamylase-coding region, and terminator all originate from the gene to be expressed. In some embodiments, gene truncation can be obtained by deleting undesired DNA sequences (e.g., DNA encoding unwanted domains) to leave the domain to be expressed under control of its own transcriptional and translational regulatory sequences.

The second type of expression vector may be preassembled and contains sequences needed for high-level transcription and a selectable marker. In some embodiments, the coding region for the glucoamylase gene or part thereof can be inserted into this general-purpose expression vector such that it is under the transcriptional control of the expression construct promoter and terminator sequences. In some embodiments, genes or part thereof may be inserted downstream of a strong promoter, such as the strong cbh1 promoter.

Methods used to ligate the DNA construct comprising a polynucleotide encoding the glucoamylase, a promoter, a terminator, and other sequences and to insert them into a suitable vector are well known in the art. Linking can be generally accomplished by ligation at convenient restriction sites. If such sites do not exist, the synthetic oligonucleotide linkers are used in accordance with conventional practice (see, Sambrook (1989) supra, and Bennett and Lasure, MORE GENE MANIPULATIONS IN FUNGI, Academic Press, San Diego (1991) pp 70-76). Additionally, vectors can be constructed using known recombination techniques (e.g., Invitrogen Life Technologies, Gateway Technology).

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (see, e.g., Ausubel et al., (1987), supra, chapter 9; and Sambrook (1989) supra, and Campbell et al., (1989) *Curr. Genet.* 16:53-56). The expression of heterologous protein in *Trichoderma* is described in U.S. Pat. Nos. 6,022,725; 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "The Molecular Biology of *Trichoderma* and its Application to the Expression of Both Homologous and Heterologous Genes," in MOLECULAR INDUSTRIAL MYCOLOGY, Eds. Leong and Berka, Marcel Dekker Inc., NY (1992) pp. 129-148).

In some embodiments, genetically stable transformants can be constructed with vector systems whereby the nucleic acid encoding glucoamylase is stably integrated into a host strain chromosome. Transformants can then be purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability can be conducted by growing the transformants on solid non-selective medium (i.e., medium that lacks acetamide), harvesting spores from this culture medium and determining the percentage of these spores which subsequently germinate and grow on selective medium containing acetamide. Alternatively, other methods known in the art may be used to select transformants.

Uptake of DNA into the host *Trichoderma* sp. strain is dependent upon the calcium ion concentration. Generally, between about 10 mM $CaCl_2$ and 50 mM $CaCl_2$ may be used in an uptake solution. Besides the need for the calcium ion in the uptake solution, other compounds generally included are a buffering system such as TE buffer (10 mM Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes, thus permitting the contents of the medium to be delivered into the cytoplasm of the *Trichoderma* sp. strain and the plasmid DNA is transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL, typically, $2\times10^6$/mL are used in transformation. A volume of 100 μL of these protoplasts or cells in an appropriate solution (e.g., 1.2 M sorbitol; 50 mM $CaCl_2$) are mixed with the desired DNA. Generally, a high concentration of PEG may be added to the uptake solution. From 0.1 to 1 volume of 25% PEG 4000 can be added to the protoplast suspension. It is also typical to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. See, e.g., U.S. Pat. Nos. 6,022,725 and 6,268,328.

Generally, the mixture can be then incubated at approximately 0° C. for a period of between 10 to 30 minutes. Additional PEG may then be added to the mixture to further enhance the uptake of the desired gene or DNA sequence. The 25% PEG 4000 can be generally added in volumes of 5 to 15 times the volume of the transformation mixture; however, greater and lesser volumes may be suitable. The 25% PEG 4000 may be typically about 10 times the volume of the transformation mixture. After the PEG is added, the transformation mixture can then be incubated either at room temperature or on ice before the addition of a sorbitol and $CaCl_2$ solution. The protoplast suspension can then be further added to molten aliquots of a growth medium. This growth medium permits the growth of transformants only.

Generally, cells are cultured in a standard medium containing physiological salts and nutrients (see, e.g., Pourquie, J. et al., BIOCHEMISTRY AND GENETICS OF CELLULOSE DEGRADATION, eds. Aubert, J. P. et al., Academic Press, pp. 71 86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth also find use in the present embodiments.

Culture-conditions are also standard (e.g., cultures are incubated at approximately 28° C. in appropriate medium in shake cultures or fermentors until desired levels of glucoamylase expression are achieved). After fungal growth has been established, the cells are exposed to conditions effective to cause or permit the expression of the glucoamylase. In cases where the glucoamylase coding sequence is under the control of an inducible promoter, the inducing agent (e.g., a sugar, metal salt or antimicrobial), can be added to the medium at a concentration effective to induce glucoamylase expression.

In general, the glucoamylase produced in cell culture may be secreted into the medium and may be purified or isolated, e.g., by removing unwanted components from the cell culture medium. In some cases, the glucoamylase can be produced in an intracellular form, necessitating recovery from a cell lysate. In such cases, the enzyme may be purified from the cells in which it was produced using techniques routinely employed by those of skill in the art. Examples of these techniques include, but are not limited to, affinity chromatography (Tilbeurgh et a., (1984) *FEBS Lett.* 16: 215), ion-exchange chromatographic methods (Goyal et al., (1991) *Biores. Technol.* 36: 37; Fliess et al., (1983) *Eur. J. Appl. Microbiol. Biotechnol.* 17: 314; Bhikhabhai et al, (1984) *J. Appl. Biochem.* 6: 336; and Ellouz et al., (1987) *Chromatography* 396: 307), including ion-exchange using materials with high resolution power (Medve et al., (1998) *J. Chromatography A* 808: 153), hydrophobic interaction chromatography (see Tomaz and Queiroz, (1999) *J. Chromatography A* 865: 123; two-phase partitioning (see Brumbauer, et al., (1999) *Bioseparation* 7: 287); ethanol precipitation; reverse phase HPLC, chromatography on silica or on a cation-exchange resin such as DEAE, chromatofocusing, SDS-PAGE, ammonium sulfate precipitation, and gel filtration (e.g., Sephadex G-75).

2.3. Other Enzymes

In embodiments of the present disclosure, other enzyme(s) may be included in an enzyme composition comprising the contemplated glucoamylase variant. Additionally, other enzyme(s) may be supplemented to the contemplated glucoamylase variant in starch processing, for example, during saccharification and/or fermentation. These supplementary enzymes may include another glucoamylase, hexokinase, xylanase, glucose isomerase, xylose isomerase, phosphatase, phytase, pullulanase, β-amylase, α-amylase, protease, cellulase, hemicellulase, lipase, cutinase, trehalase, isoamylase, redox enzyme, esterase, transferase, pectinase, alpha-glucosidase, beta-glucosidase, lyase, or other hydrolases. See, e.g., WO 2009/099783. Skilled artisans in the art are well aware of the methods for obtaining and/or using the above-listed enzymes. For example, the contemplated glucoamylase variant and other enzyme(s) can be co-expressed, blended, or added separately in an application. The contemplated glucoamylase variant may also work synergistically with plant enzymes that are endogenously produced or genetically engineered. Additionally, the contemplated glucoamylase variant can work synergistically with endogenous, engineered, secreted, or non-secreted enzymes from a host producing the desired end product (e.g., organic acids, amino acids, biofuels, and other biochemicals, including, but not limited to, ethanol, citric acid, lactic acid, succinic acid, monosodium glutamate, gluconic acid, sodium gluconate, calcium gluconate, potassium gluconate, itaconic acid and other carboxylic acids, glucono delta-lactone, sodium erythorbate, lysine, omega 3 fatty acid, butanol, isoprene, 1,3-propanediol, and biodiesel). Furthermore, the host cells expressing the contemplated glucoamylase variant may produce biochemicals in addition to enzymes used to digest the various feedstock(s). Such host cells may be useful for fermentation or simultaneous saccharification and fermentation processes to reduce or eliminate the need to add enzymes.

2.4. Alpha-Amylases

Alpha-amylases constitute a group of enzymes present in microorganisms and tissues from animals and plants. They are capable of hydrolyzing alpha-1,4-glucosidic bonds of glycogen, starch, related polysaccharides, and some oligosaccharides. Although all alpha-amylases possess the same catalytic function, their amino acid sequences vary greatly. The sequence identity between different amylases can be virtually non-existent, e.g., falling below 25%. Despite considerable amino acid sequence variation, alpha-amylases share a common overall topological scheme that has been identified after the three-dimensional structures of alpha-amylases from different species have been determined. The common three-dimensional structure reveals three domains: (1) a "TIM" barrel known as domain A, (2) a long loop region known as domain B that is inserted within domain A, and (3) a region close to the C-terminus known as domain C that contains a characteristic beta-structure with a Greek-key motif.

Alpha-amylases commonly used for industrial applications include a group of homologous alpha-amylases produced by *Bacillus* spp., including *Bacillus licheniformis*, *Geobacillus stearothermophilus* (previously known as *Bacillus stearothermophilus*), *Bacillus amyloliquefaciens*, *Bacillus* sp. NCIB 12289, *Bacillus* sp. NCIB 12512, *Bacillus* sp. NCIB 12513, and *Bacillus* sp. DSM 9375, all of which are described in detail in U.S. Pat. No. 6,440,716 and WO 1995/26397. Useful alpha-amylases also include AmyE, an amylase from *Bacillus subtilis*, as well as fungal alpha amylases obtained from filamentous fungal strains such as *Aspergillus* (e.g., *A. niger, A. clavatus, A. kawachi*, and *A. oryzae*); *Trichoderma* sp., *Rhizopus* sp., *Mucor* sp., *Penicillium* sp., *Lactobacilli* sp., and *Streptomuces* sp.

2.5. Beta-Amylases

β-Amylases (EC 3.2.1.2) are exo-acting maltogenic amylases, which catalyze the hydrolysis of 1,4-α-glucosidic linkages into amylopectin and related glucose polymers, thereby releasing maltose. β-Amylases have been isolated from various plants and microorganisms. See Fogarty et al. (1979) in PROGRESS IN INDUSTRIAL MICROBIOLOGY, Vol. 15, pp. 112-115. These β-Amylases have optimum temperatures in the range from 40° C. to 65° C. and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Danisco US Inc.); and Novozym™ WBA (Novozymes A/S).

3. Starch Processing

3.1. Starch Substrates and Raw Materials

Those skilled in the art are well aware of available methods that may be used to prepare starch substrates for use in the processes disclosed herein. For example, a useful starch substrate may be obtained from tubers, roots, stems, legumes, cereals, or whole grain. More specifically, the granular starch comes from plants that produce high amounts of starch. For example, granular starch may be obtained from corn, wheat, barley, rye, milo, sago, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains about 70-72% starch. Specifically contemplated starch substrates are cornstarch, wheat starch, rye starch, sorghum starch, cassava starch, milo starch, millet starch, rice starch, bran starch, potato starch, sweet potato starch, tapioca starch, and barley starch. The starch from a grain may be ground or whole and includes corn solids, such as kernels, bran, and/or cobs. The starch may be highly refined raw starch or feedstock from starch refinery processes. Various starches also are commercially available. For example, cornstarch may be available from Cerestar, Sigma, and Katayama Chemical Industry Co. (Japan); wheat starch may be available from Sigma; sweet potato starch may be available from Wako Pure Chemical Industry Co. (Japan); and potato starch may be available from Nakaari Chemical Pharmaceutical Co. (Japan).

3.2. Milling

The starch substrate can be a crude starch from milled whole grain, which contains non-starch fractions, e.g., germ residues and fibers. Milling may comprise either wet milling or dry grinding. In wet milling, whole grain can be soaked in water or dilute acid to separate the grain into its component parts, e.g., starch, protein, germ, oil, kernel fibers. Wet milling efficiently separates the germ and meal (i.e., starch granules and protein) and can be especially suitable for production of syrups. In dry grinding, whole kernels are ground into a fine powder and processed without fractionating the grain into its component parts. Dry ground grain thus will comprise significant amounts of non-starch carbohydrate compounds, in addition to starch. Most ethanol comes from dry grinding. Alternatively, the starch to be processed may be a highly refined starch quality, for example, at least about 90%, at least about 95%, at least about 97%, or at least about 99.5% pure.

3.3. Gelatinization and Liquefaction

As used herein, the term "liquefaction" or "liquefy" means a process by which starch is converted to less viscous and soluble shorter chain dextrins. This process involves gelatinization of starch simultaneously with or followed by the addition of alpha-amylases. Additional liquefaction-inducing enzymes, e.g., a phytase, optionally may be added.

In some embodiments, the starch substrate prepared as described above may be slurried with water. The starch slurry may contain starch as a weight percent of dry solids of about 10-55%, about 20-45%, about 30-45%, about 30-40%, or about 30-35%. To optimize alpha-amylase stability and activity, the pH of the slurry may be adjusted to the optimal pH for the alpha-amylases. Alpha-amylases remaining in the slurry following liquefaction may be deactivated by lowering pH in a subsequent reaction step or by removing calcium from the slurry.

The slurry of starch plus the alpha-amylases may be pumped continuously through a jet cooker, which may be steam heated from about 85° C. to up to about 105° C. Gelatinization occurs very rapidly under these conditions, and the enzymatic activity, combined with the significant shear forces, begins the hydrolysis of the starch substrate. The residence time in the jet cooker can be very brief. The partly gelatinized starch may be passed into a series of holding tubes maintained at about 85-105° C. and held for about 5 min. to complete the gelatinization process. These tanks may contain baffles to discourage back mixing. As used herein, the term "secondary liquefaction" refers the liquefaction step subsequent to primary liquefaction, when the slurry is allowed to cool to room temperature. This cooling step can be about 30 minutes to about 180 minutes, e.g., about 90 minutes to 120 minutes. Milled and liquefied grain is also known as mash.

3.4. Saccharification

Following liquefaction, the mash can be further hydrolyzed through saccharification to produce fermentable sugars that can be readily used in the downstream applications. The saccharification of the present embodiments can be carried out by adding a glucoamylase variant as described above. The glucoamylase variant may be dosed at the range of about 0.1 to 2.0 GAU/g ds, about 0.2 to 1.0 GAU/g ds, about 0.2 to 0.5 GAU/g ds, or about 0.325 GAU/g ds. The saccharification may be performed at about 30 to about 60° C., or about 40 to about 60° C.

A full saccharification step may typically range 24 to 96 hours, 24 to 72 hours, or 24 to 48 hours. In some embodiments, the saccharification step and fermentation step are combined and the process is referred to as simultaneous saccharification and fermentation (SSF).

In some embodiments, the cooking step or exposure of the starch containing substrate to temperatures above the gelatinization temperate of the starch in the substrate may be eliminated. These fermentation processes can include milling of a cereal grain or fractionated grain and combining the ground cereal grain with liquid to form a slurry which is then mixed in a single vessel with the presently contemplated glucoamylase variant and optionally other enzymes such as, but not limited to, alpha amylases, other glucoamylases and enzymes having granular starch hydrolyzing activity or enhancing activity, and yeast to produce ethanol and other co-products or produce other biochemical using yeast or other production hosts. For example, there are enzymes or proteins that appear to enhance the activity of cellulases on cellulose (e.g., by oxidizing cellulose). In some cases, the yeast or other production hosts may also produce the glucoamylase and/or other enzymes. See, e.g., U.S. Pat. No. 4,514,496, WO 2004/081193, and WO 2004/080923.

3.5. Fermentation

In some embodiments of the present disclosure, the fermentable sugars may be subject to batch or continuous fermentation conditions. A classical batch fermentation is a closed system, wherein the composition of the medium is set at the beginning of the fermentation and is not subject to artificial alterations during the fermentation. Thus, at the beginning of the fermentation the medium may be inoculated with the desired organism(s). In this method, fermentation can be permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase, and finally to a stationary phase where growth rate is diminished or halted. If untreated, cells in the stationary phase eventually die. In general, cells in log phase are responsible for the bulk of production of the end product.

A variation on the standard batch system is the "fed-batch fermentation" system, which may be used in some embodiments of the present disclosure. In this variation of a typical batch system, the substrate can be added in increments as the fermentation progresses. Fed-batch systems are particularly useful when catabolite repression is apt to inhibit the metabolism of the cells and where it is desirable to have limited amounts of substrate in the medium. Measurement of the actual substrate concentration in fed-batch systems may be difficult and is therefore estimated on the basis of the changes of measurable factors such as pH, dissolved oxygen and the partial pressure of waste gases such as $CO_2$. Both batch and fed-batch fermentations are common and well known in the art.

On the other hand, continuous fermentation is an open system where a defined fermentation medium can be added continuously to a bioreactor and an equal amount of conditioned medium can be removed simultaneously for processing. Continuous fermentation generally maintains the cultures at a constant high density where cells are primarily in log phase growth. Continuous fermentation allows for the modulation of one factor or any number of factors that affect cell growth and/or end product concentration. For example, in one embodiment, a limiting nutrient such as the carbon source or nitrogen source can be maintained at a fixed rate while all other parameters are allowed to moderate. In other systems, a number of factors affecting growth can be altered continuously while the cell concentration, measured by media turbidity, may be kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are known in the art of industrial microbiology.

In further embodiments, by use of appropriate fermenting microorganisms as known in the art, the fermentation end product may include without limitation alcohol, ascorbic acid intermediates (e.g., gluconate; 2-keto-L-gulonic acid; 5-keto-gluconate; and 2,5-diketogluconate); 1,3-propanediol; aromatic amino acids (e.g., tyrosine, phenylalanine and tryptophan); organic acids (e.g., lactate, pyruvate, succinate, isocitrate, and oxaloacetate); amino acids (e.g., serine and glycine); antibiotics; antimicrobials; enzymes; vitamins; and hormones. See, e.g., WO 2008/086811 (methanol, ethanol, propanol, and butanol fermentation); WO 2003/066816, U.S. Pat. Nos. 5,254,467 and 6,303,352 (1,3-propanediol fermentation); U.S. Pat. Nos. RE 37,393, 6,265,190, and 6,596,521 (succinic acid fermentation); U.S. Pat. No. 5,464,760, WO 2003/095659, Mercier et al., *J. Chem. Tech. Biotechnol.* 55: 111-121, Zhang and Cheryan, *Biotechnol. Lett.* 13: 733-738 (1991), Linko and Javanainen, *Enzyme Microb. Technol.* 19: 118-123 (1996), and Tsai and Moon, *Appl. Biochem. Biotechnol.* 70-72: 417-428 (1998) (lactic acid fermentation); U.S. Pat. Nos. 7,320,882, 7,332,309, 7,666,634, and Zhang et al., *Appl. Microbiol. Biotechnol.* 77: 355-366 (2007) (fermentation of various amino acids). The above enumerated list are only examples and one skilled in the art will be aware of a number of fermenting microorganisms that may be appropriately used to obtain a desired end product.

3.6. Simultaneous Saccharification and Fermentation (SSF)

During SSF, the hydrolyzing enzymes are added along with the end product producer, commonly a microorganism. Enzymes release lower-molecular-weight sugars, i.e., fermentable sugars DP1-3, from the starch substrate, while the microorganism simultaneously uses the fermentable sugars for growth and production of the end product. Typically, fermentation conditions are selected that provide an optimal pH and temperature for promoting the best growth kinetics of the producer host cell strain and catalytic conditions for the enzymes produced by the culture. See, e.g., Doran et al., *Biotechnol. Progress* 9: 533-538 (1993).

In further embodiments, by use of appropriate fermenting microorganisms as known in the art to produce the desired end product, those of skill in the art are well capable of adjusting the SSF conditions, e.g., temperature, nutrient composition, light conditions, oxygen availability, etc.

4. Compositions Comprising the Glucoamylase Variants and the Use Thereof

The glucoamylase variants as contemplated herein may be used in enzyme compositions including but not limited to starch hydrolyzing and saccharifying compositions, cleaning and detergent compositions (e.g., laundry detergents, dish washing detergents, and hard surface cleaning compositions), alcohol fermentation compositions, and in animal feed compositions, for example. Further, these glucoamylases may be used in baking applications, such as bread and cake production, brewing, healthcare, textile, environmental waste conversion processes, biopulp processing, and biomass conversion applications.

In some embodiments, an enzyme composition comprising a glucoamylase as contemplated herein will be optionally used in combination with any one or in any combination with the following enzymes: hexokinases, xylanases, glucose isomerases, xylose isomerases, other isomerases, phosphatases, phytases, pullulanases, β-amylases, α-amylases, trehalases, proteases, cellulases, hemicellulases, lipases, cutinases, isoamylases, redox enzymes, esterases, transferases, pectinases, alpha-glucosidases, beta-glucosidases, lyases, other glucoamylases, and other hydrolases.

In some embodiments, the enzyme composition will include an alpha amylase such as fungal alpha amylases (e.g., *Aspergillus* sp.) or bacterial alpha amylases (e.g., *Bacillus* sp. such as *B. stearothermophilus*, *B. amyloliquefaciens*, *B. subtilis*, and *B. licheniformis*) and variants and hybrids thereof. In some embodiments, the alpha amylase is an acid stable alpha amylase. In some embodiments, the alpha-amylase is *Aspergillus kawachi* alpha amylase (AkAA), see U.S. Pat. No. 7,037,704. Commercially available alpha amylases contemplated for use in the compositions of the disclosure are known and include GZYME G997, SPEZYME FRED, SPEZYME XTRA (Danisco US, Inc, Genencor Division), TERMAMYL 120-L and SUPRA (Novozymes, Biotech.).

In some embodiments, the enzyme composition will include an acid fungal protease. In a further embodiment, the acid fungal protease is derived from a *Trichoderma* sp and may be any one of the proteases disclosed in US 2006/0154353, published Jul. 13, 2006, incorporated herein by reference. In a further embodiment, the enzyme composition will include a phytase from *Buttiauxiella* spp. (e.g., BP-17, see also variants disclosed in PCT patent publication WO 2006/043178).

In other embodiments, the glucoamylases as contemplated herein may be combined with other glucoamylases. In some embodiments, such glucoamylases will be combined with one or more glucoamylases derived from other *Trichoderma* strains or variants of *Monascus kaoliang*, or of *Aspergillus* or variants thereof, such as *A. oryzae*, *A. niger*, *A. kawachi*, *A. fumigatus*, *A. terreus*, and *A. awamori*; glucoamylases derived from strains of *Humicola* or variants thereof; glucoamylases derived from strains of *Talaromyces* or variants thereof, such as *T. emersonii*; glucoamylases derived from strains of *Athelia*, such as *A. rolfsii*; or glucoamylases derived from strains of *Penicillium*, such as *P. chrysogenum*, for example.

In particular, glucoamylases as contemplated herein may be used for starch conversion processes, and particularly in the production of dextrose for fructose syrups, specialty sugars and in alcohol and other end product (e.g., organic acids, amino acids, biofuels, and other biochemicals) production from fermentation of starch containing substrates (e.g., G. M. A. van Beynum et al., Eds. (1985) STARCH CONVERSION TECHNOLOGY, Marcel Dekker Inc. NY; see also U.S. Pat. No. 8,178,326). Dextrins produced using variant glucoamylase compositions of the disclosure may result in glucose yields of at least 80%, at least 85%, at least 90% and at least 95%. Production of alcohol from the fermentation of starch substrates using glucoamylases as contemplated herein may include the production of fuel alcohol or potable alcohol.

In some embodiments, the glucoamylase variants as contemplated herein will find use in the hydrolysis of starch from various plant-based substrates, which are used for alcohol production. In some embodiments, the plant-based substrates will include corn, wheat, barley, rye, milo, rice, sugar cane, potatoes, and combinations thereof. In some embodiments, the plant-based substrate will be fractionated plant material, for example, a cereal grain such as corn, which is fractionated into components such as fiber, germ, protein and starch (endosperm) (U.S. Pat. No. 6,254,914 and U.S. Pat. No. 6,899,910). Methods of alcohol fermentations are described in THE ALCOHOL TEXTBOOK, A REFERENCE FOR THE BEVERAGE, FUEL AND INDUSTRIAL ALCOHOL INDUSTRIES, 3rd Ed., Eds. K. A. Jacques et al., 1999, Nottingham University Press, UK. In certain embodiments, the alcohol will be ethanol. In particular, alcohol fermentation production processes are characterized as wet milling or dry grinding processes. In some embodiments, the glucoamylase can be used in a wet milling fermentation process, and in other embodiments, the glucoamylase will find use in a dry grinding process.

Dry grain grinding involves a number of basic steps, which generally include: grinding, cooking, liquefaction, saccharification, fermentation, and separation of liquid and solids to produce alcohol and other co-products. Plant material and particularly whole cereal grains, such as corn, wheat, or rye are ground. In some cases, the grain may be first fractionated into component parts. The ground plant material may be milled to obtain a coarse or fine particle. The ground plant material can be mixed with liquid (e.g., water and/or thin stillage) in a slurry tank. The slurry is subjected to high temperatures (e.g., 90° C. to 105° C. or higher) in a jet cooker along with liquefying enzymes (e.g., alpha amylases) to solubilize and hydrolyze the starch in the grain to dextrins. The mixture can be cooled down and further treated with saccharifying enzymes, such as glucoamylases encompassed by the instant disclosure, to produce glucose. The mash containing glucose may then be fermented for approximately 24 to 120 hours in the presence of fermentation microorganisms, such as ethanol producing microorganism and particularly yeast (*Saccharomyces* spp). The solids in the mash are separated from the liquid phase and alcohol such as ethanol and useful co-products such as distillers' grains are obtained.

The contemplated glucoamylase variant may be a component of a brewing composition used in a process of brewing, i.e., making a fermented malt beverage. Non-fermentable carbohydrates form the majority of the dissolved solids in the final beer. This residue remains because of the inability of malt amylases to hydrolyze the alpha-1, 6-linkages of the starch. The non-fermentable carbohydrates contribute about 50 calories per 12 ounces of beer. The glucoamylase variant, in combination with a glucoamylase and optionally a pullulanase and/or isoamylase, assist in converting the starch into dextrins and fermentable sugars, lowering the residual non-fermentable carbohydrates in the final beer.

The principal raw materials used in making these beverages are water, hops and malt. In addition, adjuncts such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, and syrups, such as corn syrup, sugar cane syrup, inverted sugar syrup, barley and/or wheat syrups, and the like may be used as a source of starch.

For a number of reasons, the malt, which is produced principally from selected varieties of barley, has the greatest effect on the overall character and quality of the beer. First, the malt is the primary flavoring agent in beer. Second, the malt provides the major portion of the fermentable sugar. Third, the malt provides the proteins, which will contribute to the body and foam character of the beer. Fourth, the malt provides the necessary enzymatic activity during mashing. Hops also contribute significantly to beer quality, including flavoring. In particular, hops (or hops constituents) add desirable bittering substances to the beer. In addition, the hops act as protein precipitants, establish preservatives, and aid in foam formation and stabilization.

Grains, such as barley, oats, wheat, as well as plant components, such as corn, hops, and rice, also are used for brewing, both in industry and for home brewing. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. The contemplated glucoamylase variant, by itself or in combination with another α-amylase(s), accordingly may be added to the components used for brewing.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

Processes for making beer are well known in the art. See, e.g., Wolfgang Kunze (2004) "Technology Brewing and Malting," Research and Teaching Institute of Brewing, Berlin (VLB), $3^{rd}$ edition. Briefly, the process involves: (a)

preparing a mash, (b) filtering the mash to prepare a wort, and (c) fermenting the wort to obtain a fermented beverage, such as beer. Typically, milled or crushed malt is mixed with water and held for a period of time under controlled temperatures to permit the enzymes present in the malt to convert the starch present in the malt into fermentable sugars. The mash is then transferred to a mash filter where the liquid is separated from the grain residue. This sweet liquid is called "wort," and the left over grain residue is called "spent grain." The mash is typically subjected to an extraction, which involves adding water to the mash in order to recover the residual soluble extract from the spent grain. The wort is then boiled vigorously to sterilize the wort and help develop the color, flavor and odor. Hops are added at some point during the boiling. The wort is cooled and transferred to a fermentor.

The wort is then contacted in a fermentor with yeast. The fermentor may be chilled to stop fermentation. The yeast flocculates and is removed. Finally, the beer is cooled and stored for a period of time, during which the beer clarifies and its flavor develops, and any material that might impair the appearance, flavors, and/or shelf-life of the beer settles out. The beer usually contains from about 2% to about 10% v/v alcohol, although beer with a higher alcohol content, e.g., 18% v/v, may be obtained. Prior to packaging, the beer is carbonated and, optionally, filtered and pasteurized.

The brewing composition comprising the contemplated glucoamylase variant, in combination with another glucoamylase and optionally an alpha amylase, a pullulanase, and/or isoamylase, may be added to the mash of step (a) above, i.e., during the preparation of the mash. Alternatively, or in addition, the brewing composition may be added to the mash of step (b) above, i.e., during the filtration of the mash. Alternatively, or in addition, the brewing composition may be added to the wort of step (c) above, i.e., during the fermenting of the wort.

A fermented beverage, such as a beer, can be produced by one of the methods above. The fermented beverage can be a beer, such as full malted beer, beer brewed under the "Reinheitsgebot," ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

In some embodiments, the disclosure pertains to a method of saccharifying a liquid starch solution, which comprises an enzymatic saccharification step using one or more glucoamylases as contemplated herein.

The present disclosure also provides an animal feed composition or formulation comprising at least one glucoamylase as contemplated herein. Methods of using a glucoamylase enzyme in the production of feeds comprising starch are provided in e.g. WO 2003/049550 (herein incorporated by reference in its entirety). Briefly, the glucoamylase may be admixed with a feed comprising starch. The glucoamylase is capable of degrading resistant starch for use by the animal, either in vitro or in vivo. Other objects and advantages of the present disclosure are apparent from the present specification.

5. METHODS USED IN THE EXAMPLES

The following materials, assays, and methods are used in the examples provided below:

HPLC Method to Measure Saccharide Composition, Ethanol Yield, and DP4+Reduction

The composition of the reaction products of oligosaccharides was measured by a HPLC system (Beckman System Gold 32 Karat Fullerton, Calif.). The system, maintained at 50° C., was equipped with a Rezex 8 u8% H Monosaccharides column and a refractive index (RI) detector (ERC-7515A, Anspec Company, Inc.). Diluted sulfuric acid (0.01 N) was applied as the mobile phase at a flow rate of 0.6 ml/min. 20 µl of 4.0% solution of the reaction mixture was injected onto the column. The column separates saccharides based on their molecular weights. The distribution of saccharides and the amount of each saccharide were determined from previously run standards.

To determine the ethanol yield and DP4+ reduction, time point samples were thawed at 4° C. and centrifuged for 2 min at 15,000 rpm. 100 µL of the sample supernatants were mixed in individual microcentrifuge tubes with 10 µL of 1.1 N sulfuric acid and incubated 5 min at room temp. 1 mL of water was added to each tube, and the tubes were centrifuged for 1 min at 15,000 rpm. 200 µL were filtered onto an HPLC plate. The plate was analyzed on an Agilent HPLC using a Rezex Fast Fruit RFQ column with 8 min elution. Calibration curves for the above components were prepared using a Supelco Fuel Ethanol (Sigma Cat. 48468-U). DP1, DP2, DP4+, glycerol, acetic acid, lactic acid, and ethanol concentration (g/L) were determined using the ChemStation software. Ethanol production was converted to the percent v/v of the reaction mixture.

pNPG Glucoamylase Activity Assay

Reagent solutions: NaAc buffer (200 mM sodium acetate buffer pH 4.5); Substrate (50 mM p-nitrophenyl-α-D-glucopyranoside (Sigma N-1377) in NaAc buffer (0.3 g/20 ml)) and stop solution (800 mM glycine-NaOH buffer pH 10). 30 µl of filtered enzyme supernatant was placed in a fresh 96-well flat bottom microtiter plate (MTP). To each well 50 µl of NaAc buffer and 120 µl of substrate was added and incubated for 30 minutes at 50° C. (Thermolab systems iEMS Incubator/shaker HT). The reaction was terminated by adding 100 µl of stop solution. The absorbance was measured at 405 nm in a microplate spectrophotometer (Molecular Devices Spectramax 384 plus) and the activity was calculated using a molar extinction coefficient of 0.011 µM/cm.

Amylopectin Activity Assay

Reagents: ABTS (2,2'-Azina-bis(30ehtylynbenzothiazoline-6-sulfonic acid) diammonium salt (Sigma #A1888); Peroxidase Type VI from Horseradish (Sigma #P8375) prepared as 2500 U/mL solution; Glucose Oxidase (Genencor OxyGO HP L5000); calcium chloride solution (100 mM in deionized water); Sodium Acetate buffer (1 M, pH 4.3); deionized water containing 0.005% v/v Tween 80 (Polysorbate 80); and amylopectin from potato starch (Fluka/Sigma #10118).

The HRP-ABTS reactant cocktail (containing 63 mg ABTS, 92 µl HRP (Horseradish peroxidase) (2500 U/mL), 107 µl OxyGO, 230 µl CaCl$_2$ (100 mM), 1.15 mL Sodium Acetate buffer, 9.42 mL water/Tween) was prepared fresh on the day of assay, stored refrigerated, and protected from light.

Substrate: a 2% w/w solution of amylopectin was prepared by bringing amylopectin slurried in water/0.005% tween to a quick boil. The amylopectin substrate solution was allowed to cool to room temperature before use.

In a reaction cuvette, 110 µl of HRP-ABTS reactant cocktail was incubated for 120 seconds at 30° C. 5 µl of diluted enzyme sample was added, mixed, and incubated for 60 sec. 115 µl of amylopectin substrate solution was added, mixed, and incubated for 60 seconds. Absorbance at 405 nm was measured at 30 second intervals for 300 seconds.

In the amylopectin assay, GAUs are measured as the enzyme's ability to catalyze the hydrolysis of amylopectin to release glucose. The glucose released is converted to stoichiometric amounts of gluconic acid and hydrogen peroxide by glucose oxidase. The hydrogen peroxide oxidizes ABTS (catalyzed by HRP) to give a green color that is measured spectrophotometrically at 405 nm. The amount of green color is proportional to glucoamylase activity.

Starch Reference Assay

This assay is based on a 60-minute hydrolysis of a soluble starch substrate (Potato Starch) at pH 4.2 and 60° C. The resulting reducing sugars are determined by the Schoorl Method and calculated as glucose. The Schoorl Method is a copper reduction method employing the Fehling solution. Reduced copper is determined indirectly by iodometric titration of the unreduced copper salt remaining after sugar oxidation. One Glucoamylase Unit (GAU) is the amount of enzyme that is capable of releasing one gram of reducing sugar as glucose per hour under the conditions of the assay.

Determination of Glucoamylase Activity Units (GAU)

Glucoamylase activity units (GAU) were determined based on the ability of a glucoamylase enzyme to catalyze the hydrolysis of p-nitrophenyl-alpha-D-glucopyranoside (pNPG) to glucose and p-nitrophenol. At an alkaline pH, p-nitrophenol forms a yellow color that is measured spectrophotometrically at 405 nm. The amount of p-nitrophenol released correlates with the glucoamylase activity.

Protein Concentration Determination

The protein concentration in a sample was determined using the Bradford QuickStart™ Dye Reagent (Bio-Rad, California, USA). For example, a 10 µL sample of the enzyme was combined with 200 µL Bradford QuickStart™ Dye Reagent. After thorough mixing, the reaction mixture was incubated for at least 10 minutes at room temperature. Air bubbles were removed and the optical density (OD) was measured at 595 nm. The protein concentration was then calculated using a standard curve generated from known amounts of bovine serum albumin.

Determination of Glucose Concentration

Glucose concentration in a saccharification reaction mixture was determined with the ABTS assay. Samples or glucose standards in 5 µL were placed in wells of a 96-well microtiter plate (MTP). Reactions were initiated with the addition of 95 µL of the reactant containing 2.74 mg/ml 2,2'-azino-bis(3-ethylbenzothiazoline-6-sulfonic acid) diammonium salt (ABTS) (Sigma P1888), 0.1 U/ml horseradish peroxidase type VI (Sigma P8375), and 1 U/ml glucose oxidase (Sigma G7141). $OD_{405\ nm}$ was immediately monitored at a 9-second interval for 300 seconds using a microplate spectrophotometer (Molecular Devices Spectramax). Because the rate of $OD_{405\ nm}$ increase is proportional to the glucose concentration, the sample's glucose concentration was determined by comparing with the glucose standard, and was reported as mg/ml.

EXAMPLES

The following examples are provided in order to demonstrate and further illustrate certain representative embodiments and aspect of the present disclosure and are not to be construed as limiting the scope thereof.

Example 1

Effect of Oxidation on TrGA and the CS4 Variant

Formulation stability studies revealed that TrGA product blends lose 15-20% glucoamylase activity after 1 month storage at 37° C. (data not shown). Concurrently, a significant drop in pNPG activity (~50%) was noted in samples kept at 4° C. for several months (data not shown). Similar activity loss was also observed for enzyme blends containing the TrGA variant CS4 (TrGA variant having L417V, T430A, Q511H, A539R, and N563I of SEQ ID NO: 2). The mechanism of activity loss in these samples was unclear. Among several plausible hypotheses, protein oxidation as a mechanism of activity loss was investigated. For this, treatment of purified enzyme with hydrogen peroxide was used to characterize the functional and structural consequences of amino acid oxidation upon the enzymatic activity. A similar approach has been successfully used in prior studies on the serine protease subtilisin. See Estell et al., (1985) *J. Biol. Chem.* 260: 6518-6521; see also Bott et al., (1988) *J. Biol. Chem.* 263: 7895-7906.

Experiments were conducted to determine (1) whether hydrogen peroxide treatment is responsible for the loss in pNPG activity and amylopectin activity for TrGA (wild type) and the CS4 variant, and (2) whether this activity loss is due to protein impairment or a change in specific activity due to oxidation.

Materials: Purified CS4 48 (+/−5) mg/mL; Purified wild type TrGA 44 (+/−6) mg/mL; 0.1M Sodium Acetate pH 4.3; 50% Hydrogen Peroxide; Oxy-Gone Catalase (to inactivate hydrogen peroxide); and Econo-pac 10 DG Disposable Chromatography columns (BioRad).

Procedure:
1) Dilute Oxy-Gone Catalase 10-fold with distilled water;
2) Dilute each enzyme sample 1:10 with 0.1M Sodium Acetate pH 4.3;
   0.6 mL of Purified TrGA into 5.4 mL of 0.1 M Sodium Acetate pH 4.3
   0.6 mL of Purified CS4 into 5.4 mL of 0.1 M Sodium Acetate pH 4.3
3) Split the above into 2 fractions and add hydrogen peroxide to one fraction and water to the other;

| Per 3 mL fraction | 90 µl of 50% Hydrogen Peroxide (0.5M final concentration) |
|---|---|
| Per 3 mL fraction | 90 µl of MilliQ water (control) |

4) Incubate these 4 mixtures at room temperature and take 90 µl aliquots at different time points;
5) At every time point (times may vary), to 90 µl of the mixture, add 10 µl of dilute catalase to samples containing hydrogen peroxide, or add 10 µl of MilliQ water to the control samples
6) Dilute enzyme samples in a non-binding dilution plate (white round bottom polystyrene Corning® 3605);
   Row A: 80 µl of enzyme sample
   Rows B-D: 1:2 serial dilutions using 0.1 M sodium acetate, pH 4.3
   Include 2 water blanks and catalase controls
7) Transfer diluted samples to assay plate and determine residual enzyme activity with the pNPG plate assay;
8) After oxidized samples lost 70-80% of their activity, continue with steps 9-15 to remove hydrogen peroxide from the remaining material for further testing;
9) Obtain a Econo-pac chromatography column;

10) Equilibrate the column with 20 mL 0.1 M sodium acetate buffer pH 4.3;
11) Let buffer run all the way into gel;
12) Add 3 mL sample mixture;
13) Let sample run all the way into gel;
14) Add 3 mL pH 4.3 buffer; and
15) Collect all 3 mL of sample into labeled tube.

As shown in FIG. 2, treatment of TrGA (WT) and the CS4 variant with 0.5 M hydrogen peroxide at room temperature for 7 hours resulted in a 70% to 80% drop of pNPG activity. However, the oxidized forms of TrGA and the CS4 variant showed different changes in activity when using amylopectin (AP) as a substrate. As indicated in Table 1 below, hydrogen-peroxide-treated TrGA retained its full activity, while hydrogen-peroxide-treated CS4 lost about 22% of its activity.

TABLE 1

Comparison of activity loss between TrGA and CS4 using various substrates.

| Sample | pNPG activity (7 hrs) GAU/g | % pNPG activity (7 hrs) | AP activity (7 hrs) GAU/g | % AP activity (7 hrs) |
|---|---|---|---|---|
| TrGA + water | 14 | 100% | 49.2 | 100% |
| TrGA + 0.5M $H_2O_2$ | 3.66 | 26% | 51.2 | 104% |
| CS4 + water | 8.46 | 100% | 80.55 | 100% |
| CS4 + 0.5M $H_2O_2$ | 1.85 | 22% | 62.85 | 78% |

Figure 3:
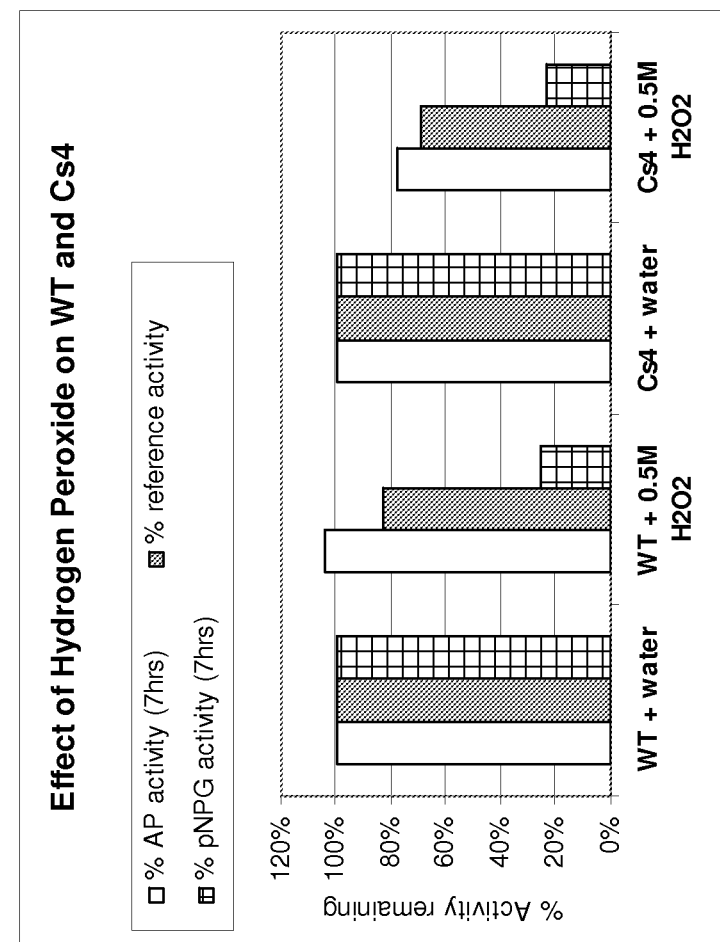
FIG. 3 depicts the remaining activity for TrGA (WT) and the CS4 variant upon hydrogen peroxide treatment for 7 hours. The experiments were performed as described in Example 1. The tested substrates include pNPG, amylopectin (AP), and potato starch (reference).

The data are also shown in FIG. 3, which shows a reduction of starch reference activity (using potato starch as the substrate) of about 20-30%, for both hydrogen peroxide-treated TrGA and CS4.

Figure 4:
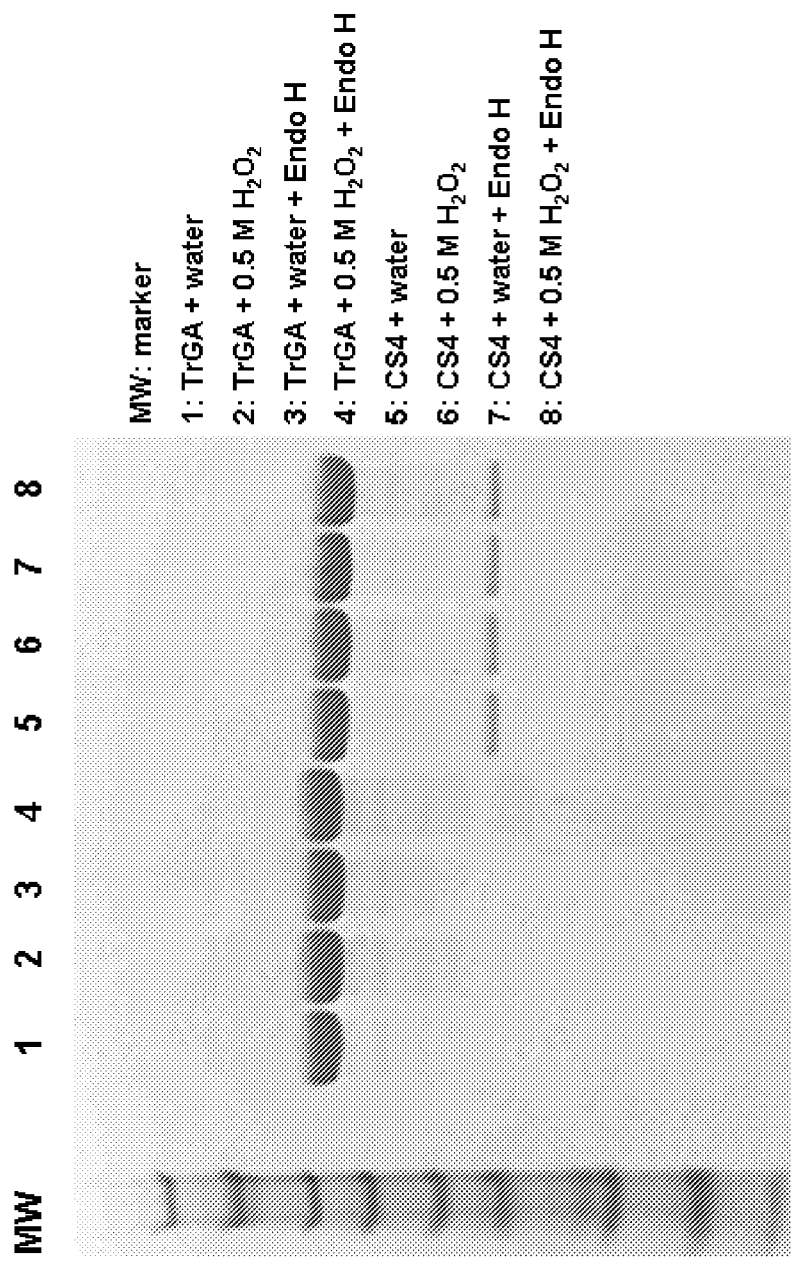
FIG. 4 depicts the SDS-PAGE analysis of TrGA (WT) and the CS variant upon hydrogen peroxide treatment. The experiments were performed as described in Example 1.

SDS-PAGE gel analysis (FIG. 4) shows that the hydrogen peroxide treated glucoamylases (both TrGA and CS4) remained intact, with or without the presence of Endoglycosidase H (Endo H). From these results, it appears that a change in the glucoamylase specific activity, rather than protein degradation, may be responsible for the observed oxidation-related activity loss.

Example 2

MS-Based Protein Oxidation Mapping

To further characterize the observed activity loss due to hydrogen peroxide treatment, particularly the distinct profile of CS4, mass spectrometry (MS) analysis was conducted. All glucoamylase samples were precipitated with 10% TCA followed by the reduction reaction with 20 mM DTT at 50° C. for 15-20 min. The alkylation reaction was also performed with 55 mM Iodoacetamide (IAA). The alkylation reaction was conducted in dark for 45 min at room temperature. Proteolytic digestion was performed by incubation with the Asp-N protease in 25 mM ammonium bicarbonate for overnight at 37° C. (Asp-N to TrGA or CS4 ratio was adjusted to 1:20 by weight). All protein digests were analyzed by MALDI-TOF/MS and LC-MS/MS for the MRM study.

For MALDI-TOF/MS analysis, the desalted samples were prepared by co-crystallizing equal volumes (1 µL) of the sample with CHCA (α-cyano-4-hydroxycinnamic acid, saturated in 70% acetonitrile with 0.1% formic acid) using the dried droplet method. Peptide mass spectra were obtained using a Voyager DE-STR MALDI-TOF mass spectrometer (Applied Biosystems, Foster City, Calif., USA). The instrument settings for the 700-2500 m/z range were: reflector mode of operation, delayed extraction mode, positive polarity, 20 kV acceleration voltage, 68% grid voltage, and 175 nsec extraction delay time. For each spectrum, 300 laser shots were taken and Calibration Mixture-1 (Sigma, Saint Louis, Mo.) was used as the external calibrant.

For MRM/MS analysis, all digested samples were analyzed by ESI LC/MS/MS on a triple-quadrupole ion trap mass spectrometer (TSQ Quantum Access, Thermo Scientific). The digested sample was first run by LC-MS/MS (Data-dependant mode) in order to determine and select for the targeted peptides un-oxidized and oxidized) for the subsequent MRM study. Also, the MRM workflow software (Pinpoint™ software, Thermo Scientific) was used for predicting candidate peptides and choosing multiple fragment ions for MRM assay design, for building an instrument method and a sequence file, and also for quantitative data processing. High-confidence detection of targeted peptides was achieved using time alignment of specific multiple fragment ions (b or y) from each peptide. The instrument was set up to cycle through each set of MRM transition (typically 3 primary fragment ions/targeted peptide) in a given method, for a total cycle time of 60 ms.

Figure 5A:
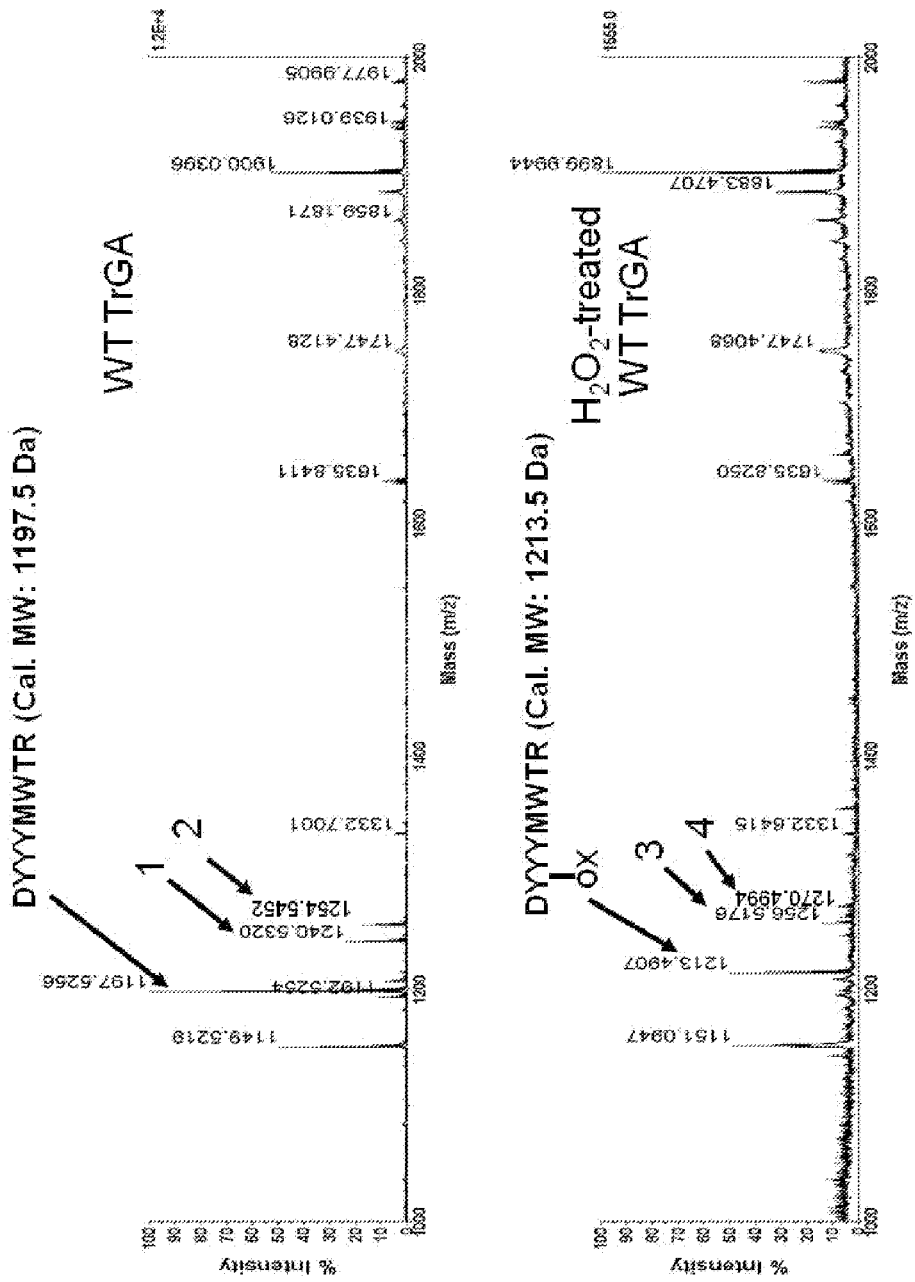
FIGS. 5A-B depict the MALDI-TOF/MS analysis on in-solution digestion (Asp-N) for TrGA (FIG. 5A) and CS4 (FIG. 5B), with or without hydrogen peroxide treatment. The experiments were performed as described in Example 2. Only the analysis of the mass range of 1001-2000 Dalton is shown, because difference was not identified within other ranges. The arrows indicate peaks showing shifts in hydrogen peroxide-treated samples.
Figure 5B:
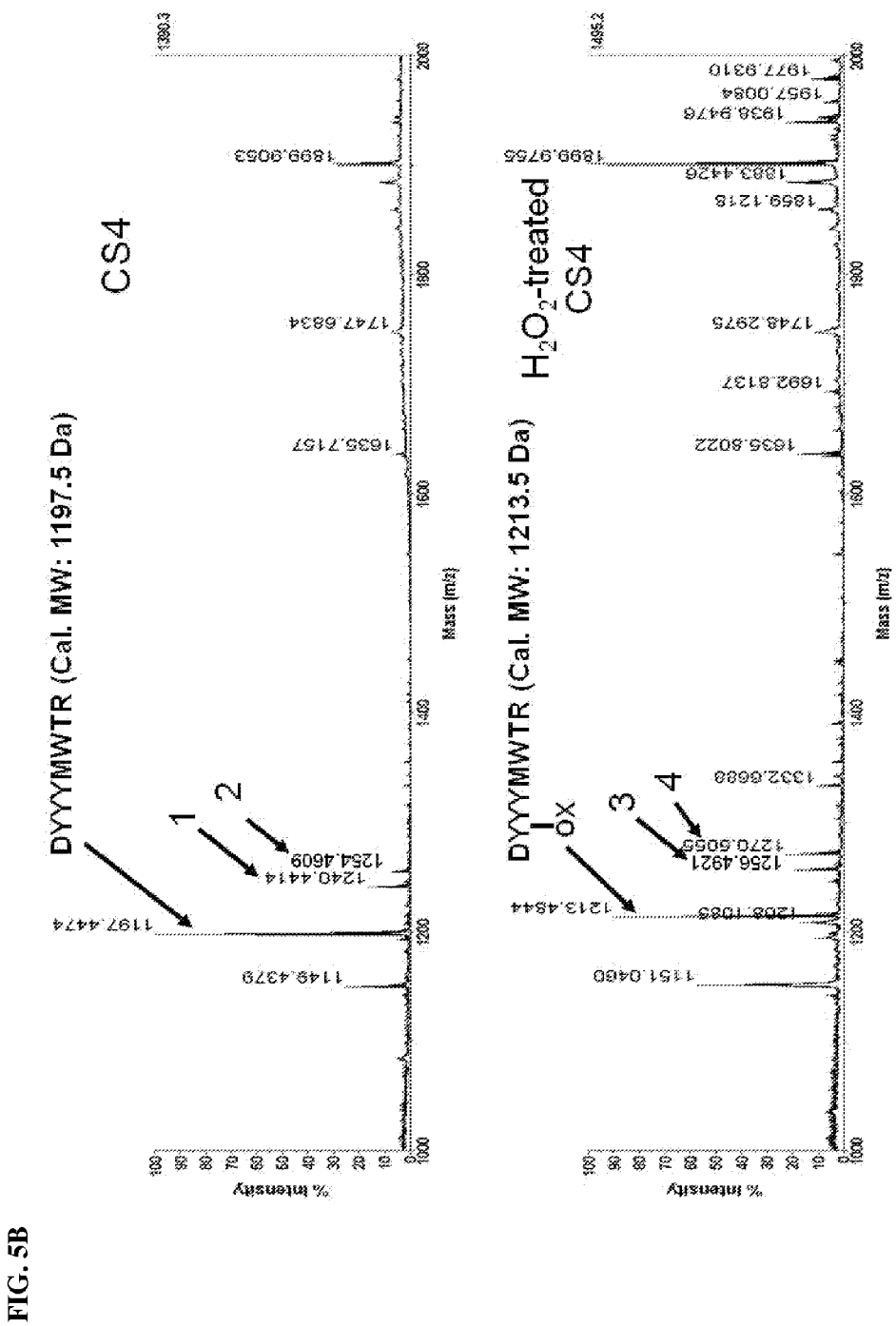

MRM method was set up as follows:
Q1: 0.7 FWHM
Q3: 0.7 FWHM
Collision Gas Pressure: 1.2 mTorr
Collision Energy: 35-45 V
Dwell times: 20 ms
HPLC for the TSQ Quantum Access was set up as follows:
Pump: Thermo Scientific Surveyor™ MS pump with autosampler
Column: Vydac RP-C18 (2.1 mm×150 mm)
Flow rate: 200 µL/min
Buffer A: 0.1% FA in DI Water
Buffer B: 0.1% FA in Acetonitrile
Gradient: 0% B to 70% B in 50 min
Sample injection: 20 µL FIGS. 5A and 5B show MALDI-TOF/MS analysis (mass range of 1001-2000 Dalton) on in-solution digestion (Asp-N) for both TrGA and CS4, with or without hydrogen peroxide treatment. Methionine 50 (M50) was identified as the only protein oxidation site on the hydrogen peroxide-treated TrGA and CS4 (data not shown for other mass ranges). Treatment by 0.5 M hydrogen peroxide resulted in 100% oxidation for M50 in both TrGA and CS4. Two other peptides (peaks 1/3 and 2/4, as indicated by arrows in FIGS. 5A-B) were confirmed as the carboxylated and carbamidomethylated forms of the same TrGA peptide (46-53) (data not shown). These peptide modifications were probably caused by the excess amount of Iodoacetamide (IAA) used in the protein reduction and alkylation reactions prior to the proteolytic digestion.

Example 3

Application Performance Characterization for M50 Oxidation

The effect of M50 oxidation in both TrGA and CS4 was further characterized in SSF processes. SSF was conducted as follows:
1) Incubate frozen liquefact at 70° C. until completely thawed, usually 4-5 hours;
2) Weigh out appropriate amount of liquefact and add solid urea to 600 ppm;

3) Adjust liquefact pH to 4.8 using 6 N sulfuric acid and/or 28% ammonium hydroxide;
4) Add 0.1% w/w dry yeast to liquefact batch;
5) Add appropriate amount (1:6 GA:AA activity ratio) of AkAA to liquefact batch;
6) Mix well with a whisk;
7) Weigh out 100 g+/−0.2 g liquefact into individually labeled 125 ml Erlenmeyer flasks in replicates of two;
8) Add appropriate amount of glucoamylase to appropriate flask;
9) Add a stir bar and a red weight ring to each flask and cover with aluminum foil;
10) Incubate in the water bath with mixing at 320 rpm for 55 hours at 32° C.;
11) ~1 ml time point samples are taken at approximately t=0, 6, 18, 25, 43, and 55 hours and stored frozen;
12) Each time point sample set is thawed at 4° C. and centrifuged for 2 minutes at 15,000 rpm;
13) In individually labeled microcentrifuge tubes, mix 100 μl of sample supernatant with 10 μl of 1.1 N sulfuric acid and incubate 5 minutes at room temperature;
14) Add 1 ml of water to each tube and centrifuge for 1 minute at 15,000 rpm;
15) 200 μl of each sample are loaded into HPLC tubes and analyzed on the HPLC using an Aminex HPX-87H column;
16) DP1, DP2, DP3+, glycerol, acetic acid, lactic acid, and ethanol concentration (% w/v) are determined using the Waters Empower software; and
17) Calibration curves for the above components are prepared using a Supelco Fuel Ethanol Standard (Sigma Cat#48468-U).

For a liquefact of 35% dry solids, wild type TrGA was dosed at 0.325 GAU/g ds (1×dose), CS4 was dosed at 0.016 mg/g liquefact or 0.045 mg/g ds (0.7×dose), and AkAA was dosed at 1.95 SSU/G ds. TrGA or CS4 having 0% oxidation, 50% oxidation (by mixing equal amounts of the enzyme having 0% and 100% oxidation), and 100% oxidation were used in the above SSF experiments). The DP3+ levels were measured through the void volume, the reduction of which is commonly interpreted to reflect the efficiency of liquefact saccharification. The data are presented in FIGS. 6A and 6B.

Figure 6A:
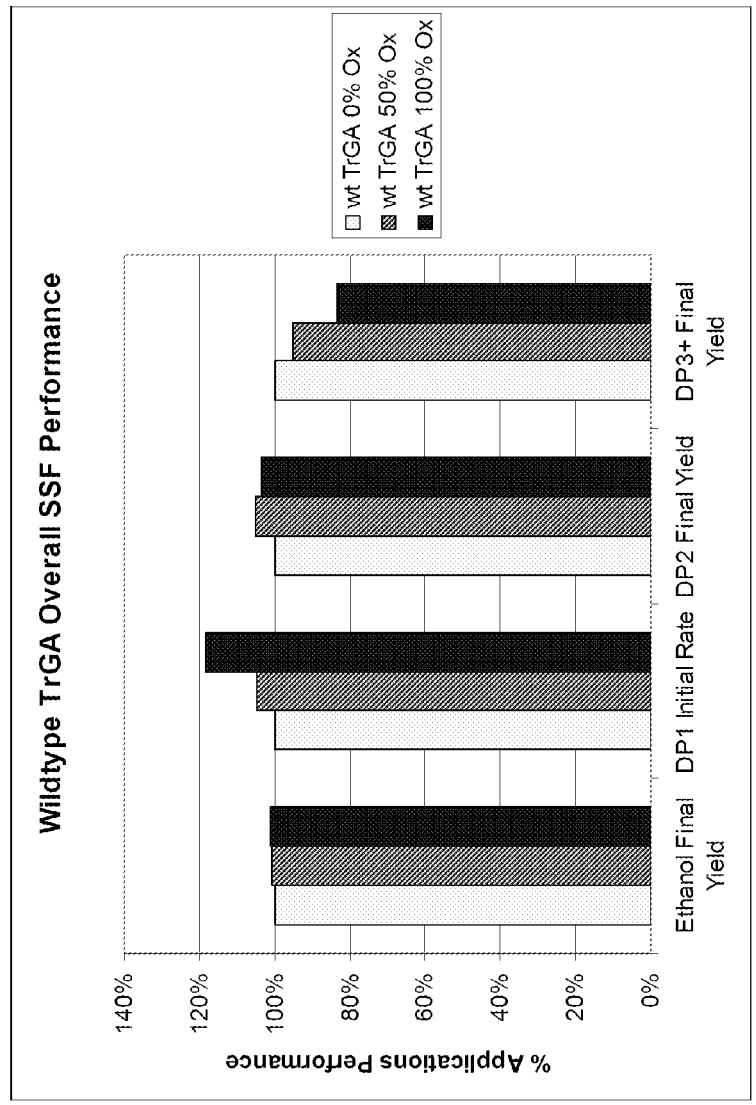
FIGS. 6A-B depict the overall SSF performance for TrGA and the CS4 variant having various degree of oxidation (0%, 50%, and 100%).
Figure 6B:
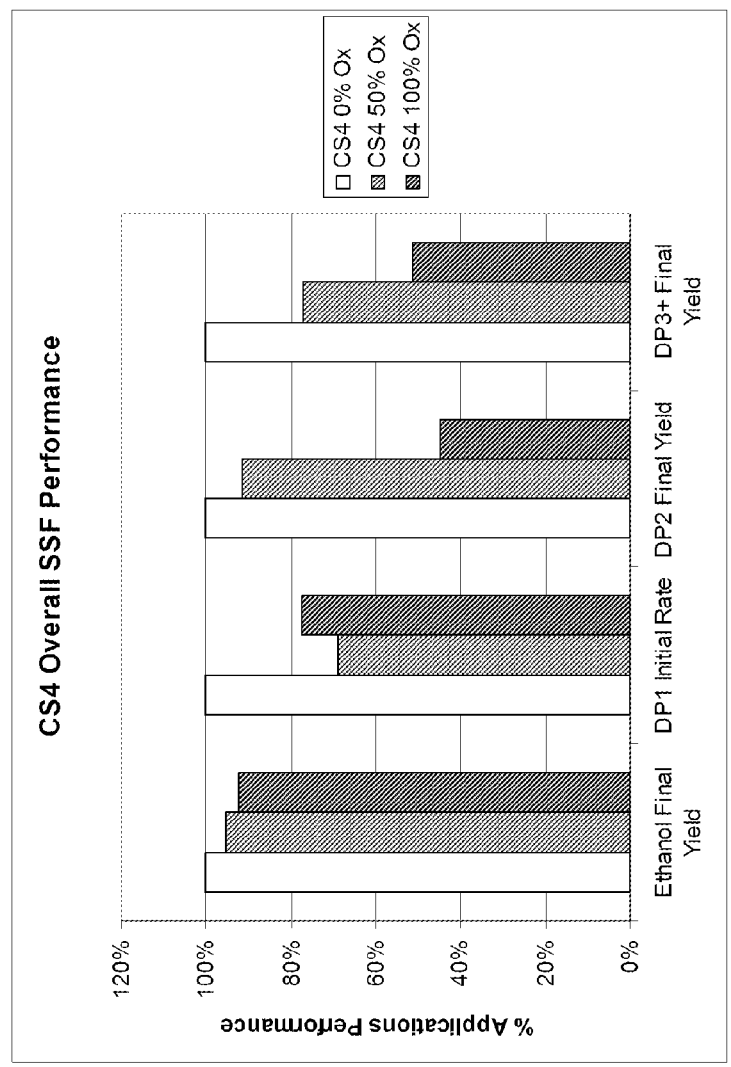

Combined with the results shown in Example 1, the functional properties of oxidized TrGA and oxidized CS4 were found to differ significantly. Hydrolysis of pNPG and activity in the starch reference assay were both decreased upon oxidation of M50 for both enzymes (pNPG activity decreased to a much greater degree). Oxidized TrGA retained full activity on amylopectin, while oxidation of CS4 resulted in a measureable decrease in activity on amylopectin. The effect of oxidation on SSF performance was also quite different for the two enzymes. Ethanol yield, DP1 initial rate, final DP2, and final DP3+ levels were similar for native and oxidized TrGA (FIG. 6A). CS4, by contrast, exhibited significant losses in ethanol yield and decreased target levels for DP1 initial rate, final DP2 and final DP3+ following oxidation (FIG. 6B). According to the determined TrGA crystal structure, M50 and two of the five substitutions in CS4, L417V and A539R, are likely located in close proximity to the enzyme active site. Oxidation may destabilize binding of substrate, the transition state, or both. However, it remains unclear why the effect of oxidation on SSF performance is different for TrGA and CS4.

Example 4

Construction and Characterization of CS4 M50 Variants

Based on the above Examples, it appears that commercial products containing CS4 would be susceptible to SSF performance loss due to oxidation. Careful monitoring of the product's pNPG activity possibly may identify production lots having possible oxidation. Alternatively, oxidation may be monitored by mass spectrometry. Substituting M50 with a non-oxidizable amino acid, however, would be a long term solution to this problem.

A BLAST search of the NCBI protein database using the TrGA sequence indicated that (1) M50 is not completely conserved, and (2) threonine and histidine are found at this site in homologous sequences (data not shown). A site evaluation library screen of all nineteen substitutions was conducted to evaluate TrGA variants that are resistant to oxidation-related activity loss while maintaining the increased performance efficiency benefit exhibited by CS4. After preliminary screening (data not shown), variants having M50 in CS4 substituted by glycine (G), phenylalanine (F), lysine (K), or tyrosine (Y) were subject to further characterization for oxidation-related activity loss. As shown in Table 2, variants carrying M50G, M50Y, or M50F substitution, upon hydrogen peroxide treatment, maintained the pNPG activity over 285 minutes, showing only a maximum activity loss of about 10-11%. When incubated in water, these variants showed a maximum activity loss of about 6-7%.

TABLE 2

Characterization of pNPG activity of M50 CS4 variants.

| % Activity | Time (minutes) | | | | |
|---|---|---|---|---|---|
| | 0 | 65 | 155 | 225 | 285 |
| Treated with 0.5M Hydrogen Peroxide | | | | | |
| M50G | 100% | 116% | 103% | 100% | 96% |
| M50Y | 100% | 104% | 95% | 90% | 89% |
| M50F | 100% | 105% | 111% | 90% | 90% |
| Control (in water) | | | | | |
| M50G | 100% | 99% | 95% | 94% | 93% |
| M50Y | 100% | 100% | 98% | 106% | 94% |
| M50F | 100% | 103% | 100% | 99% | 97% |

Following oxidation sensitivity evaluation, these variants were subjected to performance evaluation in the SSF process conducted as follows:
1) Incubate frozen liquefact at 4° C. overnight, then incubate at 60° C. for 2 hours followed by incubation at 32° C. for 30 minutes;
2) Weigh out corn liquefact and add urea to a final concentration of 600 ppm;
3) Adjust liquefact pH to 4.8 using 6 N sulfuric acid and/or 28% ammonium hydroxide;
4) Add 0.1% w/w active dry yeast to liquefact batch;
5) Mix well with an overhead stirrer for 30 minutes at room temperature;
6) Weigh out 100 g+/−0.2 g of liquefact into individually labeled 125 ml Erlenmeyer flasks in replicates of two;
7) Add appropriate volume of glucoamylase to each flask (glucoamylase is dosed as a fraction of the TrGA dose at 0.325 GAU/g dry solids; CS4 or the additional variant is dosed at 0.7× of the wild type protein dose, about 0.015 mg protein/g liquefact);

8) Add appropriate volume of AkAA to each flask (AkAA is dosed as a fraction of the AkAA activity at 1.95 SSU/g dry solids);
9) Mix and stop each flask with a foam stopper;
10) Incubate in a 32° C. forced air incubator with mixing at 200 rpm for 55 hours; and
11) Approximately 1 ml time point samples are collected at t=0, 4, 12, 16, 24, 30, 40, 44, and 55 hours into the fermentations; samples are stored frozen and subject to analysis as described above.

Table 3 shows the ethanol yields for each of the 4 variants. Although variants M50G and M50F produced levels of ethanol at the end of fermentation equivalent to the levels produced in the presence of CS4, their ethanol production rates were significantly slower than those of CS4, producing ethanol up to 14% slower than CS4 in the first 18 hours of fermentation. Both variants M50Y and M50K showed ethanol production rates equivalent to CS4. However, oxidized M50K variant produced 7% less ethanol at the end of the fermentation.

TABLE 3

Ethanol production in SSF for various CS4 M50 variants.

| Sample | Ethanol Initial Rate (% w/v/hr) | Control | PI | % Difference | Final Ethanol Yield (%) | Control | PI | % Difference |
|---|---|---|---|---|---|---|---|---|
| Liquefact batch #1 | | | | | | | | |
| CS4 | 0.65 | 0.65 | 1.00 | 0% | 14.84 | 14.84 | 1.00 | 0% |
| M50G | 0.56 | 0.65 | 0.86 | −14% | 15.48 | 14.84 | 1.04 | 4% |
| M50F | 0.57 | 0.65 | 0.87 | −13% | 14.46 | 14.84 | 0.97 | −3% |
| M50Y | 0.68 | 0.65 | 1.05 | 5% | 14.79 | 14.84 | 1.00 | 0% |
| Liquefact batch #2 | | | | | | | | |
| CS4 | 0.21 | 0.21 | 1.00 | 0% | 14.03 | 14.03 | 1.00 | 0% |
| Oxidized M50K | 0.20 | 0.21 | 0.96 | −4% | 13.00 | 14.03 | 0.93 | −7% |
| Un-oxidized M50K | 0.21 | 0.21 | 0.97 | −3% | 14.08 | 14.03 | 1.00 | 0% |

DP4+ hydrolysis was also evaluated in SSF for each of the M50 variants (Table 4). The DP4+ levels were measured through the void volume, the reduction of which is commonly interpreted to reflect the efficiency of liquefact saccharification. As seen in the ethanol production, variants M50G and M50F were much slower to hydrolyze DP4+ with yields consistently higher throughout fermentation than CS4. Variant M50G also yielded significantly higher DP4+ at the end of fermentation than any of the other variants, maintaining 66% more DP4+ than CS4. In contrast, both M50Y and M50K showed equivalent or improved hydrolysis of DP4+ in comparison to CS4.

TABLE 4

DP4+ hydrolysis during SSF for various CS4 M50 variants.

| Sample | DP4+ Initial Rate (% w/v/hr) | Control | PI | % Difference | Final DP4+ (% w/v) | Control | PI | % Difference |
|---|---|---|---|---|---|---|---|---|
| Liquefact batch #1 | | | | | | | | |
| CS4 | 5.35 | 5.35 | 1.00 | 0% | 1.76 | 1.76 | 1.00 | 0% |
| M50G | 4.89 | 5.35 | 0.91 | −9% | 2.92 | 1.76 | 1.66 | 66% |
| M50F | 5.32 | 5.35 | 0.99 | −1% | 1.89 | 1.76 | 1.08 | 8% |
| M50Y | 5.46 | 5.35 | 1.02 | 2% | 1.90 | 1.76 | 1.08 | 8% |
| Liquefact batch #2 | | | | | | | | |
| CS4 | 3.26 | 3.26 | 1.00 | 0% | 1.95 | 1.95 | 1.00 | 0% |
| Oxidized M50K | 3.24 | 3.26 | 0.99 | −1% | 2.31 | 1.95 | 1.19 | 19% |
| Un-oxidized M50K | 3.27 | 3.26 | 1.00 | 0% | 2.09 | 1.95 | 1.07 | 7% |

Given the above data, the CS4 M50Y variant showed equivalent performance to CS4 in both ethanol yields and DP4+ hydrolysis as well as minimal oxidation sensitivity. Although variant M50K also showed equivalent performance to CS4 in its native state, oxidized M50K showed significantly reduced production of ethanol, as well as less efficient DP4+ hydrolysis. Accordingly, the CS4 M50Y variant was selected for further evaluation using liquefact batch #2. The results are summarized in Table 5.

TABLE 5

SSF Performance Evaluation for the CS4 M50 variant.

| Sample | Ethanol Initial Rate (% w/v/hr) | Control | PI | % Difference | Final Ethanol Yield (%) | Control | PI | % Difference |
|---|---|---|---|---|---|---|---|---|
| CS4 | 0.90 | 0.90 | 1.00 | 0% | 16.08 | 16.08 | 1.00 | 0% |
| M50Y | 0.78 | 0.90 | 0.87 | −13% | 16.01 | 16.08 | 1.00 | 0% |

| Sample | DP4+ Initial Rate (% w/v/hr) | Control | PI | % Difference | Final DP4+ (% w/v) | Control | PI | % Difference |
|---|---|---|---|---|---|---|---|---|
| CS4 | 1.21 | 1.21 | 1.00 | 0% | 0.82 | 0.82 | 1.00 | 0% |
| M50Y | 1.30 | 1.21 | 1.07 | 7% | 1.23 | 0.82 | 1.50 | 50% |

As shown in Table 5, the CS4 M50Y variant showed equivalent performance to CS4 for both ethanol production and DP4+ hydrolysis. Although the M50Y variant yielded 50% more DP4+ at the end of fermentation, the obtained value of 1.23% w/v appeared well below the final DP4+ yields of the CS4 M50G variant or oxidized CS4 M50K variant. Thus, the CS4 M50Y variant having the amino acid SEQ ID NO: 6 can be useful to replace TrGA and CS4 in commercial products to provide a longer shelf life, for example.

Various modifications and variations of the described methods and system of the disclosure will be apparent to those skilled in the art without departing from the scope and spirit of the disclosure. Although the disclosure has been described in connection with specific representative embodiments, it should be understood that the subject matters as claimed should not be unduly limited to such specific embodiments. Indeed, various modifications of the described modes for carrying out the disclosure that are obvious to those skilled in the art are intended to be within the scope of the following claims.

SEQUENCE LISTING (full-length TrGA, w/ signal peptide and prosequence)  SEQ ID NO: 1

MHVLSTAVLLGSVAVQKVLGRPGSSGLSDVTKRSVDDFISTETPIALNNLLCNVGPDGCRAF
GTSAGAVIASPSTIDPDYYYMWTRDSALVFKNLIDRFTETYDAGLQRRIEQYITAQVTLQGL
SNPSGSLADGSGLGEPKFELTLKPFTGNWGRPQRDGPALRAIALIGYSKWLINNNYQSTVSN
VIWPIVRNDLNYVAQYWNQTGFDLWEEVNGSSFFTVANQHRALVEGATLAATLGQSGSAYSS
VAPQVLCFLQRFWVSSGGYVDSNINTNEGRTGKDVNSVLTSIHTFDPNLGCDAGTFQPCSDK
ALSNLKVVVDSFRSIYGVNKGIPAGAAVAIGRYAEDVYYNGNPWYLATFAAAEQLYDAIYVW
KKTGSITVTATSLAFFQELVPGVTAGTYSSSSSTFTNIINAVSTYADGFLSEAAKYVPADGS
LAEQFDRNSGTPLSALHLTWSYASFLTATARRAGIVPPSWANSSASTIPSTCSGASVVGSYS
RPTATSFPPSQTPKPGVPSGTPYTPLPCATPTSVAVTFHELVSTQFGQTVKVAGNAAALGNW
STSAAVALDAVNYADNHPLWIGTVNLEAGDVVEYKYINVGQDGSVTWESDPNHTYTVPAVAC
VTQVVKEDTWQS (mature TrGA, w/o signal peptide and prosequence)  SEQ ID NO: 2

SVDDFISTETPIALNNLLCNVGPDGCRAFGTSAGAVIASPSTIDPDYYYMWTRDSALVFKNL
IDRFTETYDAGLQRRIEQYITAQVTLQGLSNPSGSLADGSGLGEPKFELTLKPFTGNWGRPQ
RDGPALRAIALIGYSKWLINNNYQSTVSNVIWPIVRNDLNYVAQYWNQTGFDLWEEVNGSSF
FTVANQHRALVEGATLAATLGQSGSAYSSVAPQVLCFLQRFWVSSGGYVDSNINTNEGRTGK
DVNSVLTSIHTFDPNLGCDAGTFQPCSDKALSNLKVVVDSFRSIYGVNKGIPAGAAVAIGRY
AEDVYYNGNPWYLATFAAAEQLYDAIYVWKKTGSITVTATSLAFFQELVPGVTAGTYSSSSS
TFTNIINAVSTYADGFLSEAAKYVPADGSLAEQFDRNSGTPLSALHLTWSYASFLTATARRA
GIVPPSWANSSASTIPSTCSGASVVGSYSRPTATSFPPSQTPKPGVPSGTPYTPLPCATPTS
VAVTFHELVSTQFGQTVKVAGNAAALGNWSTSAAVALDAVNYADNHPLWIGTVNLEAGDVVE
YKYINVGQDGSVTWESDPNHTYTVPAVACVTQVVKEDTWQS (signal peptide of wild type TrGA)  SEQ ID NO: 3

MHVLSTAVLLGSVAVQKVLG (cDNA of wild type TrGA)  SEQ ID NO: 4

```
atgcacgtcc tgtcgactgc ggtgctgctc ggctccgttg ccgttcaaaa ggtcctggga      60
agaccaggat caagcggtct gtccgacgtc accaagaggt ctgttgacga cttcatcagc     120
accgagacgc ctattgcact gaacaatctt ctttgcaatg ttggtcctga tggatgccgt     180
gcattcggca catcagctgg tgcggtgatt gcatctccca gcacaattga cccggactac     240
tattacatgt ggacgcgaga tagcgctctt gtcttcaaga acctcatcga ccgcttcacc     300
gaaacgtacg atgcgggcct gcagcgccgc atcgagcagt acattactgc ccaggtcact     360
ctccagggcc tctctaaccc ctcgggctcc ctcgcggacg gctctggtct cggcgagccc     420
aagtttgagt tgaccctgaa gcctttcacc ggcaactggg gtcgaccgca gcgggatggc     480
ccagctctgc gagccattgc cttgattgga tactcaaagt ggctcatcaa caacaactat     540
cagtcgactg tgtccaacgt catctggcct attgtgcgca acgacctcaa ctatgttgcc     600
cagtactgga accaaaccgg cttgacctc tgggaagaag tcaatgggag ctcattcttt     660
actgttgcca accagcaccg agcacttgtc gagggcgcca ctcttgctgc cactcttggc     720
cagtcgggaa gcgcttattc atctgttgct ccccaggttt tgtgctttct ccaacgattc     780
```

```
tgggtgtcgt ctggtggata cgtcgactcc aacatcaaca ccaacgaggg caggactggc     840
aaggatgtca actccgtcct gacttccatc cacaccttcg atcccaacct ggctgtgac     900
gcaggcacct tccagccatg cagtgacaaa gcgctctcca acctcaaggt tgttgtcgac    960
tccttccgct ccatctacgg cgtgaacaag ggcattcctg ccggtgctgc cgtcgccatt   1020
ggccggtatg cagaggatgt gtactacaac ggcaacccct tggtatcttg cacatttgct   1080
gctgccgagc agctgtacga tgccatctac gtctggaaga agacgggctc catcacggtg   1140
accgccacct ccctggcctt cttccaggag cttgttcctg gcgtgacggc cgggacctac   1200
tccagcagct cttcgacctt taccaacatc atcaacgccg tctcgacata cgccgatggc   1260
ttcctcagcg aggctgccaa gtacgtcccc gccgacggtt cgctggccga gcagtttgac   1320
cgcaacagcg gcactccgct gtctgcgctt cacctgacgt ggtcgtacgc ctcgttcttg   1380
acagccacgg cccgtcgggc tggcatcgtg ccccccctcgt gggccaacag cagcgctagc  1440
acgatcccct cgacgtgctc cggcgcgtcc gtggtcggat cctactcgcg tcccaccgcc   1500
acgtcattcc ctccgtcgca gacgcccaag cctggcgtgc cttccggtac tccctacacg   1560
cccctgccct gcgcgacccc aacctccgtg gccgtcacct ccacgagct cgtgtcgaca    1620
cagtttggcc agacggtcaa ggtggcgggc aacgccgcgg ccctgggcaa ctggagcacg   1680
agcgccgccg tggctctgga cgccgtcaac tatgccgata ccaccccct gtggattggg    1740
acggtcaacc tcgaggctgg agacgtcgtg gagtacaagt acatcaatgt gggccaagat   1800
ggctccgtga cctgggagag tgatcccaac cacacttaca cggttcctgc ggtggcttgt   1860
gtgacgcagg ttgtcaagga ggacacctgg cagtcgtaa                           1899
```

(mature TrGA variant CS4)                                    SEQ ID NO: 5

SVDDFISTETPIALNNLLCNVGPDGCRAFGTSAGAVIASPSTIDPDYYYMWTRDSALVFKNL
IDRFTETYDAGLQRRIEQYITAQVTLQGLSNPSGSLADGSGLGEPKFELTLKPFTGNWGRPQ
RDGPALRAIALIGYSKWLINNNYQSTVSNVIWPIVRNDLNYVAQYWNQTGFDLWEEVNGSSF
FTVANQHRALVEGATLAATLGQSGSAYSSVAPQVLCFLQRFWVSSGGYVDSNINTNEGRTGK
DVNSVLTSIHTFDPNLGCDAGTFQPCSDKALSNLKVVVDSFRSIYGVNKGIPAGAAVAIGRY
AEDVYYNGNPWYLATFAAAEQLYDAIYVWKKTGSITVTATSLAFFQELVPGVTAGTYSSSSS
TFTNIINAVSTYADGFLSEAAKYVPADGSLAEQFDRNSGTPLSAVHLTWSYASFLTAAARRA
GIVPPSWANSSASTIPSTCSGASVVGSYSRPTATSFPPSQTPKPGVPSGTPYTPLPCATPTS
VAVTFHELVSTQFGHTVKVAGNAAALGNWSTSAAVALDAVNYRDNHPLWIGTVNLEAGDVVE
YKYIIVGQDGSVTWESDPNHTYTVPAVACVTQVVKEDTWQS (mature TrGA variant CS4 with M50Y)                          SEQ ID NO: 6

SVDDFISTETPIALNNLLCNVGPDGCRAFGTSAGAVIASPSTIDPDYYYYWTRDSALVFKNL
IDRFTETYDAGLQRRIEQYITAQVTLQGLSNPSGSLADGSGLGEPKFELTLKPFTGNWGRPQ
RDGPALRAIALIGYSKWLINNNYQSTVSNVIWPIVRNDLNYVAQYWNQTGFDLWEEVNGSSF
FTVANQHRALVEGATLAATLGQSGSAYSSVAPQVLCFLQRFWVSSGGYVDSNINTNEGRTGK
DVNSVLTSIHTFDPNLGCDAGTFQPCSDKALSNLKVVVDSFRSIYGVNKGIPAGAAVAIGRY
AEDVYYNGNPWYLATFAAAEQLYDAIYVWKKTGSITVTATSLAFFQELVPGVTAGTYSSSSS
TFTNIINAVSTYADGFLSEAAKYVPADGSLAEQFDRNSGTPLSAVHLTWSYASFLTAAARRA
GIVPPSWANSSASTIPSTCSGASVVGSYSRPTATSFPPSQTPKPGVPSGTPYTPLPCATPTS
VAVTFHELVSTQFGHTVKVAGNAAALGNWSTSAAVALDAVNYRDNHPLWIGTVNLEAGDVVE
YKYIIVGQDGSVTWESDPNHTYTVPAVACVTQVVKEDTWQS (full-length GA from *Hypocrea citrine* var. *americana*; SQN6 of
U.S. Pat. No. 7,413,879)
SEQ ID NO: 7
MHVLSTAVLLGLVAVQKVLGRPGLNGVPDVTKRSVDDFISNESPIALNNLLCNVGPDGCRAFGASAGTVA

ASPSTTDPDYYYMWTRDSALIFKTVVDRFTQNYDASLQKRIEQYIAAQATLQGISNPSGSLADGSGLGEP

KFELTLNQFTGHWGRPQRDGPALRAIALIGYSKWLIDNNYQSTVSDIIWPILRNDLNYVAQYWNQTGFDL

WEEVEGSSFFTVANQHRALVEGATLAAILGQSGSSYSAVAPQILCFLQKFWVSSGGYVNSNINSDINRTG

KDANSLLASIHTFDPSIGCDPATFQPCSDKALSNLKSVVDSFRSIYGVNQGISAGSAVAIGRYSEDVYFN

GNPWYLATFAAAEQLYDSLYVWKQTGSITVTAIPLAFFQELVPGVAAGTYLSSQSTFTSIVNAVSAYADG

FLNEAAKYVPSDGSLAEQFDKNNGTPLSAVHLTWSYASFLTATARRAGSVPPSWANSNATSIPTACSGTS

VVGSYSSPTATSFPPSQTPKVGKPTGTPFTPIPCATPTSVAVTFHELPTTQFGQTIKLAGSAEALGNWST

GAAVGLDAANYASNHPLWFGTLNLQAGDVIEYKYINVGKDGSVTWESDPNHTYTVPAVACVTEVVKEDTW

QS (full-length GA from *Hypocrea vinosa*; SQN8 of U.S. Pat. No. 7,413,879)
SEQ ID NO: 8
MHVLSTAVLLGSVAVQKVLGRPGSNGLSGVTKRSVDDFINTQTPIALNNLLCNVGPDGCRAFGTSAGAVI

ASPSTTDPDYYYMWTRDSALVFKNIVDRFTQQYDAGLQRRIEQYISAQVTLQGISNPSGSLSDGSGLGEP

KFELTLSQFTGNWGRPQRDGPALRAIALIGYSKWLINNNYQSTVSNIIWPIVRNDLNYVAQYWNQTGFDL

WEEVNGSSFFTVANQHRALVEGATLAATLGQSGSTYSSVAPQILCFLQRFWVSGGYIDSNINTNEGRTGK

DANSLLASIHTFDPSLGCDASTFQPCSDKALSNLKVVVDSFRSIYGVNKGIPAGSAVAIGRYPEDVYFNG

NPWYLATFAAAEQLYDSVYVWKKTGSITVTSTSSAFFQELVPGVAAGTYSSSQSTFTSIINAISTYADGF

LSEAAKYVPADGSLAEQFDRNTGTPLSAVHLTWSYASFLTAAARRAGVVPPSWASSGANTVPSSCSGASV

VGSYSRPTATSFPPSQTPKPGVPSGTPFTPIPCATPTSVAVTFHELATTQFGQTIKVAGSAPELGNWSTS

AAIALDAVNYATNHPLWIGSVNLEAGDVIEYKYINVGQDGSVTWESDPNHTYTVPAVACVTEVVKEDTWQ

S (full-length GA from *Trichoderma* sp.; SQN10 of U.S. Pat. No. 7,413,879)
SEQ ID NO: 9
MHVLSTAVLLGSVAVQKVLGRPGSSGLYDVTKRSVDDFISTETPIALNNLLCNVGPDGCRAFGTSAGAVI

ASPSTTDPDYYYMWTRDSALVFKNLVDRFTEEYDAGLQRRIEQYITAQVTLQGLTNPSGSLSDGSGLGEP

KFELTLQPFTGNWGRPQRDGPALRAIALIGYAKWLINNNYQSTVSSVIWPIVRNDLNYVAQYWNQTGFDL

WEEVDGSSFFTVANQHRALVEGATLVATLGQSGDTYSSVAPQVLCFLQRFWVSSGGYIDSNINTNEGRTG

KDANSILTSIHTFDPNLGCDAGTFQPCSDKALSNLKVVVDSFRSIYSLNKGIPAGAAVAIGRYPEDVYFN

GNPWYLATFAAAEQLYDAVYVWKETGSITVTATSLAFFQELVPGVTAGTYSSSSSSTFTTIINAVSTYAD

GFLSEAAKYVPADGSLAEQFDRNNGTALSARHLTWSYASFLTATARRAGVVPPSWANSSASTIPSTCSGA

SVVGSYSRPTATSFPPSQTPKPGVPSGTPYTPLPCATPTSVAVTFHELVSTQFGQTVKVAGSAQALGNWS

TSAAVALDAVNYADNHPLWIGTVNLEAGDVVEYKYINVGQDGSVTWESDPNHTYTVPAVACVTQVVKEDT

WQS (full-length GA from *Hypocrea gelatinosa*; SQN12 of U.S. Pat. No. 7,413,879)
SEQ ID NO: 10
MHVLSTAVLLGSVAVQKVLGRPGSNGLSGVTKRSVDDFINTQTPIALNNLLCNVGPDGCRAFGTSAGAVI

ASPSTTDPDYYYMWTRDSALVFKNIVDRFTQQYDAGLQRRIEQYISAQVTLQGPSNPSGSLSDGSGLGEP

KFELTLSQFTGNWGRPQRDGPALRAIALIGYSKWLINNNYQSTVSSIIWPIVRNDLNYVAQYWNQTGFDL

WEEVNGSSFFTVANQHRALVEGATLAATLGQSGSTYSSVAPQILCFLQRFWVSGGYIDSNINSNDGRTGK

DANSLLASIHTFDPSLGCDASTFQPCSDKALSNLKVVVDSFRSIYGVNKGISAGSAVAIGRYPEDVYFNG

NPWYLATFAAAEQLYDSVYVWKKTGSITVTSTSLAFFQELVPGVAAGTYSSSQSTFTSIVNAVSTYADGF

-continued

LSEAAKYVPADGSLAEQFDRNTGTPLSAVHLTWSYASFFTAAARRSGVVPPSWASSGANSIPATCSGASV

VGSYSSPTATSFPPSQTPKPGVPSGTPFTPLPCATPTSVAVTFHELATTQFGQNIKVAGSAPELGNWSTS

AAIALDAVNYATNHPLWIGSVNLEAGDVIEYKYINVGQDGSVTWESDPNHTYTVPAVACVTEVVKEDTWQ

S (full-length GA from *Hypocrea orientalis*; SQN14 of U.S. Pat. No. 7,413,879)
SEQ ID NO: 11
MHVLSTAVLLGSVAVQKVLGRPGSSGLSDVTKRSVDDFISTETPIALNNLLCNVGPDGCRAFGTSAGAVI

ASPSTIDPDYYYMWTRDSALVFKNLVDRFTETYDAGLQRRIEQYITAQVTLQGLSNPSGSLTDGSGLGEP

KFELTLQPFTGNWGRPQRDGPALRAIALIGYSKWLINNNYQSTVSNVIWPIVRNDLNYVAQYWNQTGFDL

WEEVKGSSFFTIANQHRALVEGATLAATLGQSGSTYSSVAPQILCFLQRFWVSSGGYVDSNINTNEGRTG

KDVNSILTSIHTLDPNLGCDAGTFQPCSDKALSNLKVVVDSFRSIYGVNKGIPAGAAVAIGRYAEDVYFN

GNPWYLATFAAAEQLYDAVYVWKKTGSITVTATSLAFFQELVPGVAAGTYASSSSTFTNIINAVSTYADG

FLSEAAKYVPADGSLAEQFDRNSGTPLSALHLTWSYASFLTATARRAGIVPPSWANSSASTIPSTCSGAS

VVGSYSRPTATSFPPSQTPKPGVPSGTPYTPLPCATPTSVAVTFHELVSTQLGQTVKVAGNAPALGNWST

SAAVALDAVNYADNHPLWIGTVDLEAGDVVEYKYINVGQDGSVTWESDPNHTYTVPAVACVTQVVKEDTW

QS (full-length GA from *Trichoderma konilangbra*; SQN16 U.S. Pat. No. 7,413,879)
SEQ ID NO: 12
MHVLSTAVLLGSVAVQKVLGRPGSSGLSDVTKRSVDDFISTQTPIALNNLLCNVGPDGCRAFGTSAGAVI

ASPSTTDPDYYYMWTRDSALVFKNLVDRFTETYDAGLQRRIEQYIAAQVTLQGLTNPSGSLSDGSGLGEP

KFELTLKPFTGNWGRPQRDGPALRAIALIGYSKWLINNNYQSTVSSLIWPIVRNDLNYVAQYWNQTGFDL

WEEVNGSSFFTTANQHRALVEGATLAATLSQPASTYSSVAPQILCFLQRYWVSSGGYVDSNINTNEGRTG

KDANSILAAIHTFDPNLGRDAGTFQPCSDKALSNLKVVVDSFRSIYGVNKGIPAGAAAAVGRYPEDVYFN

GNPWYLATFAAAEQLYDAIYVWKKTGSITVTAISLAFFQELVPGVAAGTYSSSQSTFTNIINAVSTYADG

FISEAAKYVPADGSLAEQFDRNNGTPLSALHLTWSYASFLTATARRAGIVPPSWANSSASSIPSTCSGAS

VVGSYSRPTATSFPPSQTPKPGVPSGTPYTPLPCATPASVAVTFHELVSTQLGQTVKVAGSAPALGNWST

SAAVALDAVNYADNHPLWIGSVELEAGDVVEYKYINVGQDGSVTWESDPNHTYTVPAVACVTQVVKEDTW

QS (full-length GA from *Trichoderma sp.*; SQN29 U.S. Pat. No. 7,413,879)
SEQ ID NO: 13
MHVLSTAVLLGSVAVQKVLGRPGASDITKRAVTDFINSETPIALNNLICNVGPDGCRAFGTSIGAVVASP

STTDPDYFYMWTRDSALVFKTLVDRFTQKYDAGLQRRIEQYIAAQVTLQGISNPSGSLSDGSGLGEPKFE

LTLSQFTGNWGRPQRDGPALRAIALIGYSKWLISNNYQSTVSNIIWPIVRNDLNYVAQYWNQTGFDLWEE

VNGSSFFAVANQHRALVEGATLATTLGQSGSSYSTVAPQILCFLQKFWSPSGYVISNINSNDGRTGKDSN

SILTSIHTFDPSIGCDAATFQPCSDKALSNLKVYVDSFRSIYGVNSGIPAGTAVAVGRYPEDVYFNGNPW

YLSTFAVAEQLYDALYVWKKTGSITVTSTSLAFFQELVPSVTAGTYASSSSTFTSIVNAVSTYADGFVSE

AAKYVPSDGSLSEQFDKNTGTPLSAVHLTWSYASFLTATTRRAGIVPPSWISSGANTVPSSCSGTTVAGS

YSSPTATSFPPSQTPKTAATGTSFTPIACATPTSVAVTFHELATTVPGQTIKVVGNAQALGNWSTSAGVA

LNAVNCASNHPLWIGPVNLKAGDVVEYKYINVGSDGSVTWEADPNHTYTVPAVACVTAVVKEDTWQS (full-length GA from *Trichoderma harzianum*; SQN31 U.S. Pat. No. 7,413,879)
SEQ ID NO: 14
MHVLSTAVLLGSVAVQKVLGRPGSNGLSGVTKRSVDDSINTQTPIALNNLLCNVGPDGCRAFGTSAGAVI

ASPSTTDPDYYYMWTRDSALVFKNIVDRFTEQYDAGLQRRIEQYISAQVTLQGISNPSGSLSDGSGLGEP

KFELTLSQFTGNWGRPQRDGPALRAIALIGYSKWLINNNYQSTVSNIIWPIVRNDLNYVAQYWNQTGFDL

-continued

WEEVNGSSFFTVANQHRALVEGATLAATLGQSGSTYSSVAPQILCFLQRFWVSGGYIDSNINTNEGRTGK
DANSLLASIHTFDPSLGCDASTFQPCSDKALSNLKVVVDSFRSIYSVNKGIPAGAAVAVGRYPEDVYFNG
NPWYLATFAAAEQLYDSVYVWKKTGSITVTSTSLAFFQELVPGVAAGTYSSSQSTFTSIINAVSTYADGF
LSEAAKYVPADGSLAEQFDRNTGTPLSAVHLTWSYASFLTAAARRAGVVPPSWASSGANSVPSSCSGASV
VGSYSRPTATSFPPSQTPKPGAPSGAPFTPIPCATPASVAVTFHELATTQFGQTIKVAGSAPELGNWSTS
AAIALDAVNYATNHPLWIGSVNLEAGDVIEYKYISVGQDGSVTWESDPNHTYTVPAVACVTEVVKEDTWQ
S (full-length GA from *Trichoderma longibrachiatum*; SQN33 U.S. Pat. No.
7,413,879)

SEQ ID NO: 15

MHVLSTAVLLGSVAVQKVLGRPGSSGLSDVTKRSVDDFISTETPIALNNLLCNVGPDGCRAFGTSAGAVI
ASPSTIDPDYYYMWTRDSALVFKNLVDRFTETYDAGLQRRIEQYITAQVTLQGLSNPSGSLTDGSGLGEP
KFELTLKPFTGNWGRPQRDGPALRAVALIGYSKWLINNNYQSTVSNVIWPIVRNDLNYVAQYWNQTGFDL
WEEVNGSSFFTMANQHRALVEGATLAATLGQSGSTYSSVAPQILCFLQRFWVSSGGYVDSNINTNEGRTG
KDVNSVLTSIHTFDPNLGCDAATFQPCSDKALSNLKVVVDSFRSIYGVNKGIPAGAAVAIGRYAEDVYFN
GNPWYLATFAAAEQLYDAIYVWKKTGSITVTATSLAFFQELVPGVAAGTYASSSSTFTNIINAVSTYADG
FLSEAAKYVPADGSLAEQFDRNSGTPLSALHLTWSYASFLTATARRAGIVPPSWANSSASTIPSTCSGAS
VVGSYSRPTATSFPPSQTPKPGVPSGTPYTPLPCATPTSVAVTFHELVSTQFGQTVKVAGNAPALGNWSA
SAAVALDAINYADNHPLWIGTVDLEAGDVVEYKYINVGQDGSVTWESDPNHTYTVPAVACVTQVVKEDTW
QS (full-length GA from *Trichoderma asperellum*; SQN35 U.S. Pat. No. 7,413,879)

SEQ ID NO: 16

MHVLSTAVLLGSVAVQKVLGRPGSNGLSGVTKRSVDDFINTQTPIALNNLLCNVGPDGCRAFGTSAGAVI
ASPSTTDPDYYYMWTRDSALVFKNIVDRFTQQYDAGLQRRIEQYISAQVTLQGISNPSGSLSDGSGLGEP
KFELTLSQFTGNWGRPQRDGPALRAIALIGYSKWLINNNYQSTVSNIIWPIVRNDLNYVAQYWNQTGFDL
WEEVNGSSFFTVANQHRALVEGATLAATLGQSGSTYSSVAPQILCFLQRFWVSGGYIDSNINTNEGRTGK
DANSLLASIHTFDPSLGCDASTFQPCSDKALSNLKVVVDSFRSIYGVNKGIPAGSAVAIGRYPEDVYFNG
NPWYLATFAAAEQLYDSVYVWKKTGSITVTSTSLAFFQELVPGVAAGTYSSSQSTFTSIINAVSTYADGF
LSEAAKYVPADGSLAEQFDRNTGTPLSAVHLTWSYASFLTAAARRAGVVPPSWASSGANSVPSSCSGASV
VGSYSRPTATSFPPSQTPKPGVPSGTPFTPIPCATPTSVAVTFHELATTQFGQTIKVAGSAPELGNWSTS
AAIALDAVNYATNHPLWIGSVSLEAGDVIEYKYINVGQDGSVTWESDPNHTYTVPAVACVTEVVKEDTWQ
S (full-length GA from *Trichoderma strictipilis*; SQN37 U.S. Pat. No. 7,413,879)

SEQ ID NO: 17

MHVLSTAVLLGSVAVQKVLGRPGSSGLSDITKRSVDDFISTQTPIALNNLLCNVGPDGCRAFGTSAGAVI
ASPSTTDPDYYYMWTRDSALVFKNLVDRFTETYDAGLQRRIEQYITAQVTLQGLTNPSGSLADGSGLGEP
KFELTLSPFTGNWGRPQRDGPALRAIALIGYSKWLINNNYQSTVSNVIWPIVRNDLSYAAQYWNQTGFDL
WEEVSGSSFFTVANQHRALVEGATLAATLGQSGSTYSSVAPQILCFLQRFWVSSGGYVDSNINTNEGRTG
KDVNSILTSIHTFDPNLGCDAGTFQPCSDKALSNFKVVVDSFRSIYGVNNGIPAGAAVAIGRYPEDVYFN
GNPWYLATFAAAEQLYDAIYVWKKTGSITVTAISLAFFQELVPGVTAGTYSSSQSTFTNIINAASTYADG
FVTEAAKYVPTDGSLAEQFDRNNGTPLSALHLTWSYASFLTASARRAGVVPPSWANSSASSISSTCSGAS
VVGSYSSPTATSFPPSQTPKPGVPSGTPYTPLPCATPTSVAVTFHELVSTQFGQTVKAAGSAPALGNWST
SAAVGLDAVNYADNHPLWIGTVELEAGDVVEYKYINVGQDGSVTWESDPNHTYTVPAVACVTEVVKEDTW

-continued

QS (full-length GA from *Trichoderma virens* Gv29-8; EHK25059.1)

SEQ ID NO: 18

MHVLSTAVLLGSVAVQKVLGRPGSNGLSDITKRSVDSFISAETPIALNNLLCNVGPDGCRAFGTSAGAVI
ASPSTVDPDYYYMWTRDSALVFKNIVDRFTQKYDAGLQRRIEQYISAQVTLQGISNPSGSLSDGSGLGEP
KFELTLNQFTGNWGRPQRDGPALRAIALIGYSKWLINNNYQSTVSSVIWPIVKNDLNYVAQYWNQTGFDL
WEEVNGSSFFTVANQHRALVEGATLATTLGQSGSTYSSVAPQILCFLQRFWVSGSYIDSNINVNEGRTGK
DANSLLASIHTFDPSLGCDASTFQPCSDKALSNLKVVVDSFRSIYGVNSGISASSAVAIGRYPEDVYFNG
NPWYLATFAAAEQLYDALYVWKQAGSITVTSTSLAFFQQLVPGVAAGTYSSSQSTYTSIINAVSAYADGF
MNEAAKYVPADGSLAEQFDKNSGTPLSAVHLTWSYASFLTAADRRAGIVPSSWASSGANTVPSSCSGASV
VGSYSRPTATSFPPSQTPKPGVPSGTPFTPIPCATPTSVAVTFHELATTQFGQTIKVVGSVPELGNWSTN
AAVALNAVNYASNHPLWLGSINLAAGEVVQYKYINVGSDGSVTWESDPNHTYTVPAVACVTQVVKEDTWQ
S (full-length GA from *Trichoderma atroviride* IMI 206040; EHK49034.1)

SEQ ID NO: 19

MHVLSTAVLLGSVAVQKVLGRPGASDITKRAVTDFINSETPIALNNLICNVGPDGCRAFGTSIGAVVASP
STTDPDYFYMWTRDSALVFKTLVDRFTQNYDAGLQRRIEQYIAAQVTLQGISNPSGSLSDGSGLGEPKFE
LTLSQFTGNWGRPQRDGPALRAIALIGYSKWLISNNYQSTVSNIIWPIVRNDLNYVAQYWNQTGFDLWEE
VNGSSFFTVANQHRALVEGATLATTLGQSGSSYSTVAPQILCFLQKFWSPSGYVISNINSNDGRTGKDSN
SILTSIHTFDPSIGCDAATFQPCSDKALSNLKVYVDSFRSIYGVNSGIPAGTAVAVGRYPEDVYFNGNPW
YLSTFAVAEQLYDALYVWKKTGSITVTSTSLAFFQELVPSVTAGTYASSSSTFTSIVNAVSTYADGFVSE
AAKYVPSDGSLSEQFDKNTGTPLSAVHLTWSYASFLTATARRAGIVPPSWISSGANTVPSSCSGTTVAGS
YSSPTATSFPPSQTPKTAATGTSFTPIACATPTSVAVTFHELATTVPGQTIKVVGNAQALGNWSTSAGVA
LNAVNYASNHPLWIGPVNLKAGDVVEYKYINVGSDGSVTWEADPNHTYTVPAVACVTAVVKEDTWQS

---

What is claimed is:

1. A glucoamylase variant comprising amino acid substitutions corresponding to positions: 50, 417, 430, 511, 539, and 563 of SEQ ID NO: 2, wherein the glucoamylase variant has at least 90% sequence identity with SEQ ID NO: 2, and wherein the amino acid substitution at position 50 is M50Y, G, F, or K.

2. The glucoamylase variant of claim 1, wherein the amino acid substitution at position 50 is M50Y.

3. The glucoamylase variant of claim 1, wherein the amino acid substitutions at positions 417, 430, 511, 539, and 563 are: L417V, T430A, Q511H, A539R, and N563I, respectively.

4. The glucoamylase variant of claim 1, wherein the glucoamylase variant has at least 95%, 97%, or 99% sequence identity with SEQ ID NO: 2.

5. The glucoamylase variant of claim 1, wherein the glucoamylase variant comprises the amino acid sequence of SEQ ID NO: 6.

6. The glucoamylase variant of claim 1, wherein the glucoamylase variant consists of the amino acid sequence of SEQ ID NO: 6.

7. The glucoamylase variant of claim 1 further comprising one or more additional amino acid substitutions corresponding to positions: 43, 44, 61, 73, 294, 431, 503, or 535 of SEQ ID NO: 2.

8. The glucoamylase variant of claim 7, wherein the amino acid substitutions are: I4Q/R3, D44C/R, N61I, G73F, G294C, A431L/Q, E503A/V, or A535R of SEQ ID NO: 2.

9. The glucoamylase variant of claim 1, wherein the glucoamylase variant exhibits increased thermostability or increased specific activity as compared to a glucoamylase comprising the amino acid sequence of SEQ ID NO: 2.

10. The glucoamylase variant of claim 1, wherein the glucoamylase variant loses less activity upon oxidation, when compared to a second glucoamylase variant comprising the amino acid sequence of SEQ ID NO: 5 under the same conditions.

11. An enzyme composition comprising the glucoamylase variant of claim 1.

12. The enzyme composition of claim 11, further comprising a hexokinase, a xylanase, a glucose isomerase, a xylose isomerase, a phosphatase, a phytase, a pullulanase, a β-amylase, an α-amylase, a protease, a cellulase, a hemicellulase, a lipase, a cutinase, a trehalase, an isoamylase, a redox enzyme, an esterase, a transferase, a pectinase, a lyase, an α-glucosidase, a β-glucosidase, or a combination thereof.

13. A method of processing starch comprising contacting a starch substrate with the glucoamylase variant of claim 1 to produce a composition comprising glucose.

14. The method of claim 13, further comprising adding a hexokinase, a xylanase, a glucose isomerase, a xylose isomerase, a phosphatase, a phytase, a pullulanase, a β-amylase, an α-amylase, a protease, a cellulase, a hemicellulase, a lipase, a cutinase, a trehalase, an isoamylase, a redox enzyme, an esterase, a transferase, a pectinase, a hydrolase, an alpha-glucosidase, an beta-glucosidase, or a combination thereof to the starch substrate.

15. The method of claim 13, wherein processing starch comprises saccharifying the starch substrate resulting in a high glucose syrup.

16. The method of claim 13, further comprising fermenting the composition comprising glucose to an end product.

17. The method of claim 15, wherein saccharifying and fermenting are carried out as a simultaneous saccharification and fermentation (SSF) process.

18. The method of claim 16, wherein the end product is an alcohol.

19. The method of claim 18, wherein the end product is ethanol.

20. The method of claim 16, wherein the end product is citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, lysine, itaconic acid, 1,3-propanediol, biodiesel, or isoprene.

21. The method of claim 13, wherein the starch substrate is about 15% to 50% dry solid (DS).

22. The method of claim 13, wherein the glucoamylase is dosed at a range of about 0.2 to about 1.0 glucoamylase unit (GAU) per gram of dry solid starch (dss).

23. The method of claim 13, wherein the starch substrate is wheat, barley, corn, rye, rice, sorghum, bran, cassava, milo, millet, potato, sweet potato, tapioca, or any combination thereof.

24. The method of claim 13, wherein the starch substrate comprises liquefied starch, gelatinized starch, or granular starch.

* * * * *

SEQUENCE LISTING

<160> NUMBER OF SEQ ID NOS: 19

<210> SEQ ID NO 1
<211> LENGTH: 632
<212> TYPE: PRT
<213> ORGANISM: Trichoderma reesei
<220> FEATURE:
<221> NAME/KEY: misc_feature
<222> LOCATION: (1)..(632)
<223> OTHER INFORMATION: full-length TrGA, w/ signal peptide and
      prosequence

<400> SEQUENCE: 1

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Ile

-continued

```
                      85                  90                  95
Asp Arg Phe Thr Glu Thr Tyr Asp Ala Gly Leu Gln Arg Ile Glu
                 100                 105                 110

Gln Tyr Ile Thr Ala Gln Val Thr Leu Gln Gly Leu Ser Asn Pro Ser
             115                 120                 125

Gly Ser Leu Ala Asp Gly Ser Gly Leu Gly Glu Pro Lys Phe Glu Leu
130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                 165                 170                 175

Asn Asn Asn Tyr Gln Ser Thr Val Ser Asn Val Ile Trp Pro Ile Val
             180                 185                 190

Arg Asn Asp Leu Asn Tyr Val Ala Gln Tyr Trp Asn Gln Thr Gly Phe
             195                 200                 205

Asp Leu Trp Glu Glu Val Asn Gly Ser Ser Phe Phe Thr Val Ala Asn
210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
                 245                 250                 255

Leu Gln Arg Phe Trp Val Ser Ser Gly Gly Tyr Val Asp Ser Asn Ile
             260                 265                 270

Asn Thr Asn Glu Gly Arg Thr Gly Lys Asp Val Asn Ser Val Leu Thr
             275                 280                 285

Ser Ile His Thr Phe Asp Pro Asn Leu Gly Cys Asp Ala Gly Thr Phe
290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                 325                 330                 335

Ala Val Ala Ile Gly Arg Tyr Ala Glu Asp Val Tyr Tyr Asn Gly Asn
             340                 345                 350

Pro Trp Tyr Leu Ala Thr Phe Ala Ala Ala Glu Gln Leu Tyr Asp Ala
             355                 360                 365

Ile Tyr Val Trp Lys Lys Thr Gly Ser Ile Thr Val Thr Ala Thr Ser
             370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
                 405                 410                 415

Tyr Ala Asp Gly Phe Leu Ser Glu Ala Ala Lys Tyr Val Pro Ala Asp
             420                 425                 430

Gly Ser Leu Ala Glu Gln Phe Asp Arg Asn Ser Gly Thr Pro Leu Ser
             435                 440                 445

Ala Leu His Leu Thr Trp Ser Tyr Ala Ser Phe Leu Thr Ala Thr Ala
450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                 485                 490                 495

Arg Pro Thr Ala Thr Ser Phe Pro Pro Ser Gln Thr Pro Lys Pro Gly
             500                 505                 510
```

```
Val Pro Ser Gly Thr Pro Tyr Thr Pro Leu Pro Cys Ala Thr Pro Thr
            515                 520                 525

Ser Val Ala Val Thr Phe His Glu Leu Val Ser Thr Gln Phe Gly Gln
530                 535                 540

Thr Val Lys Val Ala Gly Asn Ala Ala Ala Leu Gly Asn Trp Ser Thr
545                 550                 555                 560

Ser Ala Ala Val Ala Leu Asp Ala Val Asn Tyr Ala Asp Asn His Pro
            565                 570                 575

Leu Trp Ile Gly Thr Val Asn Leu Glu Ala Gly Asp Val Val Glu Tyr
            580                 585                 590

Lys Tyr Ile Asn Val Gly Gln Asp Gly Ser Val Thr Trp Glu Ser Asp
            595                 600                 605

Pro Asn His Thr Tyr Thr Val Pro Ala Val Ala Cys Val Thr Gln Val
            610                 615                 620

Val Lys Glu Asp Thr Trp Gln Ser
625                 630

<210> SEQ ID NO 2
<211> LENGTH: 599
<212> TYPE: PRT
<213> ORGANISM: Trichoderma reesei
<220> FEATURE:
<221> NAME/KEY: misc_feature
<222> LOCATION: (1)..(599)
<223> OTHER INFORMATION: mature TrGA, w/o signal peptide and prosequence

<400> SEQUENCE: 2

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
            35                  40                  45

Tyr Met Trp Thr Arg Asp Ser Ala Leu Val Phe Lys Asn Leu Ile Asp
        50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
            115                 120                 125

Ala Leu Arg Ala Ile Ala Leu Ile Gly Tyr Ser Lys Trp Leu Ile Asn
            130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
            195                 200                 205

Ser Gly Ser Ala Tyr Ser Ser Val Ala Pro Gln Val Leu Cys Phe Leu
            210                 215                 220
```

```
Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
            245                 250                 255

Ile His Thr Phe Asp Pro Asn Leu Gly Cys Asp Ala Gly Thr Phe Gln
        260                 265                 270

Pro Cys Ser Asp Lys Ala Leu Ser Asn Leu Lys Val Val Asp Ser
    275                 280                 285

Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Glu Gln Leu Tyr Asp Ala Ile
                325                 330                 335

Tyr Val Trp Lys Lys Thr Gly Ser Ile Thr Val Thr Ala Thr Ser Leu
                340                 345                 350

Ala Phe Phe Gln Glu Leu Val Pro Gly Val Thr Ala Gly Thr Tyr Ser
        355                 360                 365

Ser Ser Ser Ser Thr Phe Thr Asn Ile Ile Asn Ala Val Ser Thr Tyr
370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
            405                 410                 415

Leu His Leu Thr Trp Ser Tyr Ala Ser Phe Leu Thr Ala Thr Ala Arg
        420                 425                 430

Arg Ala Gly Ile Val Pro Pro Ser Trp Ala Asn Ser Ser Ala Ser Thr
            435                 440                 445

Ile Pro Ser Thr Cys Ser Gly Ala Ser Val Val Gly Ser Tyr Ser Arg
        450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
            485                 490                 495

Val Ala Val Thr Phe His Glu Leu Val Ser Thr Gln Phe Gly Gln Thr
                500                 505                 510

Val Lys Val Ala Gly Asn Ala Ala Ala Leu Gly Asn Trp Ser Thr Ser
            515                 520                 525

Ala Ala Val Ala Leu Asp Ala Val Asn Tyr Ala Asp Asn His Pro Leu
530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
            580                 585                 590

Lys Glu Asp Thr Trp Gln Ser
            595

<210> SEQ ID NO 3
<211> LENGTH: 20
<212> TYPE: PRT
<213> ORGANISM: Trichoderma reesei
<220> FEATURE:
<221> NAME/KEY: misc_feature
```

-continued

```
<222> LOCATION: (1)..(20)
<223> OTHER INFORMATION: signal peptide of wild type TrGA

<400> SEQUENCE: 3

Met His Val Leu Ser Thr Ala Val Leu Leu Gly Ser Val Ala Val Gln
1               5                   10                  15

Lys Val Leu Gly
            20

<210> SEQ ID NO 4
<211> LENGTH: 1899
<212> TYPE: DNA
<213> ORGANISM: Trichoderma reesei
<220> FEATURE:
<221> NAME/KEY: misc_feature
<222> LOCATION: (1)..(1899)
<223> OTHER INFORMATION: cDNA of wild type TrGA

<400> SEQUENCE: 4
atgcacgtcc tgtcgactgc ggtgctgctc ggctccgttg ccgttcaaaa ggtcctggga      60
agaccaggat caagcggtct gtccgacgtc accaagaggt ctgttgacga cttcatcagc     120
accgagacgc ctattgcact gaacaatctt ctttgcaatg ttggtcctga tggatgccgt     180
gcattcggca catcagctgg tgcggtgatt gcatctccca gcacaattga cccggactac     240
tattacatgt ggacgcgaga tagcgctctt gtcttcaaga acctcatcga ccgcttcacc     300
gaaacgtacg atgcgggcct gcagcgccgc atcgagcagt acattactgc ccaggtcact     360
ctccagggcc tctctaaccc ctcgggctcc ctcgcggacg gctctggtct cggcgagccc     420
aagtttgagt tgaccctgaa gccttttcacc ggcaactggg gtcgaccgca gcgggatggc     480
ccagctctgc gagccattgc cttgattgga tactcaaagt ggctcatcaa caacaactat     540
cagtcgactg tgtccaacgt catctggcct attgtgcgca acgacctcaa ctatgttgcc     600
cagtactgga ccaaaccgg cttttgacctc tgggaagaag tcaatgggag ctcattcttt     660
actgttgcca ccagcaccg agcacttgtc gagggcgcca ctcttgctgc cactcttggc     720
cagtcgggaa gcgcttattc atctgttgct ccccaggttt gtgctttct ccaacgattc     780
tgggtgtcgt ctggtggata cgtcgactcc aacatcaaca ccaacgaggg caggactggc     840
aaggatgtca actccgtcct gacttccatc cacaccttcg atcccaacct ggctgtgac      900
gcaggcacct tccagccatg cagtgacaaa gcgctctcca acttcaaggt tgttgtcgac     960
tccttccgct ccatctacgg cgtgaacaag ggcattcctg ccggtgctgc cgtcgccatt    1020
ggccggtatg cagaggatgt gtactacaac ggcaacccct tggtatcttg cacatttgct    1080
gctgccgagc agctgtacga tgccatctac gtctggaaga agacgggctc catcacggtg    1140
accgccacct cccctggcct tcttccaggag cttgttcctg gcgtgacggc cgggacctac    1200
tccagcagct cttcgaccct taccaacatc atcaacgccg tctcgacata cgccgatggc    1260
ttcctcagcg aggctgccaa gtacgtcccc gccgacggtt cgctggccga cagtttgac     1320
cgcaacagcg gcactccgct gtctgcgctt cacctgacgt ggtcgtacgc ctcgttcttg    1380
acagccacgg cccgtcgggc tggcatcgtg cccccctcgt gggccaacag cagcgctagc    1440
acgatcccct cgacgtgctc cggcgcgtcc gtggtcggat cctactcgcg tcccaccgcc    1500
acgtcattcc ctcgtcgca gacgcccaag cctggcgtgc cttccggtac tccctacacg    1560
cccctgcct gcgcgacccc aacctccgtg gccgtcacct tccacgagct cgtgtcgaca    1620
cagtttggcc agacggtcaa ggtggcgggc aacgccgcgg ccctgggcaa ctggagcacg    1680
```

```
agcgccgccg tggctctgga cgccgtcaac tatgccgata accaccccct gtggattggg    1740
acggtcaacc tcgaggctgg agacgtcgtg gagtacaagt acatcaatgt gggccaagat    1800
ggctccgtga cctgggagag tgatcccaac cacacttaca cggttcctgc ggtggcttgt    1860
gtgacgcagg ttgtcaagga ggacacctgg cagtcgtaa                           1899
```

<210> SEQ ID NO 5
<211> LENGTH: 599
<212> TYPE: PRT
<213> ORGANISM: Artificial Sequence
<220> FEATURE:
<223> OTHER INFORMATION: Synthetic mature TrGA variant CS4

<400> SEQUENCE: 5

```
Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
        275                 280                 285

Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
```

```
                    325                 330                 335
Tyr Val Trp Lys Lys Thr Gly Ser Ile Thr Val Thr Ala Thr Ser Leu
                340                 345                 350

Ala Phe Phe Gln Glu Leu Val Pro Gly Val Thr Ala Gly Thr Tyr Ser
                355                 360                 365

Ser Ser Ser Ser Thr Phe Thr Asn Ile Ile Asn Ala Val Ser Thr Tyr
        370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Val His Leu Thr Trp Ser Tyr Ala Ser Phe Leu Thr Ala Ala Ala Arg
                420                 425                 430

Arg Ala Gly Ile Val Pro Pro Ser Trp Ala Asn Ser Ser Ala Ser Thr
                435                 440                 445

Ile Pro Ser Thr Cys Ser Gly Ala Ser Val Val Gly Ser Tyr Ser Arg
        450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Phe Gly His Thr
                500                 505                 510

Val Lys Val Ala Gly Asn Ala Ala Ala Leu Gly Asn Trp Ser Thr Ser
                515                 520                 525

Ala Ala Val Ala Leu Asp Ala Val Asn Tyr Arg Asp Asn His Pro Leu
        530                 535                 540

Trp Ile Gly Thr Val Asn Leu Glu Ala Gly Asp Val Val Glu Tyr Lys
545                 550                 555                 560

Tyr Ile Ile Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
                580                 585                 590

Lys Glu Asp Thr Trp Gln Ser
        595

<210> SEQ ID NO 6
<211> LENGTH: 599
<212> TYPE: PRT
<213> ORGANISM: Artificial Sequence
<220> FEATURE:
<223> OTHER INFORMATION: Synthetic mature TrGA variant CS4 with M50Y

<400> SEQUENCE: 6

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Ile Asp Pro Asp Tyr Tyr
            35                  40                  45

Tyr Tyr Trp Thr Arg Asp Ser Ala Leu Val Phe Lys Asn Leu Ile Asp
        50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
```

```
             85                  90                  95
Ser Leu Ala Asp Gly Ser Gly Leu Gly Glu Pro Lys Phe Glu Leu Thr
            100                 105                 110
Leu Lys Pro Phe Thr Gly Asn Trp Gly Arg Pro Gln Arg Asp Gly Pro
            115                 120                 125
Ala Leu Arg Ala Ile Ala Leu Ile Gly Tyr Ser Lys Trp Leu Ile Asn
            130                 135                 140
Asn Asn Tyr Gln Ser Thr Val Ser Asn Val Ile Trp Pro Ile Val Arg
145                 150                 155                 160
Asn Asp Leu Asn Tyr Val Ala Gln Tyr Trp Asn Gln Thr Gly Phe Asp
                165                 170                 175
Leu Trp Glu Glu Val Asn Gly Ser Ser Phe Phe Thr Val Ala Asn Gln
            180                 185                 190
His Arg Ala Leu Val Glu Gly Ala Thr Leu Ala Ala Thr Leu Gly Gln
            195                 200                 205
Ser Gly Ser Ala Tyr Ser Ser Val Ala Pro Gln Val Leu Cys Phe Leu
            210                 215                 220
Gln Arg Phe Trp Val Ser Ser Gly Gly Tyr Val Asp Ser Asn Ile Asn
225                 230                 235                 240
Thr Asn Glu Gly Arg Thr Gly Lys Asp Val Asn Ser Val Leu Thr Ser
                245                 250                 255
Ile His Thr Phe Asp Pro Asn Leu Gly Cys Asp Ala Gly Thr Phe Gln
            260                 265                 270
Pro Cys Ser Asp Lys Ala Leu Ser Asn Leu Lys Val Val Asp Ser
            275                 280                 285
Phe Arg Ser Ile Tyr Gly Val Asn Lys Gly Ile Pro Ala Gly Ala Ala
290                 295                 300
Val Ala Ile Gly Arg Tyr Ala Glu Asp Val Tyr Tyr Asn Gly Asn Pro
305                 310                 315                 320
Trp Tyr Leu Ala Thr Phe Ala Ala Ala Glu Gln Leu Tyr Asp Ala Ile
                325                 330                 335
Tyr Val Trp Lys Lys Thr Gly Ser Ile Thr Val Thr Ala Thr Ser Leu
                340                 345                 350
Ala Phe Phe Gln Glu Leu Val Pro Gly Val Thr Ala Gly Thr Tyr Ser
                355                 360                 365
Ser Ser Ser Ser Thr Phe Thr Asn Ile Ile Asn Ala Val Ser Thr Tyr
            370                 375                 380
Ala Asp Gly Phe Leu Ser Glu Ala Ala Lys Tyr Val Pro Ala Asp Gly
385                 390                 395                 400
Ser Leu Ala Glu Gln Phe Asp Arg Asn Ser Gly Thr Pro Leu Ser Ala
                405                 410                 415
Val His Leu Thr Trp Ser Tyr Ala Ser Phe Leu Thr Ala Ala Ala Arg
            420                 425                 430
Arg Ala Gly Ile Val Pro Pro Ser Trp Ala Asn Ser Ser Ala Ser Thr
            435                 440                 445
Ile Pro Ser Thr Cys Ser Gly Ala Ser Val Val Gly Ser Tyr Ser Arg
            450                 455                 460
Pro Thr Ala Thr Ser Phe Pro Pro Ser Gln Thr Pro Lys Pro Gly Val
465                 470                 475                 480
Pro Ser Gly Thr Pro Tyr Thr Pro Leu Pro Cys Ala Thr Pro Thr Ser
                485                 490                 495
Val Ala Val Thr Phe His Glu Leu Val Ser Thr Gln Phe Gly His Thr
            500                 505                 510
```

```
Val Lys Val Ala Gly Asn Ala Ala Leu Gly Asn Trp Ser Thr Ser
        515                 520                 525

Ala Ala Val Ala Leu Asp Ala Val Asn Tyr Arg Asp Asn His Pro Leu
530                 535                 540

Trp Ile Gly Thr Val Asn Leu Glu Ala Gly Asp Val Val Glu Tyr Lys
545                 550                 555                 560

Tyr Ile Ile Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
                580                 585                 590

Lys Glu Asp Thr Trp Gln Ser
        595

<210> SEQ ID NO 7
<211> LENGTH: 632
<212> TYPE: PRT
<213> ORGANISM: Hypocrea citrine var. americana
<220> FEATURE:
<221> NAME/KEY: misc_feature
<222> LOCATION: (1)..(632)
<223> OTHER INFORMATION: full-length GA from Hypocrea citrine var.
      americana

<400> SEQUENCE: 7

Met His Val Leu Ser Thr Ala Val Leu Gly Leu Val Ala Val Gln
1               5                   10                  15

Lys Val Leu Gly Arg Pro Gly Leu Asn Gly Val Pro Asp Val Thr Lys
            20                  25                  30

Arg Ser Val Asp Asp Phe Ile Ser Asn Glu Ser Pro Ile Ala Leu Asn
        35                  40                  45

Asn Leu Leu Cys Asn Val Gly Pro Asp Gly Cys Arg Ala Phe Gly Ala
    50                  55                  60

Ser Ala Gly Thr Val Ala Ala Ser Pro Ser Thr Thr Asp Pro Asp Tyr
65                  70                  75                  80

Tyr Tyr Met Trp Thr Arg Asp Ser Ala Leu Ile Phe Lys Thr Val Val
                85                  90                  95

Asp Arg Phe Thr Gln Asn Tyr Asp Ala Ser Leu Gln Lys Arg Ile Glu
            100                 105                 110

Gln Tyr Ile Ala Ala Gln Ala Thr Leu Gln Gly Ile Ser Asn Pro Ser
        115                 120                 125

Gly Ser Leu Ala Asp Gly Ser Gly Leu Gly Glu Pro Lys Phe Glu Leu
    130                 135                 140

Thr Leu Asn Gln Phe Thr Gly His Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asp Asn Asn Tyr Gln Ser Thr Val Ser Asp Ile Ile Trp Pro Ile Leu
            180                 185                 190

Arg Asn Asp Leu Asn Tyr Val Ala Gln Tyr Trp Asn Gln Thr Gly Phe
        195                 200                 205

Asp Leu Trp Glu Glu Val Glu Gly Ser Ser Phe Phe Thr Val Ala Asn
    210                 215                 220

Gln His Arg Ala Leu Val Glu Gly Ala Thr Leu Ala Ala Ile Leu Gly
225                 230                 235                 240

Gln Ser Gly Ser Ser Tyr Ser Ala Val Ala Pro Gln Ile Leu Cys Phe
                245                 250                 255
```

```
Leu Gln Lys Phe Trp Val Ser Ser Gly Gly Tyr Val Asn Ser Asn Ile
            260                 265                 270

Asn Ser Asp Ile Asn Arg Thr Gly Lys Asp Ala Asn Ser Leu Leu Ala
            275                 280                 285

Ser Ile His Thr Phe Asp Pro Ser Ile Gly Cys Asp Pro Ala Thr Phe
            290                 295                 300

Gln Pro Cys Ser Asp Lys Ala Leu Ser Asn Leu Lys Ser Val Val Asp
305                 310                 315                 320

Ser Phe Arg Ser Ile Tyr Gly Val Asn Gln Gly Ile Ser Ala Gly Ser
                325                 330                 335

Ala Val Ala Ile Gly Arg Tyr Ser Glu Asp Val Tyr Phe Asn Gly Asn
            340                 345                 350

Pro Trp Tyr Leu Ala Thr Phe Ala Ala Glu Gln Leu Tyr Asp Ser
            355                 360                 365

Leu Tyr Val Trp Lys Gln Thr Gly Ser Ile Thr Val Thr Ala Ile Pro
    370                 375                 380

Leu Ala Phe Phe Gln Glu Leu Val Pro Gly Val Ala Ala Gly Thr Tyr
385                 390                 395                 400

Leu Ser Ser Gln Ser Thr Phe Thr Ser Ile Val Asn Ala Val Ser Ala
                405                 410                 415

Tyr Ala Asp Gly Phe Leu Asn Glu Ala Ala Lys Tyr Val Pro Ser Asp
            420                 425                 430

Gly Ser Leu Ala Glu Gln Phe Asp Lys Asn Asn Gly Thr Pro Leu Ser
            435                 440                 445

Ala Val His Leu Thr Trp Ser Tyr Ala Ser Phe Leu Thr Ala Thr Ala
            450                 455                 460

Arg Arg Ala Gly Ser Val Pro Pro Ser Trp Ala Asn Ser Asn Ala Thr
465                 470                 475                 480

Ser Ile Pro Thr Ala Cys Ser Gly Thr Ser Val Val Gly Ser Tyr Ser
                485                 490                 495

Ser Pro Thr Ala Thr Ser Phe Pro Pro Ser Gln Thr Pro Lys Val Gly
            500                 505                 510

Lys Pro Thr Gly Thr Pro Phe Pro Ile Pro Cys Ala Thr Pro Thr
            515                 520                 525

Ser Val Ala Val Thr Phe His Glu Leu Pro Thr Thr Gln Phe Gly Gln
530                 535                 540

Thr Ile Lys Leu Ala Gly Ser Ala Glu Ala Leu Gly Asn Trp Ser Thr
545                 550                 555                 560

Gly Ala Ala Val Gly Leu Asp Ala Ala Asn Tyr Ala Ser Asn His Pro
                565                 570                 575

Leu Trp Phe Gly Thr Leu Asn Leu Gln Ala Gly Asp Val Ile Glu Tyr
            580                 585                 590

Lys Tyr Ile Asn Val Gly Lys Asp Gly Ser Val Thr Trp Glu Ser Asp
            595                 600                 605

Pro Asn His Thr Tyr Thr Val Pro Ala Val Ala Cys Val Thr Glu Val
            610                 615                 620

Val Lys Glu Asp Thr Trp Gln Ser
625                 630

<210> SEQ ID NO 8
<211> LENGTH: 631
<212> TYPE: PRT
<213> ORGANISM: Hypocrea vinosa
<220> FEATURE:
```

<221> NAME/KEY: misc_feature
<222> LOCATION: (1)..(631)
<223> OTHER INFORMATION: full-length GA from Hypocrea vinosa

<400> SEQUENCE: 8

```
Met His Val Leu Ser Thr Ala Val Leu Leu Gly Ser Val Ala Val Gln
1               5                   10                  15

Lys Val Leu Gly Arg Pro Gly Ser Asn Gly Leu Ser Gly Val Thr Lys
            20                  25                  30

Arg Ser Val Asp Asp Phe Ile Asn Thr Gln Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Thr Asp Pro Asp Tyr
65                  70                  75                  80

Tyr Tyr Met Trp Thr Arg Asp Ser Ala Leu Val Phe Lys Asn Ile Val
                85                  90                  95

Asp Arg Phe Thr Gln Gln Tyr Asp Ala Gly Leu Gln Arg Ile Glu
            100                 105                 110

Gln Tyr Ile Ser Ala Gln Val Thr Leu Gln Gly Ile Ser Asn Pro Ser
            115                 120                 125

Gly Ser Leu Ser Asp Gly Ser Gly Leu Gly Glu Pro Lys Phe Glu Leu
    130                 135                 140

Thr Leu Ser Gln Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Ile Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Thr Tyr Ser Ser Val Ala Pro Gln Ile Leu Cys Phe
                245                 250                 255

Leu Gln Arg Phe Trp Val Ser Gly Gly Tyr Ile Asp Ser Asn Ile Asn
            260                 265                 270

Thr Asn Glu Gly Arg Thr Gly Lys Asp Ala Asn Ser Leu Leu Ala Ser
        275                 280                 285

Ile His Thr Phe Asp Pro Ser Leu Gly Cys Asp Ala Ser Thr Phe Gln
    290                 295                 300

Pro Cys Ser Asp Lys Ala Leu Ser Asn Leu Lys Val Val Asp Ser
305                 310                 315                 320

Phe Arg Ser Ile Tyr Gly Val Asn Lys Gly Ile Pro Ala Gly Ser Ala
                325                 330                 335

Val Ala Ile Gly Arg Tyr Pro Glu Asp Val Tyr Phe Asn Gly Asn Pro
            340                 345                 350

Trp Tyr Leu Ala Thr Phe Ala Ala Glu Gln Leu Tyr Asp Ser Val
        355                 360                 365

Tyr Val Trp Lys Lys Thr Gly Ser Ile Thr Val Thr Ser Thr Ser Ser
    370                 375                 380

Ala Phe Phe Gln Glu Leu Val Pro Gly Val Ala Ala Gly Thr Tyr Ser
```

```
                385                 390                 395                 400
        Ser Ser Gln Ser Thr Phe Thr Ser Ile Ile Asn Ala Ile Ser Thr Tyr
                        405                 410                 415

Ala Asp Gly Phe Leu Ser Glu Ala Ala Lys Tyr Val Pro Ala Asp Gly
                        420                 425                 430

Ser Leu Ala Glu Gln Phe Asp Arg Asn Thr Gly Thr Pro Leu Ser Ala
                        435                 440                 445

Val His Leu Thr Trp Ser Tyr Ala Ser Phe Leu Thr Ala Ala Arg
                        450                 455                 460

Arg Ala Gly Val Val Pro Pro Ser Trp Ala Ser Ser Gly Ala Asn Thr
        465                 470                 475                 480

Val Pro Ser Ser Cys Ser Gly Ala Ser Val Val Gly Ser Tyr Ser Arg
                        485                 490                 495

Pro Thr Ala Thr Ser Phe Pro Pro Ser Gln Thr Pro Lys Pro Gly Val
                        500                 505                 510

Pro Ser Gly Thr Pro Phe Thr Pro Ile Pro Cys Ala Thr Pro Thr Ser
                        515                 520                 525

Val Ala Val Thr Phe His Glu Leu Ala Thr Thr Gln Phe Gly Gln Thr
                        530                 535                 540

Ile Lys Val Ala Gly Ser Ala Pro Glu Leu Gly Asn Trp Ser Thr Ser
        545                 550                 555                 560

Ala Ala Ile Ala Leu Asp Ala Val Asn Tyr Ala Thr Asn His Pro Leu
                        565                 570                 575

Trp Ile Gly Ser Val Asn Leu Glu Ala Gly Asp Val Ile Glu Tyr Lys
                        580                 585                 590

Tyr Ile Asn Val Gly Gln Asp Gly Ser Val Thr Trp Glu Ser Asp Pro
                        595                 600                 605

Asn His Thr Tyr Thr Val Pro Ala Val Ala Cys Val Thr Glu Val Val
                        610                 615                 620

Lys Glu Asp Thr Trp Gln Ser
        625                 630

<210> SEQ ID NO 9
<211> LENGTH: 633
<212> TYPE: PRT
<213> ORGANISM: Unknown
<220> FEATURE:
<223> OTHER INFORMATION: Trichoderma sp.
<220> FEATURE:
<221> NAME/KEY: misc_feature
<222> LOCATION: (1)..(633)
<223> OTHER INFORMATION: full-length GA from Trichoderma sp.

<400> SEQUENCE: 9

Met His Val Leu Ser Thr Ala Val Leu Leu Gly Ser Val Ala Val Gln
        1               5                   10                  15

Lys Val Leu Gly Arg Pro Gly Ser Ser Gly Leu Tyr Asp Val Thr Lys
                        20                  25                  30

Arg Ser Val Asp Asp Phe Ile Ser Thr Glu Thr Pro Ile Ala Leu Asn
                        35                  40                  45

Asn Leu Leu Cys Asn Val Gly Pro Asp Gly Cys Arg Ala Phe Gly Thr
                        50                  55                  60

Ser Ala Gly Ala Val Ile Ala Ser Pro Ser Thr Thr Asp Pro Asp Tyr
        65                  70                  75                  80

Tyr Tyr Met Trp Thr Arg Asp Ser Ala Leu Val Phe Lys Asn Leu Val
                        85                  90                  95
```

```
Asp Arg Phe Thr Glu Glu Tyr Asp Ala Gly Leu Gln Arg Arg Ile Glu
            100                 105                 110

Gln Tyr Ile Thr Ala Gln Val Thr Leu Gln Gly Leu Thr Asn Pro Ser
        115                 120                 125

Gly Ser Leu Ser Asp Gly Ser Gly Leu Gly Glu Pro Lys Phe Glu Leu
        130                 135                 140

Thr Leu Gln Pro Phe Thr Gly Asn Trp Gly Arg Pro Gln Arg Asp Gly
145                 150                 155                 160

Pro Ala Leu Arg Ala Ile Ala Leu Ile Gly Tyr Ala Lys Trp Leu Ile
                165                 170                 175

Asn Asn Asn Tyr Gln Ser Thr Val Ser Ser Val Ile Trp Pro Ile Val
                180                 185                 190

Arg Asn Asp Leu Asn Tyr Val Ala Gln Tyr Trp Asn Gln Thr Gly Phe
                195                 200                 205

Asp Leu Trp Glu Glu Val Asp Gly Ser Ser Phe Phe Thr Val Ala Asn
        210                 215                 220

Gln His Arg Ala Leu Val Glu Gly Ala Thr Leu Val Ala Thr Leu Gly
225                 230                 235                 240

Gln Ser Gly Asp Thr Tyr Ser Ser Val Ala Pro Gln Val Leu Cys Phe
                245                 250                 255

Leu Gln Arg Phe Trp Val Ser Ser Gly Gly Tyr Ile Asp Ser Asn Ile
                260                 265                 270

Asn Thr Asn Glu Gly Arg Thr Gly Lys Asp Ala Asn Ser Ile Leu Thr
                275                 280                 285

Ser Ile His Thr Phe Asp Pro Asn Leu Gly Cys Asp Ala Gly Thr Phe
        290                 295                 300

Gln Pro Cys Ser Asp Lys Ala Leu Ser Asn Leu Lys Val Val Val Asp
305                 310                 315                 320

Ser Phe Arg Ser Ile Tyr Ser Leu Asn Lys Gly Ile Pro Ala Gly Ala
                325                 330                 335

Ala Val Ala Ile Gly Arg Tyr Pro Glu Asp Val Tyr Phe Asn Gly Asn
                340                 345                 350

Pro Trp Tyr Leu Ala Thr Phe Ala Ala Ala Glu Gln Leu Tyr Asp Ala
        355                 360                 365

Val Tyr Val Trp Lys Glu Thr Gly Ser Ile Thr Val Thr Ala Thr Ser
        370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Thr Ile Ile Asn Ala Val Ser
                405                 410                 415

Thr Tyr Ala Asp Gly Phe Leu Ser Glu Ala Ala Lys Tyr Val Pro Ala
        420                 425                 430

Asp Gly Ser Leu Ala Glu Gln Phe Asp Arg Asn Asn Gly Thr Ala Leu
        435                 440                 445

Ser Ala Arg His Leu Thr Trp Ser Tyr Ala Ser Phe Leu Thr Ala Thr
        450                 455                 460

Ala Arg Arg Ala Gly Val Val Pro Pro Ser Trp Ala Asn Ser Ser Ala
465                 470                 475                 480

Ser Thr Ile Pro Ser Thr Cys Ser Gly Ala Ser Val Val Gly Ser Tyr
                485                 490                 495

Ser Arg Pro Thr Ala Thr Ser Phe Pro Pro Ser Gln Thr Pro Lys Pro
                500                 505                 510

Gly Val Pro Ser Gly Thr Pro Tyr Thr Pro Leu Pro Cys Ala Thr Pro
```

```
                515                 520                 525
Thr Ser Val Ala Val Thr Phe His Glu Leu Val Ser Thr Gln Phe Gly
    530                 535                 540
Gln Thr Val Lys Val Ala Gly Ser Ala Gln Ala Leu Gly Asn Trp Ser
545                 550                 555                 560
Thr Ser Ala Ala Val Ala Leu Asp Ala Val Asn Tyr Ala Asp Asn His
                565                 570                 575
Pro Leu Trp Ile Gly Thr Val Asn Leu Glu Ala Gly Asp Val Val Glu
            580                 585                 590
Tyr Lys Tyr Ile Asn Val Gly Gln Asp Gly Ser Val Thr Trp Glu Ser
        595                 600                 605
Asp Pro Asn His Thr Tyr Thr Val Pro Ala Val Ala Cys Val Thr Gln
    610                 615                 620
Val Val Lys Glu Asp Thr Trp Gln Ser
625                 630

<210> SEQ ID NO 10
<211> LENGTH: 631
<212> TYPE: PRT
<213> ORGANISM: Hypocrea gelatinosa
<220> FEATURE:
<221> NAME/KEY: misc_feature
<222> LOCATION: (1)..(631)
<223> OTHER INFORMATION: full-length GA from Hypocrea gelatinosa

<400> SEQUENCE: 10

Met His Val Leu Ser Thr Ala Val Leu Leu Gly Ser Val Ala Val Gln
1               5                   10                  15
Lys Val Leu Gly Arg Pro Gly Ser Asn Gly Leu Ser Gly Val Thr Lys
            20                  25                  30
Arg Ser Val Asp Asp Phe Ile Asn Thr Gln Thr Pro Ile Ala Leu Asn
        35                  40                  45
Asn Leu Leu Cys Asn Val Gly Pro Asp Gly Cys Arg Ala Phe Gly Thr
    50                  55                  60
Ser Ala Gly Ala Val Ile Ala Ser Pro Ser Thr Thr Asp Pro Asp Tyr
65                  70                  75                  80
Tyr Tyr Met Trp Thr Arg Asp Ser Ala Leu Val Phe Lys Asn Ile Val
                85                  90                  95
Asp Arg Phe Thr Gln Gln Tyr Asp Ala Gly Leu Gln Arg Arg Ile Glu
            100                 105                 110
Gln Tyr Ile Ser Ala Gln Val Thr Leu Gln Gly Pro Ser Asn Pro Ser
        115                 120                 125
Gly Ser Leu Ser Asp Gly Ser Gly Leu Gly Glu Pro Lys Phe Glu Leu
    130                 135                 140
Thr Leu Ser Gln Phe Thr Gly Asn Trp Gly Arg Pro Gln Arg Asp Gly
145                 150                 155                 160
Pro Ala Leu Arg Ala Ile Ala Leu Ile Gly Tyr Ser Lys Trp Leu Ile
                165                 170                 175
Asn Asn Asn Tyr Gln Ser Thr Val Ser Ser Ile Ile Trp Pro Ile Val
            180                 185                 190
Arg Asn Asp Leu Asn Tyr Val Ala Gln Tyr Trp Asn Gln Thr Gly Phe
        195                 200                 205
Asp Leu Trp Glu Glu Val Asn Gly Ser Ser Phe Phe Thr Val Ala Asn
    210                 215                 220
Gln His Arg Ala Leu Val Glu Gly Ala Thr Leu Ala Ala Thr Leu Gly
225                 230                 235                 240
```

Gln Ser Gly Ser Thr Tyr Ser Ser Val Ala Pro Gln Ile Leu Cys Phe
            245                 250                 255

Leu Gln Arg Phe Trp Val Ser Gly Gly Tyr Ile Asp Ser Asn Ile Asn
            260                 265                 270

Ser Asn Asp Gly Arg Thr Gly Lys Asp Ala Asn Ser Leu Leu Ala Ser
            275                 280                 285

Ile His Thr Phe Asp Pro Ser Leu Gly Cys Asp Ala Ser Thr Phe Gln
            290                 295                 300

Pro Cys Ser Asp Lys Ala Leu Ser Asn Leu Lys Val Val Asp Ser
305                 310                 315                 320

Phe Arg Ser Ile Tyr Gly Val Asn Lys Gly Ile Ser Ala Gly Ser Ala
            325                 330                 335

Val Ala Ile Gly Arg Tyr Pro Glu Asp Val Tyr Phe Asn Gly Asn Pro
            340                 345                 350

Trp Tyr Leu Ala Thr Phe Ala Ala Glu Gln Leu Tyr Asp Ser Val
            355                 360                 365

Tyr Val Trp Lys Lys Thr Gly Ser Ile Thr Val Thr Ser Thr Ser Leu
            370                 375                 380

Ala Phe Phe Gln Glu Leu Val Pro Gly Val Ala Ala Gly Thr Tyr Ser
385                 390                 395                 400

Ser Ser Gln Ser Thr Phe Thr Ser Ile Val Asn Ala Val Ser Thr Tyr
            405                 410                 415

Ala Asp Gly Phe Leu Ser Glu Ala Ala Lys Tyr Val Pro Ala Asp Gly
            420                 425                 430

Ser Leu Ala Glu Gln Phe Asp Arg Asn Thr Gly Thr Pro Leu Ser Ala
            435                 440                 445

Val His Leu Thr Trp Ser Tyr Ala Ser Phe Phe Thr Ala Ala Ala Arg
            450                 455                 460

Arg Ser Gly Val Val Pro Pro Ser Trp Ala Ser Ser Gly Ala Asn Ser
465                 470                 475                 480

Ile Pro Ala Thr Cys Ser Gly Ala Ser Val Val Gly Ser Tyr Ser Ser
            485                 490                 495

Pro Thr Ala Thr Ser Phe Pro Pro Ser Gln Thr Pro Lys Pro Gly Val
            500                 505                 510

Pro Ser Gly Thr Pro Phe Thr Pro Leu Pro Cys Ala Thr Pro Thr Ser
            515                 520                 525

Val Ala Val Thr Phe His Glu Leu Ala Thr Thr Gln Phe Gly Gln Asn
            530                 535                 540

Ile Lys Val Ala Gly Ser Ala Pro Glu Leu Gly Asn Trp Ser Thr Ser
545                 550                 555                 560

Ala Ala Ile Ala Leu Asp Ala Val Asn Tyr Ala Thr Asn His Pro Leu
            565                 570                 575

Trp Ile Gly Ser Val Asn Leu Glu Ala Gly Asp Val Ile Glu Tyr Lys
            580                 585                 590

Tyr Ile Asn Val Gly Gln Asp Gly Ser Val Thr Trp Glu Ser Asp Pro
            595                 600                 605

Asn His Thr Tyr Thr Val Pro Ala Val Ala Cys Val Thr Glu Val Val
            610                 615                 620

Lys Glu Asp Thr Trp Gln Ser
625                 630

<210> SEQ ID NO 11
<211> LENGTH: 632

```
<212> TYPE: PRT
<213> ORGANISM: Hypocrea orientalis
<220> FEATURE:
<221> NAME/KEY: misc_feature
<222> LOCATION: (1)..(632)
<223> OTHER INFORMATION: full-length GA from Hypocrea orientalis

<400> SEQUENCE: 11
```

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Val
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Thr Asp Gly Ser Gly Leu Gly Glu Pro Lys Phe Glu Leu
    130                 135                 140

Thr Leu Gln Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Lys Gly Ser Ser Phe Phe Thr Ile Ala Asn
    210                 215                 220

Gln His Arg Ala Leu Val Glu Gly Ala Thr Leu Ala Ala Thr Leu Gly
225                 230                 235                 240

Gln Ser Gly Ser Thr Tyr Ser Ser Val Ala Pro Gln Ile Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Ile Leu Thr
        275                 280                 285

Ser Ile His Thr Leu Asp Pro Asn Leu Gly Cys Asp Ala Gly Thr Phe
    290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Phe Asn Gly Asn
            340                 345                 350

Pro Trp Tyr Leu Ala Thr Phe Ala Ala Ala Glu Gln Leu Tyr Asp Ala
        355                 360                 365

Val Tyr Val Trp Lys Lys Thr Gly Ser Ile Thr Val Thr Ala Thr Ser

```
                370                 375                 380
Leu Ala Phe Phe Gln Glu Leu Val Pro Gly Val Ala Ala Gly Thr Tyr
385                 390                 395                 400

Ala Ser Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
            420                 425                 430

Gly Ser Leu Ala Glu Gln Phe Asp Arg Asn Ser Gly Thr Pro Leu Ser
        435                 440                 445

Ala Leu His Leu Thr Trp Ser Tyr Ala Ser Phe Leu Thr Ala Thr Ala
    450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                485                 490                 495

Arg Pro Thr Ala Thr Ser Phe Pro Pro Ser Gln Thr Pro Lys Pro Gly
            500                 505                 510

Val Pro Ser Gly Thr Pro Tyr Thr Pro Leu Pro Cys Ala Thr Pro Thr
        515                 520                 525

Ser Val Ala Val Thr Phe His Glu Leu Val Ser Thr Gln Leu Gly Gln
    530                 535                 540

Thr Val Lys Val Ala Gly Asn Ala Pro Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Thr Val Asp Leu Glu Ala Gly Asp Val Val Glu Tyr
            580                 585                 590

Lys Tyr Ile Asn Val Gly Gln Asp Gly Ser Val Thr Trp Glu Ser Asp
        595                 600                 605

Pro Asn His Thr Tyr Thr Val Pro Ala Val Ala Cys Val Thr Gln Val
    610                 615                 620

Val Lys Glu Asp Thr Trp Gln Ser
625                 630

<210> SEQ ID NO 12
<211> LENGTH: 632
<212> TYPE: PRT
<213> ORGANISM: Trichoderma konilangbra
<220> FEATURE:
<221> NAME/KEY: misc_feature
<222> LOCATION: (1)..(632)
<223> OTHER INFORMATION: full-length GA from Trichoderma konilangbra

<400> SEQUENCE: 12

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Gln Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Thr Asp Pro Asp Tyr
65                  70                  75                  80

Tyr Tyr Met Trp Thr Arg Asp Ser Ala Leu Val Phe Lys Asn Leu Val
                85                  90                  95
```

-continued

Asp Arg Phe Thr Glu Thr Tyr Asp Ala Gly Leu Gln Arg Arg Ile Glu
            100                 105                 110

Gln Tyr Ile Ala Ala Gln Val Thr Leu Gln Gly Leu Thr Asn Pro Ser
            115                 120                 125

Gly Ser Leu Ser Asp Gly Ser Gly Leu Gly Pro Lys Phe Glu Leu
        130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Ser Leu Ile Trp Pro Ile Val
            180                 185                 190

Arg Asn Asp Leu Asn Tyr Val Ala Gln Tyr Trp Asn Gln Thr Gly Phe
            195                 200                 205

Asp Leu Trp Glu Glu Val Asn Gly Ser Ser Phe Phe Thr Thr Ala Asn
        210                 215                 220

Gln His Arg Ala Leu Val Glu Gly Ala Thr Leu Ala Ala Thr Leu Ser
225                 230                 235                 240

Gln Pro Ala Ser Thr Tyr Ser Ser Val Ala Pro Gln Ile Leu Cys Phe
                245                 250                 255

Leu Gln Arg Tyr Trp Val Ser Ser Gly Gly Tyr Val Asp Ser Asn Ile
            260                 265                 270

Asn Thr Asn Glu Gly Arg Thr Gly Lys Asp Ala Asn Ser Ile Leu Ala
            275                 280                 285

Ala Ile His Thr Phe Asp Pro Asn Leu Gly Arg Asp Ala Gly Thr Phe
        290                 295                 300

Gln Pro Cys Ser Asp Lys Ala Leu Ser Asn Leu Lys Val Val Asp
305                 310                 315                 320

Ser Phe Arg Ser Ile Tyr Gly Val Asn Lys Gly Ile Pro Ala Gly Ala
                325                 330                 335

Ala Ala Ala Val Gly Arg Tyr Pro Glu Asp Val Tyr Phe Asn Gly Asn
            340                 345                 350

Pro Trp Tyr Leu Ala Thr Phe Ala Ala Ala Glu Gln Leu Tyr Asp Ala
        355                 360                 365

Ile Tyr Val Trp Lys Lys Thr Gly Ser Ile Thr Val Thr Ala Ile Ser
        370                 375                 380

Leu Ala Phe Phe Gln Glu Leu Val Pro Gly Val Ala Ala Gly Thr Tyr
385                 390                 395                 400

Ser Ser Ser Gln Ser Thr Phe Thr Asn Ile Ile Asn Ala Val Ser Thr
                405                 410                 415

Tyr Ala Asp Gly Phe Ile Ser Glu Ala Ala Lys Tyr Val Pro Ala Asp
            420                 425                 430

Gly Ser Leu Ala Glu Gln Phe Asp Arg Asn Asn Gly Thr Pro Leu Ser
        435                 440                 445

Ala Leu His Leu Thr Trp Ser Tyr Ala Ser Phe Leu Thr Ala Thr Ala
        450                 455                 460

Arg Arg Ala Gly Ile Val Pro Pro Ser Trp Ala Asn Ser Ser Ala Ser
465                 470                 475                 480

Ser Ile Pro Ser Thr Cys Ser Gly Ala Ser Val Val Gly Ser Tyr Ser
                485                 490                 495

Arg Pro Thr Ala Thr Ser Phe Pro Pro Ser Gln Thr Pro Lys Pro Gly
            500                 505                 510

```
Val Pro Ser Gly Thr Pro Tyr Thr Pro Leu Pro Cys Ala Thr Pro Ala
        515                 520                 525

Ser Val Ala Val Thr Phe His Glu Leu Val Ser Thr Gln Leu Gly Gln
530                 535                 540

Thr Val Lys Val Ala Gly Ser Ala Pro Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Ser Val Glu Leu Ala Gly Asp Val Val Glu Tyr
                580                 585                 590

Lys Tyr Ile Asn Val Gly Gln Asp Gly Ser Val Thr Trp Glu Ser Asp
                595                 600                 605

Pro Asn His Thr Tyr Thr Val Pro Ala Val Ala Cys Val Thr Gln Val
                610                 615                 620

Val Lys Glu Asp Thr Trp Gln Ser
625                 630

<210> SEQ ID NO 13
<211> LENGTH: 627
<212> TYPE: PRT
<213> ORGANISM: Unknown
<220> FEATURE:
<223> OTHER INFORMATION: Trichoderma sp.
<220> FEATURE:
<221> NAME/KEY: misc_feature
<222> LOCATION: (1)..(627)
<223> OTHER INFORMATION: full-length GA from Trichoderma sp.

<400> SEQUENCE: 13

Met His Val Leu Ser Thr Ala Val Leu Leu Gly Ser Val Ala Val Gln
1               5                   10                  15

Lys Val Leu Gly Arg Pro Gly Ala Ser Asp Ile Thr Lys Arg Ala Val
                20                  25                  30

Thr Asp Phe Ile Asn Ser Glu Thr Pro Ile Ala Leu Asn Asn Leu Ile
            35                  40                  45

Cys Asn Val Gly Pro Asp Gly Cys Arg Ala Phe Gly Thr Ser Ile Gly
    50                  55                  60

Ala Val Val Ala Ser Pro Ser Thr Thr Asp Pro Asp Tyr Phe Tyr Met
65                  70                  75                  80

Trp Thr Arg Asp Ser Ala Leu Val Phe Lys Thr Leu Val Asp Arg Phe
                85                  90                  95

Thr Gln Lys Tyr Asp Ala Gly Leu Gln Arg Arg Ile Glu Gln Tyr Ile
                100                 105                 110

Ala Ala Gln Val Thr Leu Gln Gly Ile Ser Asn Pro Ser Gly Ser Leu
            115                 120                 125

Ser Asp Gly Ser Gly Leu Gly Glu Pro Lys Phe Glu Leu Thr Leu Ser
    130                 135                 140

Gln Phe Thr Gly Asn Trp Gly Arg Pro Gln Arg Asp Gly Pro Ala Leu
145                 150                 155                 160

Arg Ala Ile Ala Leu Ile Gly Tyr Ser Lys Trp Leu Ile Ser Asn Asn
                165                 170                 175

Tyr Gln Ser Thr Val Ser Asn Ile Ile Trp Pro Ile Val Arg Asn Asp
                180                 185                 190

Leu Asn Tyr Val Ala Gln Tyr Trp Asn Gln Thr Gly Phe Asp Leu Trp
            195                 200                 205

Glu Glu Val Asn Gly Ser Ser Phe Phe Ala Val Ala Asn Gln His Arg
    210                 215                 220
```

```
Ala Leu Val Glu Gly Ala Thr Leu Ala Thr Thr Leu Gly Gln Ser Gly
225                 230                 235                 240

Ser Ser Tyr Ser Thr Val Ala Pro Gln Ile Leu Cys Phe Leu Gln Lys
            245                 250                 255

Phe Trp Ser Pro Ser Gly Tyr Val Ile Ser Asn Ile Asn Ser Asn Asp
        260                 265                 270

Gly Arg Thr Gly Lys Asp Ser Asn Ser Ile Leu Thr Ser Ile His Thr
        275                 280                 285

Phe Asp Pro Ser Ile Gly Cys Asp Ala Ala Thr Phe Gln Pro Cys Ser
        290                 295                 300

Asp Lys Ala Leu Ser Asn Leu Lys Val Tyr Val Asp Ser Phe Arg Ser
305                 310                 315                 320

Ile Tyr Gly Val Asn Ser Gly Ile Pro Ala Gly Thr Ala Val Ala Val
                325                 330                 335

Gly Arg Tyr Pro Glu Asp Val Tyr Phe Asn Gly Asn Pro Trp Tyr Leu
            340                 345                 350

Ser Thr Phe Ala Val Ala Glu Gln Leu Tyr Asp Ala Leu Tyr Val Trp
        355                 360                 365

Lys Lys Thr Gly Ser Ile Thr Val Thr Ser Thr Leu Ala Phe Phe
370                 375                 380

Gln Glu Leu Val Pro Ser Val Thr Ala Gly Thr Tyr Ala Ser Ser Ser
385                 390                 395                 400

Ser Thr Phe Thr Ser Ile Val Asn Ala Val Ser Thr Tyr Ala Asp Gly
            405                 410                 415

Phe Val Ser Glu Ala Ala Lys Tyr Val Pro Ser Asp Gly Ser Leu Ser
            420                 425                 430

Glu Gln Phe Asp Lys Asn Thr Gly Thr Pro Leu Ser Ala Val His Leu
            435                 440                 445

Thr Trp Ser Tyr Ala Ser Phe Leu Thr Ala Thr Arg Arg Ala Gly
    450                 455                 460

Ile Val Pro Pro Ser Trp Ile Ser Ser Gly Ala Asn Thr Val Pro Ser
465                 470                 475                 480

Ser Cys Ser Gly Thr Thr Val Ala Gly Ser Tyr Ser Ser Pro Thr Ala
            485                 490                 495

Thr Ser Phe Pro Pro Ser Gln Thr Pro Lys Thr Ala Ala Thr Gly Thr
            500                 505                 510

Ser Phe Thr Pro Ile Ala Cys Ala Thr Pro Thr Ser Val Ala Val Thr
        515                 520                 525

Phe His Glu Leu Ala Thr Thr Val Pro Gly Gln Thr Ile Lys Val Val
        530                 535                 540

Gly Asn Ala Gln Ala Leu Gly Asn Trp Ser Thr Ser Ala Gly Val Ala
545                 550                 555                 560

Leu Asn Ala Val Asn Cys Ala Ser Asn His Pro Leu Trp Ile Gly Pro
                565                 570                 575

Val Asn Leu Lys Ala Gly Asp Val Val Glu Tyr Lys Tyr Ile Asn Val
            580                 585                 590

Gly Ser Asp Gly Ser Val Thr Trp Glu Ala Asp Pro Asn His Thr Tyr
        595                 600                 605

Thr Val Pro Ala Val Ala Cys Val Thr Ala Val Val Lys Glu Asp Thr
        610                 615                 620

Trp Gln Ser
625
```

<210> SEQ ID NO 14
<211> LENGTH: 631
<212> TYPE: PRT
<213> ORGANISM: Trichoderma harzianum
<220> FEATURE:
<221> NAME/KEY: misc_feature
<222> LOCATION: (1)..(631)
<223> OTHER INFORMATION: full-length GA from Trichoderma harzianum

<400> SEQUENCE: 14

```
Met His Val Leu Ser Thr Ala Val Leu Leu Gly Ser Val Ala Val Gln
1               5                   10                  15

Lys Val Leu Gly Arg Pro Gly Ser Asn Gly Leu Ser Gly Val Thr Lys
            20                  25                  30

Arg Ser Val Asp Asp Ser Ile Asn Thr Gln Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Thr Asp Pro Asp Tyr
65                  70                  75                  80

Tyr Tyr Met Trp Thr Arg Asp Ser Ala Leu Val Phe Lys Asn Ile Val
                85                  90                  95

Asp Arg Phe Thr Glu Gln Tyr Asp Ala Gly Leu Gln Arg Arg Ile Glu
            100                 105                 110

Gln Tyr Ile Ser Ala Gln Val Thr Leu Gln Gly Ile Ser Asn Pro Ser
        115                 120                 125

Gly Ser Leu Ser Asp Gly Ser Gly Leu Gly Glu Pro Lys Phe Glu Leu
    130                 135                 140

Thr Leu Ser Gln Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Ile Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Thr Tyr Ser Ser Val Ala Pro Gln Ile Leu Cys Phe
                245                 250                 255

Leu Gln Arg Phe Trp Val Ser Gly Gly Tyr Ile Asp Ser Asn Ile Asn
            260                 265                 270

Thr Asn Glu Gly Arg Thr Gly Lys Asp Ala Asn Ser Leu Leu Ala Ser
        275                 280                 285

Ile His Thr Phe Asp Pro Ser Leu Gly Cys Asp Ala Ser Thr Phe Gln
    290                 295                 300

Pro Cys Ser Asp Lys Ala Leu Ser Asn Leu Lys Val Val Asp Ser
305                 310                 315                 320

Phe Arg Ser Ile Tyr Ser Val Asn Lys Gly Ile Pro Ala Gly Ala Ala
                325                 330                 335

Val Ala Val Gly Arg Tyr Pro Glu Asp Val Tyr Phe Asn Gly Asn Pro
            340                 345                 350

Trp Tyr Leu Ala Thr Phe Ala Ala Ala Glu Gln Leu Tyr Asp Ser Val
```

-continued

```
                355                 360                 365
Tyr Val Trp Lys Lys Thr Gly Ser Ile Thr Val Thr Ser Thr Ser Leu
    370                 375                 380
Ala Phe Phe Gln Glu Leu Val Pro Gly Val Ala Ala Gly Thr Tyr Ser
385                 390                 395                 400
Ser Ser Gln Ser Thr Phe Thr Ser Ile Ile Asn Ala Val Ser Thr Tyr
                405                 410                 415
Ala Asp Gly Phe Leu Ser Glu Ala Ala Lys Tyr Val Pro Ala Asp Gly
            420                 425                 430
Ser Leu Ala Glu Gln Phe Asp Arg Asn Thr Gly Thr Pro Leu Ser Ala
        435                 440                 445
Val His Leu Thr Trp Ser Tyr Ala Ser Phe Leu Thr Ala Ala Ala Arg
    450                 455                 460
Arg Ala Gly Val Val Pro Pro Ser Trp Ala Ser Ser Gly Ala Asn Ser
465                 470                 475                 480
Val Pro Ser Ser Cys Ser Gly Ala Ser Val Val Gly Ser Tyr Ser Arg
                485                 490                 495
Pro Thr Ala Thr Ser Phe Pro Pro Ser Gln Thr Pro Lys Pro Gly Ala
            500                 505                 510
Pro Ser Gly Ala Pro Phe Thr Pro Ile Pro Cys Ala Thr Pro Ala Ser
        515                 520                 525
Val Ala Val Thr Phe His Glu Leu Ala Thr Thr Gln Phe Gly Gln Thr
    530                 535                 540
Ile Lys Val Ala Gly Ser Ala Pro Glu Leu Gly Asn Trp Ser Thr Ser
545                 550                 555                 560
Ala Ala Ile Ala Leu Asp Ala Val Asn Tyr Ala Thr Asn His Pro Leu
                565                 570                 575
Trp Ile Gly Ser Val Asn Leu Glu Ala Gly Asp Val Ile Glu Tyr Lys
            580                 585                 590
Tyr Ile Ser Val Gly Gln Asp Gly Ser Val Thr Trp Glu Ser Asp Pro
        595                 600                 605
Asn His Thr Tyr Thr Val Pro Ala Val Ala Cys Val Thr Glu Val Val
    610                 615                 620
Lys Glu Asp Thr Trp Gln Ser
625                 630

<210> SEQ ID NO 15
<211> LENGTH: 632
<212> TYPE: PRT
<213> ORGANISM: Trichoderma longibrachiatum
<220> FEATURE:
<221> NAME/KEY: misc_feature
<222> LOCATION: (1)..(632)
<223

```
Tyr Tyr Met Trp Thr Arg Asp Ser Ala Leu Val Phe Lys Asn Leu Val
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
            115                 120                 125

Gly Ser Leu Thr Asp Gly Ser Gly Leu Gly Glu Pro Lys Phe Glu Leu
130                 135                 140

Thr Leu Lys Pro Phe Thr Gly Asn Trp Gly Arg Pro Gln Arg Asp Gly
145                 150                 155                 160

Pro Ala Leu Arg Ala Val Ala Leu Ile Gly Tyr Ser Lys Trp Leu Ile
            165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
            195                 200                 205

Asp Leu Trp Glu Glu Val Asn Gly Ser Ser Phe Phe Thr Met Ala Asn
            210                 215                 220

Gln His Arg Ala Leu Val Glu Gly Ala Thr Leu Ala Ala Thr Leu Gly
225                 230                 235                 240

Gln Ser Gly Ser Thr Tyr Ser Ser Val Ala Pro Gln Ile Leu Cys Phe
            245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
            275                 280                 285

Ser Ile His Thr Phe Asp Pro Asn Leu Gly Cys Asp Ala Ala Thr Phe
            290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
            325                 330                 335

Ala Val Ala Ile Gly Arg Tyr Ala Glu Asp Val Tyr Phe Asn Gly Asn
            340                 345                 350

Pro Trp Tyr Leu Ala Thr Phe Ala Ala Ala Glu Gln Leu Tyr Asp Ala
            355                 360                 365

Ile Tyr Val Trp Lys Lys Thr Gly Ser Ile Thr Val Thr Ala Thr Ser
            370                 375                 380

Leu Ala Phe Phe Gln Glu Leu Val Pro Gly Val Ala Ala Gly Thr Tyr
385                 390                 395                 400

Ala Ser Ser Ser Ser Thr Phe Thr Asn Ile Ile Asn Ala Val Ser Thr
            405                 410                 415

Tyr Ala Asp Gly Phe Leu Ser Glu Ala Ala Lys Tyr Val Pro Ala Asp
            420                 425                 430

Gly Ser Leu Ala Glu Gln Phe Asp Arg Asn Ser Gly Thr Pro Leu Ser
            435                 440                 445

Ala Leu His Leu Thr Trp Ser Tyr Ala Ser Phe Leu Thr Ala Thr Ala
            450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
            485                 490                 495
```

```
Arg Pro Thr Ala Thr Ser Phe Pro Pro Ser Gln Thr Pro Lys Pro Gly
                500                 505                 510

Val Pro Ser Gly Thr Pro Tyr Thr Pro Leu Pro Cys Ala Thr Pro Thr
        515                 520                 525

Ser Val Ala Val Thr Phe His Glu Leu Val Ser Thr Gln Phe Gly Gln
    530                 535                 540

Thr Val Lys Val Ala Gly Asn Ala Pro Ala Leu Gly Asn Trp Ser Ala
545                 550                 555                 560

Ser Ala Ala Val Ala Leu Asp Ala Ile Asn Tyr Ala Asp Asn His Pro
                565                 570                 575

Leu Trp Ile Gly Thr Val Asp Leu Glu Ala Gly Asp Val Val Glu Tyr
            580                 585                 590

Lys Tyr Ile Asn Val Gly Gln Asp Gly Ser Val Thr Trp Glu Ser Asp
        595                 600                 605

Pro Asn His Thr Tyr Thr Val Pro Ala Val Ala Cys Val Thr Gln Val
    610                 615                 620

Val Lys Glu Asp Thr Trp Gln Ser
625                 630
```

<210> SEQ ID NO 16
<211> LENGTH: 631
<212> TYPE: PRT
<213> ORGANISM: Trichoderma asperellum
<220> FEATURE:
<221> NAME/KEY: misc_feature
<222> LOCATION: (1)..(631)
<223> OTHER INFORMATION: full-length GA from Trichoderma asperellum

<400> SEQUENCE: 16

```
Met His Val Leu Ser Thr Ala Val Leu Leu Gly Ser Val Ala Val Gln
1               5                   10                  15

Lys Val Leu Gly Arg Pro Gly Ser Asn Gly Leu Ser Gly Val Thr Lys
            20                  25                  30

Arg Ser Val Asp Asp Phe Ile Asn Thr Gln Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Thr Asp Pro Asp Tyr
65                  70                  75                  80

Tyr Tyr Met Trp Thr Arg Asp Ser Ala Leu Val Phe Lys Asn Ile Val
                85                  90                  95

Asp Arg Phe Thr Gln Gln Tyr Ala Gly Leu Gln Arg Arg Ile Glu
            100                 105                 110

Gln Tyr Ile Ser Ala Gln Val Thr Leu Gln Gly Ile Ser Asn Pro Ser
        115                 120                 125

Gly Ser Leu Ser Asp Gly Ser Gly Leu Gly Glu Pro Lys Phe Glu Leu
    130                 135                 140

Thr Leu Ser Gln Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Ile Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Val Ala Asn
```

```
        210                 215                 220
Gln His Arg Ala Leu Val Glu Gly Ala Thr Leu Ala Ala Thr Leu Gly
225                 230                 235                 240

Gln Ser Gly Ser Thr Tyr Ser Ser Val Ala Pro Gln Ile Leu Cys Phe
                245                 250                 255

Leu Gln Arg Phe Trp Val Ser Gly Gly Tyr Ile Asp Ser Asn Ile Asn
                260                 265                 270

Thr Asn Glu Gly Arg Thr Gly Lys Asp Ala Asn Ser Leu Leu Ala Ser
            275                 280                 285

Ile His Thr Phe Asp Pro Ser Leu Gly Cys Asp Ala Ser Thr Phe Gln
        290                 295                 300

Pro Cys Ser Asp Lys Ala Leu Ser Asn Leu Lys Val Val Asp Ser
305                 310                 315                 320

Phe Arg Ser Ile Tyr Gly Val Asn Lys Gly Ile Pro Ala Gly Ser Ala
                325                 330                 335

Val Ala Ile Gly Arg Tyr Pro Glu Asp Val Tyr Phe Asn Gly Asn Pro
                340                 345                 350

Trp Tyr Leu Ala Thr Phe Ala Ala Glu Gln Leu Tyr Asp Ser Val
            355                 360                 365

Tyr Val Trp Lys Lys Thr Gly Ser Ile Thr Val Thr Ser Thr Ser Leu
        370                 375                 380

Ala Phe Phe Gln Glu Leu Val Pro Gly Val Ala Ala Gly Thr Tyr Ser
385                 390                 395                 400

Ser Ser Gln Ser Thr Phe Thr Ser Ile Ile Asn Ala Val Ser Thr Tyr
                405                 410                 415

Ala Asp Gly Phe Leu Ser Glu Ala Ala Lys Tyr Val Pro Ala Asp Gly
                420                 425                 430

Ser Leu Ala Glu Gln Phe Asp Arg Asn Thr Gly Thr Pro Leu Ser Ala
            435                 440                 445

Val His Leu Thr Trp Ser Tyr Ala Ser Phe Leu Thr Ala Ala Ala Arg
        450                 455                 460

Arg Ala Gly Val Val Pro Pro Ser Trp Ala Ser Ser Gly Ala Asn Ser
465                 470                 475                 480

Val Pro Ser Ser Cys Ser Gly Ala Ser Val Val Gly Ser Tyr Ser Arg
                485                 490                 495

Pro Thr Ala Thr Ser Phe Pro Pro Ser Gln Thr Pro Lys Pro Gly Val
                500                 505                 510

Pro Ser Gly Thr Pro Phe Thr Pro Ile Pro Cys Ala Thr Pro Thr Ser
            515                 520                 525

Val Ala Val Thr Phe His Glu Leu Ala Thr Thr Gln Phe Gly Gln Thr
        530                 535                 540

Ile Lys Val Ala Gly Ser Ala Pro Glu Leu Gly Asn Trp Ser Thr Ser
545                 550                 555                 560

Ala Ala Ile Ala Leu Asp Ala Val Asn Tyr Ala Thr Asn His Pro Leu
                565                 570                 575

Trp Ile Gly Ser Val Ser Leu Glu Ala Gly Asp Val Ile Glu Tyr Lys
                580                 585                 590

Tyr Ile Asn Val Gly Gln Asp Gly Ser Val Thr Trp Glu Ser Asp Pro
            595                 600                 605

Asn His Thr Tyr Thr Val Pro Ala Val Ala Cys Val Thr Glu Val Val
        610                 615                 620

Lys Glu Asp Thr Trp Gln Ser
625                 630
```

<210> SEQ ID NO 17
<211> LENGTH: 632
<212> TYPE: PRT
<213> ORGANISM: Trichoderma strictipilis
<220> FEATURE:
<221> NAME/KEY: misc_feature
<222> LOCATION: (1)..(632)
<223> OTHER INFORMATION: full-length GA from Trichoderma strictipilis

<400> SEQUENCE: 17

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Ile Thr Lys
            20                  25                  30

Arg Ser Val Asp Asp Phe Ile Ser Thr Gln Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Asp Pro Asp Tyr
65                  70                  75                  80

Tyr Tyr Met Trp Thr Arg Asp Ser Ala Leu Val Phe Lys Asn Leu Val
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Thr Asn Pro Ser
        115                 120                 125

Gly Ser Leu Ala Asp Gly Ser Gly Leu Gly Glu Pro Lys Phe Glu Leu
    130                 135                 140

Thr Leu Ser Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Ser Tyr Ala Ala Gln Tyr Trp Asn Gln Thr Gly Phe
        195                 200                 205

Asp Leu Trp Glu Glu Val Ser Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Thr Tyr Ser Ser Val Ala Pro Gln Ile Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Ile Leu Thr
        275                 280                 285

Ser Ile His Thr Phe Asp Pro Asn Leu Gly Cys Asp Ala Gly Thr Phe
    290                 295                 300

Gln Pro Cys Ser Asp Lys Ala Leu Ser Asn Phe Lys Val Val Asp
305                 310                 315                 320

Ser Phe Arg Ser Ile Tyr Gly Val Asn Asn Gly Ile Pro Ala Gly Ala
                325                 330                 335

Ala Val Ala Ile Gly Arg Tyr Pro Glu Asp Val Tyr Phe Asn Gly Asn
            340                 345                 350

```
Pro Trp Tyr Leu Ala Thr Phe Ala Ala Glu Gln Leu Tyr Asp Ala
        355                 360                 365

Ile Tyr Val Trp Lys Lys Thr Gly Ser Ile Thr Val Thr Ala Ile Ser
370                 375                 380

Leu Ala Phe Phe Gln Glu Leu Val Pro Gly Val Thr Ala Gly Thr Tyr
385                 390                 395                 400

Ser Ser Ser Gln Ser Thr Phe Thr Asn Ile Ile Asn Ala Ala Ser Thr
                405                 410                 415

Tyr Ala Asp Gly Phe Val Thr Glu Ala Ala Lys Tyr Val Pro Thr Asp
                420                 425                 430

Gly Ser Leu Ala Glu Gln Phe Asp Arg Asn Asn Gly Thr Pro Leu Ser
            435                 440                 445

Ala Leu His Leu Thr Trp Ser Tyr Ala Ser Phe Leu Thr Ala Ser Ala
        450                 455                 460

Arg Arg Ala Gly Val Val Pro Pro Ser Trp Ala Asn Ser Ser Ala Ser
465                 470                 475                 480

Ser Ile Ser Ser Thr Cys Ser Gly Ala Ser Val Val Gly Ser Tyr Ser
                485                 490                 495

Ser Pro Thr Ala Thr Ser Phe Pro Pro Ser Gln Thr Pro Lys Pro Gly
                500                 505                 510

Val Pro Ser Gly Thr Pro Tyr Thr Pro Leu Pro Cys Ala Thr Pro Thr
            515                 520                 525

Ser Val Ala Val Thr Phe His Glu Leu Val Ser Thr Gln Phe Gly Gln
        530                 535                 540

Thr Val Lys Ala Ala Gly Ser Ala Pro Ala Leu Gly Asn Trp Ser Thr
545                 550                 555                 560

Ser Ala Ala Val Gly Leu Asp Ala Val Asn Tyr Ala Asp Asn His Pro
                565                 570                 575

Leu Trp Ile Gly Thr Val Glu Leu Glu Ala Gly Asp Val Val Glu Tyr
                580                 585                 590

Lys Tyr Ile Asn Val Gly Gln Asp Gly Ser Val Thr Trp Glu Ser Asp
            595                 600                 605

Pro Asn His Thr Tyr Thr Val Pro Ala Val Ala Cys Val Thr Glu Val
        610                 615                 620

Val Lys Glu Asp Thr Trp Gln Ser
625                 630

<210> SEQ ID NO 18
<211> LENGTH: 631
<212> TYPE: PRT
<213> ORGANISM: Trichoderma virens
<220> FEATURE:
<221> NAME/KEY: misc_feature
<222> LOCATION: (1)..(631)
<223> OTHER INFORMATION: full-length GA from Trichoderma virens Gv29-8

<400> SEQUENCE: 18

Met His Val Leu Ser Thr Ala Val Leu Leu Gly Ser Val Ala Val Gln
1               5                   10                  15

Lys Val Leu Gly Arg Pro Gly Ser Asn Gly Leu Ser Asp Ile Thr Lys
            20                  25                  30

Arg Ser Val Asp Ser Phe Ile Ser Ala Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Val Asp Pro Asp Tyr
```

```
                65                  70                  75                  80
Tyr Tyr Met Trp Thr Arg Asp Ser Ala Leu Val Phe Lys Asn Ile Val
                        85                  90                  95
Asp Arg Phe Thr Gln Lys Tyr Asp Ala Gly Leu Gln Arg Arg Ile Glu
                        100                 105                 110
Gln Tyr Ile Ser Ala Gln Val Thr Leu Gln Gly Ile Ser Asn Pro Ser
                        115                 120                 125
Gly Ser Leu Ser Asp Gly Ser Gly Leu Gly Glu Pro Lys Phe Glu Leu
            130                 135                 140
Thr Leu Asn Gln Phe Thr Gly Asn Trp Gly Arg Pro Gln Arg Asp Gly
145                 150                 155                 160
Pro Ala Leu Arg Ala Ile Ala Leu Ile Gly Tyr Ser Lys Trp Leu Ile
                        165                 170                 175
Asn Asn Asn Tyr Gln Ser Thr Val Ser Ser Val Ile Trp Pro Ile Val
                        180                 185                 190
Lys Asn Asp Leu Asn Tyr Val Ala Gln Tyr Trp Asn Gln Thr Gly Phe
                        195                 200                 205
Asp Leu Trp Glu Glu Val Asn Gly Ser Ser Phe Phe Thr Val Ala Asn
            210                 215                 220
Gln His Arg Ala Leu Val Glu Gly Ala Thr Leu Ala Thr Leu Gly
225                 230                 235                 240
Gln Ser Gly Ser Thr Tyr Ser Ser Val Ala Pro Gln Ile Leu Cys Phe
                        245                 250                 255
Leu Gln Arg Phe Trp Val Ser Gly Ser Tyr Ile Asp Ser Asn Ile Asn
                        260                 265                 270
Val Asn Glu Gly Arg Thr Gly Lys Asp Ala Asn Ser Leu Leu Ala Ser
                        275                 280                 285
Ile His Thr Phe Asp Pro Ser Leu Gly Cys Asp Ala Ser Thr Phe Gln
            290                 295                 300
Pro Cys Ser Asp Lys Ala Leu Ser Asn Leu Lys Val Val Asp Ser
305                 310                 315                 320
Phe Arg Ser Ile Tyr Gly Val Asn Ser Gly Ile Ser Ala Ser Ser Ala
                        325                 330                 335
Val Ala Ile Gly Arg Tyr Pro Glu Asp Val Tyr Phe Asn Gly Asn Pro
                        340                 345                 350
Trp Tyr Leu Ala Thr Phe Ala Ala Ala Glu Gln Leu Tyr Asp Ala Leu
                        355                 360                 365
Tyr Val Trp Lys Gln Ala Gly Ser Ile Thr Val Thr Ser Thr Ser Leu
                        370                 375                 380
Ala Phe Phe Gln Gln Leu Val Pro Gly Val Ala Ala Gly Thr Tyr Ser
385                 390                 395                 400
Ser Ser Gln Ser Thr Tyr Thr Ser Ile Ile Asn Ala Val Ser Ala Tyr
                        405                 410                 415
Ala Asp Gly Phe Met Asn Glu Ala Ala Lys Tyr Val Pro Ala Asp Gly
                        420                 425                 430
Ser Leu Ala Glu Gln Phe Asp Lys Asn Ser Gly Thr Pro Leu Ser Ala
            435                 440                 445
Val His Leu Thr Trp Ser Tyr Ala Ser Phe Leu Thr Ala Ala Asp Arg
            450                 455                 460
Arg Ala Gly Ile Val Pro Ser Ser Trp Ala Ser Ser Gly Ala Asn Thr
465                 470                 475                 480
Val Pro Ser Ser Cys Ser Gly Ala Ser Val Val Gly Ser Tyr Ser Arg
                        485                 490                 495
```

-continued

Pro Thr Ala Thr Ser Phe Pro Pro Ser Gln Thr Pro Lys Pro Gly Val
            500                 505                 510

Pro Ser Gly Thr Pro Phe Thr Pro Ile Pro Cys Ala Thr Pro Thr Ser
        515                 520                 525

Val Ala Val Thr Phe His Glu Leu Ala Thr Thr Gln Phe Gly Gln Thr
        530                 535                 540

Ile Lys Val Val Gly Ser Val Pro Glu Leu Gly Asn Trp Ser Thr Asn
545                 550                 555                 560

Ala Ala Val Ala Leu Asn Ala Val Asn Tyr Ala Ser Asn His Pro Leu
                565                 570                 575

Trp Leu Gly Ser Ile Asn Leu Ala Ala Gly Glu Val Val Gln Tyr Lys
            580                 585                 590

Tyr Ile Asn Val Gly Ser Asp Gly Ser Val Thr Trp Glu Ser Asp Pro
        595                 600                 605

Asn His Thr Tyr Thr Val Pro Ala Val Ala Cys Val Thr Gln Val Val
        610                 615                 620

Lys Glu Asp Thr Trp Gln Ser
625                 630

<210> SEQ ID NO 19
<211> LENGTH: 627
<212> TYPE: PRT
<213> ORGANISM: Trichoderma atroviride
<220> FEATURE:
<221> NAME/KEY: misc_feature
<222> LOCATION: (1)..(627)
<223> OTHER INFORMATION: full-length GA from Trichoderma atroviride IMI
      206040

<400> SEQUENCE: 19

Met His Val Leu Ser Thr Ala Val Leu Leu Gly Ser Val Ala Val Gln
1               5                   10                  15

Lys Val Leu Gly Arg Pro Gly Ala Ser Asp Ile Thr Lys Arg Ala Val
            20                  25                  30

Thr Asp Phe Ile Asn Ser Glu Thr Pro Ile Ala Leu Asn Asn Leu Ile
        35                  40                  45

Cys Asn Val Gly Pro Asp Gly Cys Arg Ala Phe Gly Thr Ser Ile Gly
    50                  55                  60

Ala Val Val Ala Ser Pro Ser Thr Thr Asp Pro Asp Tyr Phe Tyr Met
65                  70                  75                  80

Trp Thr Arg Asp Ser Ala Leu Val Phe Lys Thr Leu Val Asp Arg Phe
                85                  90                  95

Thr Gln Asn Tyr Asp Ala Gly Leu Gln Arg Arg Ile Glu Gln Tyr Ile
            100                 105                 110

Ala Ala Gln Val Thr Leu Gln Gly Ile Ser Asn Pro Ser Gly Ser Leu
        115                 120                 125

Ser Asp Gly Ser Gly Leu Gly Glu Pro Lys Phe Glu Leu Thr Leu Ser
    130                 135                 140

Gln Phe Thr Gly Asn Trp Gly Arg Pro Gln Arg Asp Gly Pro Ala Leu
145                 150                 155                 160

Arg Ala Ile Ala Leu Ile Gly Tyr Ser Lys Trp Leu Ile Ser Asn Asn
                165                 170                 175

Tyr Gln Ser Thr Val Ser Asn Ile Ile Trp Pro Ile Val Arg Asn Asp
            180                 185                 190

Leu Asn Tyr Val Ala Gln Tyr Trp Asn Gln Thr Gly Phe Asp Leu Trp
        195                 200                 205

```
Glu Val Asn Gly Ser Ser Phe Phe Thr Val Ala Asn Gln His Arg
210                 215                 220
Ala Leu Val Glu Gly Ala Thr Leu Ala Thr Thr Leu Gly Gln Ser Gly
225                 230                 235                 240
Ser Ser Tyr Ser Thr Val Ala Pro Gln Ile Leu Cys Phe Leu Gln Lys
                245                 250                 255
Phe Trp Ser Pro Ser Gly Tyr Val Ile Ser Asn Ile Asn Ser Asn Asp
            260                 265                 270
Gly Arg Thr Gly Lys Asp Ser Asn Ser Ile Leu Thr Ser Ile His Thr
        275                 280                 285
Phe Asp Pro Ser Ile Gly Cys Asp Ala Ala Thr Phe Gln Pro Cys Ser
    290                 295                 300
Asp Lys Ala Leu Ser Asn Leu Lys Val Tyr Val Asp Ser Phe Arg Ser
305                 310                 315                 320
Ile Tyr Gly Val Asn Ser Gly Ile Pro Ala Gly Thr Ala Val Ala Val
                325                 330                 335
Gly Arg Tyr Pro Glu Asp Val Tyr Phe Asn Gly Asn Pro Trp Tyr Leu
            340                 345                 350
Ser Thr Phe Ala Val Ala Glu Gln Leu Tyr Asp Ala Leu Tyr Val Trp
        355                 360                 365
Lys Lys Thr Gly Ser Ile Thr Val Thr Ser Thr Ser Leu Ala Phe Phe
    370                 375                 380
Gln Glu Leu Val Pro Ser Val Thr Ala Gly Thr Tyr Ala Ser Ser Ser
385                 390                 395                 400
Ser Thr Phe Thr Ser Ile Val Asn Ala Val Ser Thr Tyr Ala Asp Gly
                405                 410                 415
Phe Val Ser Glu Ala Ala Lys Tyr Val Pro Ser Asp Gly Ser Leu Ser
            420                 425                 430
Glu Gln Phe Asp Lys Asn Thr Gly Thr Pro Leu Ser Ala Val His Leu
        435                 440                 445
Thr Trp Ser Tyr Ala Ser Phe Leu Thr Ala Thr Ala Arg Arg Ala Gly
    450                 455                 460
Ile Val Pro Pro Ser Trp Ile Ser Ser Gly Ala Asn Thr Val Pro Ser
465                 470                 475                 480
Ser Cys Ser Gly Thr Thr Val Ala Gly Ser Tyr Ser Pro Thr Ala
                485                 490                 495
Thr Ser Phe Pro Pro Ser Gln Thr Pro Lys Thr Ala Ala Thr Gly Thr
            500                 505                 510
Ser Phe Thr Pro Ile Ala Cys Ala Thr Pro Thr Ser Val Ala Val Thr
        515                 520                 525
Phe His Glu Leu Ala Thr Thr Val Pro Gly Gln Thr Ile Lys Val Val
    530                 535                 540
Gly Asn Ala Gln Ala Leu Gly Asn Trp Ser Thr Ser Ala Gly Val Ala
545                 550                 555                 560
Leu Asn Ala Val Asn Tyr Ala Ser Asn His Pro Leu Trp Ile Gly Pro
                565                 570                 575
Val Asn Leu Lys Ala Gly Asp Val Val Glu Tyr Lys Tyr Ile Asn Val
            580                 585                 590
Gly Ser Asp Gly Ser Val Thr Trp Glu Ala Asp Pro Asn His Thr Tyr
        595                 600                 605
```

```
Thr Val Pro Ala Val Ala Cys Val Thr Ala Val Val Lys Glu Asp Thr
    610                 615                 620
Trp Gln Ser
625
```